(12) United States Patent
Eswarakumar et al.

(10) Patent No.: US 7,872,016 B2
(45) Date of Patent: Jan. 18, 2011

(54) METHOD FOR TREATING SKELETAL DISORDERS RESULTING FROM FGFR MALFUNCTION

(75) Inventors: Veraragavan Palani Eswarakumar, New Haven, CT (US); Joseph P. Schlessinger, Woodbridge, CT (US); Irit Lax, Woodbridge, CT (US)

(73) Assignee: Yale University, New Haven, CT (US)

( * ) Notice: Subject to any disclaimer, the term of this patent is extended or adjusted under 35 U.S.C. 154(b) by 194 days.

(21) Appl. No.: 11/597,487

(22) PCT Filed: May 25, 2005

(86) PCT No.: PCT/US2005/018601

§ 371 (c)(1),
(2), (4) Date: Mar. 17, 2008

(87) PCT Pub. No.: WO2005/115363

PCT Pub. Date: Dec. 8, 2005

(65) Prior Publication Data

US 2008/0317739 A1   Dec. 25, 2008

Related U.S. Application Data

(60) Provisional application No. 60/574,085, filed on May 25, 2004.

(51) Int. Cl.
*A61K 31/435* (2006.01)
*A61K 31/41* (2006.01)
*C07D 471/02* (2006.01)

(52) U.S. Cl. ................... 514/300; 514/277; 514/279; 514/299; 514/359; 514/408; 514/410; 514/412; 546/113

(58) Field of Classification Search ............ None
See application file for complete search history.

(56) References Cited

U.S. PATENT DOCUMENTS

2002/0086972 A1   7/2002   Kouhara et al.

FOREIGN PATENT DOCUMENTS

EP   1332761 A1   8/2003
WO   WO 01/04160 A1   1/2001
WO   WO 03/076467 A1   9/2003

OTHER PUBLICATIONS

Arman et al., "Fgfr2 is Reuired for Limb Outgrowth and lung-Branching Morphongenesis," Proceedings of the national Academy of Science of USA 96(21):11895-11899 (1999).
Dailey et al., "Mechanisms Underlying Differential Responses to FGF Signaling," Cytokine and Growth Factor Reviews 16(2):233-247 (2005).
Eswarakumar et al., "Cellular Signaling by Fibroblast Growth Factor Receeptors," Cytokine and Growth Factor Reviews 16(2)139-149 (2005).
Mansukhani et al., "Signaling by Fibroblast Growth Factors (FGF) and Fibroblast Growth Factor Receeptor 2 (FGFR2)-Activating Mutations Blocks Mineralization and Induces Apoptosis in Osteoblasts," The Journal of Cell Biology, Rockefeller University Press 149(6):1297-1308 (2000).
Mood et al., "SNT1/FRS2 Mediates Germinal Vesicle Breakdown Induced by an Activated FGF Receptor 1 in Xenopus Oocytes," Journal of Biological chemistry 277(36):33196-33204 (2002).

*Primary Examiner*—Christine J Saoud
(74) *Attorney, Agent, or Firm*—Wolf, Greenfield & Sacks, P.C.

(57) ABSTRACT

The invention provides materials, reagents, systems, and methods for identifying agents useful for treating diseases resulting from abnormal (e.g., excessive) FGF receptor signaling. The invention also provides (therapeutic) agents thus identified, and methods of using such agents in treating such diseases. In certain embodiments, the invention relates to the treatment of various craniofacial disorders, or Craniosynostosis, that result from FGFR (e.g. FGFR2) malfunction, such as Crouzon, Apert, Jackson-Weiss, Pfeiffer Syndromes, Crouzon+acanthosis nigricans, Beare-Stevenson cutis gyrata, and non-syndromic craniosynostosis (NS). The methods comprise administering to the individuals a therapeutically effective amount of an inhibitor of the FGFR2c-FRS2 signaling. The inhibitor inhibits signaling by antagonizing FGFR2c-FRS2 interaction, inhibiting the expression and/or subcellular localization of wild-type or mutant FGFR2c and/or FRS2, inhibiting the kinase activity of FGFR2c (e.g. for autophosphorylation and/or phosphorylation of FRS2), and/or inhibiting downstream signaling of FRS2 (such as Sos-Ras-MAPK, Shp2, and/or Gab 1-PI3K pathways).

8 Claims, 20 Drawing Sheets

C342Y MUTANT

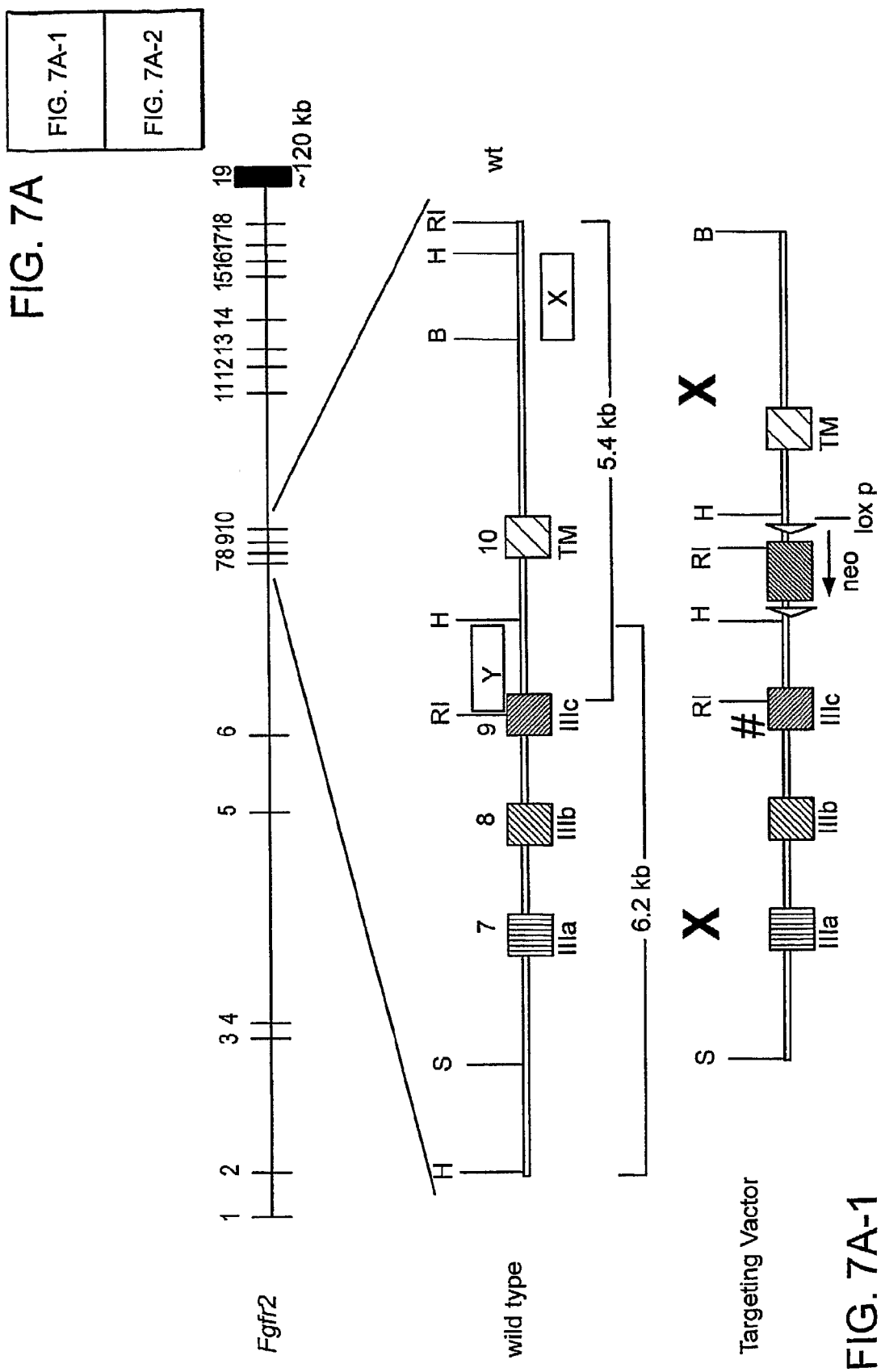

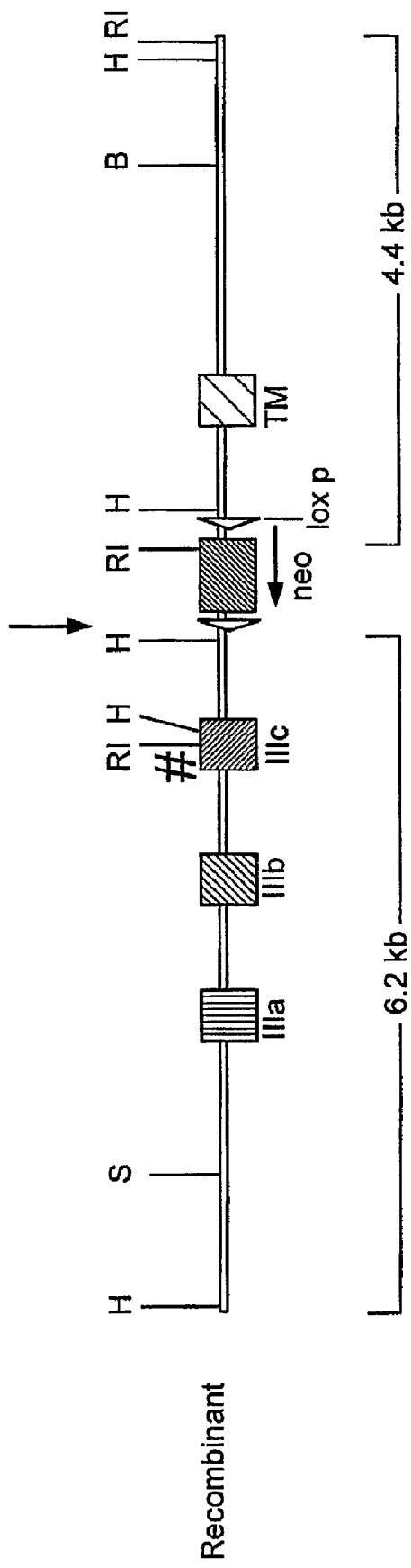

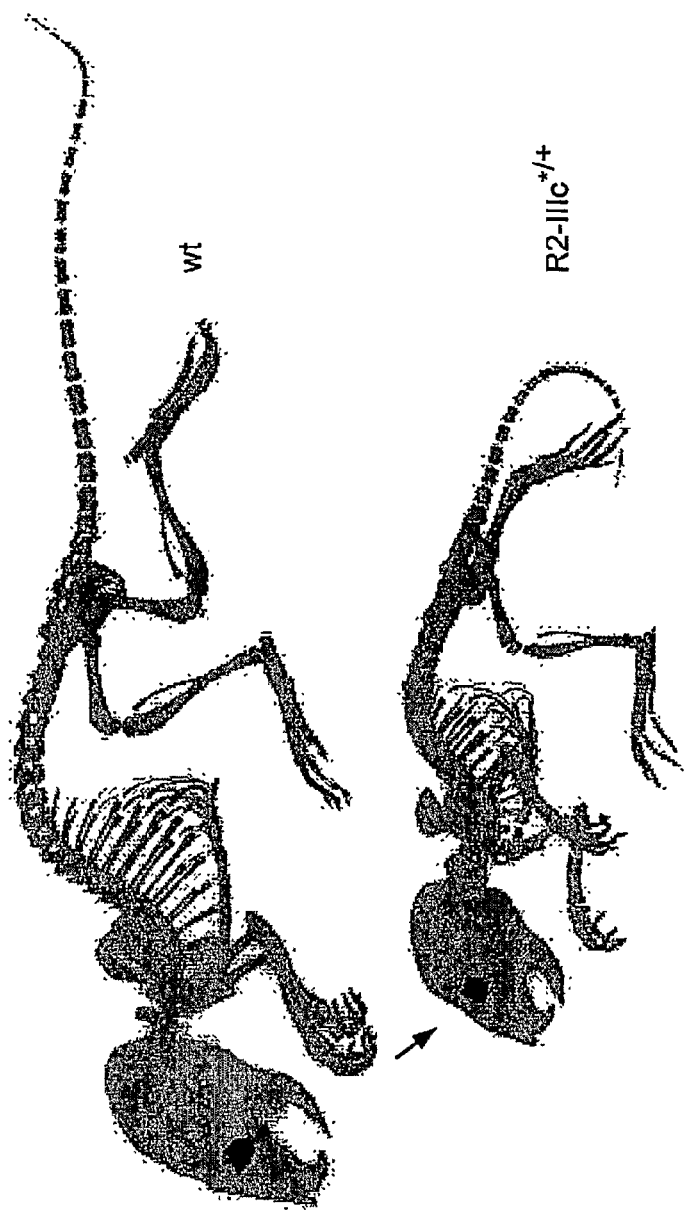
P-14 skeletons of wt and IIIc gain of function mutant mice
FIG. 8

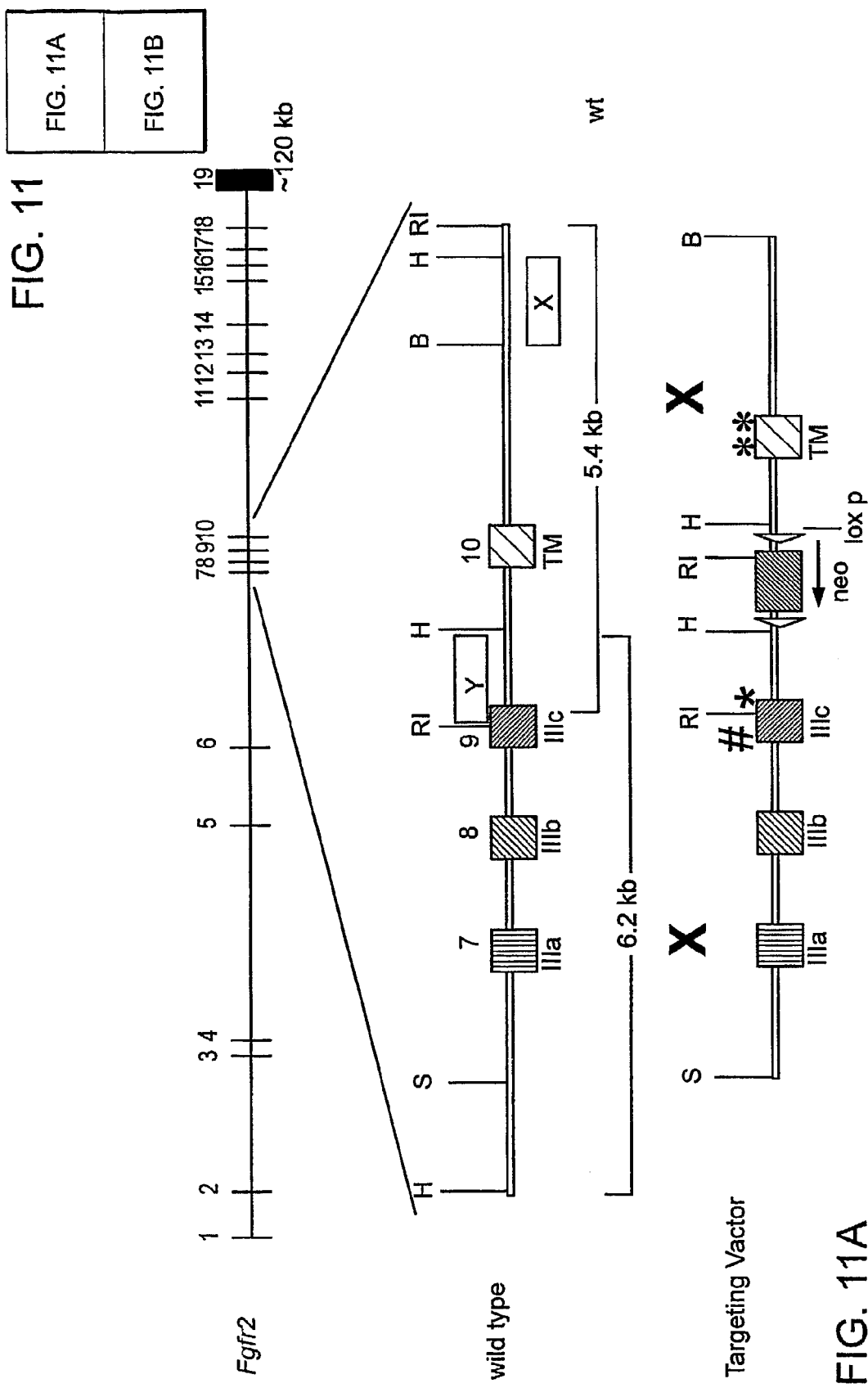

C342Y & LR Double Mutant (CLR)

METHOD FOR TREATING SKELETAL DISORDERS RESULTING FROM FGFR MALFUNCTION

REFERENCE TO RELATED APPLICATIONS

This application is a national stage filing under 35 U.S.C. 371 of International Application PCT/US2005/018601 designating the United States of America, and filed May 25, 2005 and claims the benefit under 35 U.S.C. §119(e) of U.S. provisional application No. 60/574,085, filed May 25, 2004. The teachings of both referenced applications are incorporated by reference herein.

GOVERNMENT SUPPORT

Work described herein was funded, in whole or in part, by Grant Nos. RO1-AR051448 and RO1-AR051886 from the National Institutes of Health (NIH). The United States government has certain rights in the invention.

BACKGROUND OF THE INVENTION

Development of the skull is a complex process regulated by unique signaling mechanism that differ significantly from those required for the development of the axial (e.g. vertebral column, ribs, sternum) and appendicular (e.g. limbs, girdles) skeletons (Helms and Schneider, *Nature* 423: 326-331, 2003). While migrating neural crest cells differentiate into osteoblasts and chondrocytes to form the bones of the facial region, the cranial vault, which encapsulates the brain, is formed by direct differentiation of the paraxial mesodermal cells into osteoblasts without a cartilage intermediate (Jiang et al., *Dev Biol* 241: 106-116, 2002). To accommodate the rapidly growing brain during the early years of life, the cranial bones grow at their fibrous joints called sutures. These sutures contain immature, rapidly dividing osteogenic stem cells (Wilkie, *Hum Mol Genet.* 6: 1647-1656, 1997). It has been shown that signaling pathways that are activated by fibroblast growth factors (FGFs), bone morphogenetic proteins (BMPs) (Kim et al., *Development* 125: 1241-1251, 1998), transforming growth factor βs (TGF-βs) (Cohen, *J Bone Miner Res* 12: 322-331, 1997) and more recently noggin (Warren et al., *Nature* 422: 625-629, 2003) play an important role in suture development.

Craniosynostosis, the premature fusion of one or more sutures of the skull before the brain completes its growth, is one of the most common craniofacial abnormalities at birth caused by abnormal signaling in the sutural mesenchyine and occurs with a prevalence of approximately 1 in 2100-3000 births (Hehr and Muenke, *Mol Genet Metab* 68: 139-151, 1999). Hallmarks of craniosynostosis include abnormally shaped skull often associated with increased intracranial pressure, mental retardation, developmental delay, seizures and blindness that are caused by the constriction of the growing brain (Nuckolls et al., *Cleft Palate Craniofac J* 36: 12-26, 1999). It is now well established that gain of function mutations in members of the FGFR family of receptor tyrosine kinases (RTKs) cause syndromic craniosynostosis, which accounts for 15-20% of all known craniosynostosis disorders (Passos-Bueno et al., *Hum Mutat* 14: 115-125, 1999). For example, mutations in FGFR2 cause Crouzon, Apert, Pfeiffer, Jackson-Weiss and Beare-Stevenson syndromes. It is noteworthy that these individuals have a normal allele of Fgfr2c in addition to the mutated allele.

Crouzon syndrome is caused by mutations in the gene for fibroblast growth factor receptor-2 (FGFR2). Crouzon syndrome with acanthosis nigricans results from a mutation in the FGFR3 gene. Crouzon syndrome is characterized by cranial synostosis, hypertelorism, exophthalmos and external strabismus, parrot-beaked nose, short upper lip, hypoplastic maxilla, and a relative mandibular prognathism. Familial occurrence was noted by Crouzon (*Bull. Mem. Soc. Med. Hop. Paris* 33: 545-555, 1912) when he first described the syndrome. Subsequently, several investigators have demonstrated an autosomal dominant mode of inheritance, although sporadic cases have also been reported. There was marked variability in both cranial and facial manifestations of the syndrome. Two described sporadic cases also had syndactylism of both hands and feet, and may be more correctly labeled Vogt cephalodactyl). Cohen and Kreiborg (*Clin. Genet.* 41: 12-15, 1992) estimated that Crouzon syndrome represents approximately 4.8% of cases of craniosynostosis at birth. The birth prevalence was estimated to be 16.5 per million births.

There is strong evidence that Jackson-Weiss syndrome is caused by mutation in the gene encoding fibroblast growth factor receptor-2, although Roscioli et al. (*Am. J. Med. Genet.* 93: 22-28, 2000) reported an individual with what they considered to be the Jackson-Weiss syndrome, who had the FGFR1 pro252-to-arg mutation. Jackson et al. (*J. Pediat.* 88: 963-968, 1976) reported a syndrome of craniosynostosis, midfacial hypoplasia, and foot anomalies in an Amish kindred. It resembles Pfeiffer syndrome, in that there is enlarged great toes and craniofacial abnormalities. However, thumb abnormalities were not present. An autosomal dominant pedigree pattern with variable severity was observed in this disease. Indeed, phenotypic expression was so variable that the entire spectrum of the dominantly inherited craniofacial dysostoses and acrocephalosyndactylies (except classic Apert syndrome) was seen in the kindred. Apparent validation of the Jackson-Weiss syndrome was provided by reports of Escobar and Bixler (*Birth Defects Orig. Art. Ser.* XIII(3C): 139-154, 1977) and families observed by Cohen others. By 2-point linkage and haplotype analyses using 13 dinucleotide repeat markers on chromosome 10, Li et al. (*Genomics* 22: 418-424, 1994) showed that the Jackson-Weiss syndrome maps to the same region, 10q23-q26, as the Crouzon syndrome. In a study of the family in which the Jackson-Weiss syndrome was originally described, Jabs et al. (*Nature Genet.* 8: 275-279, 1994) discovered a mutation in the conserved region of the immunoglobulin IIIc domain of the gene for fibroblast growth factor receptor-2. The mutation was an ala344-to-gly missense mutation (A344G). Mutations in the FGFR2 gene have also been found in individuals with Crouzon syndrome. Heike et al. (*Am. J. Med. Genet.* 100: 315-324, 2001) studied a previously unrecognized branch of the original family reported by Jackson et al. (supra) and found the A344G mutation in FGFR2 in all affected members.

Pfeiffer syndrome was originally reported in 8 affected individuals in 3 generations, with 2 instances of male-to-male transmission (Pfeiffer, *Z. Kinderheilk.* 90: 301-320, 1964). The striking feature was broad, short thumbs and big toes. The proximal phalanx of the thumb was either triangular or trapezoid (and occasionally fused with the distal phalanx) so that the thumb pointed outward (i.e., away from the other digits). Evidence presented by Muenke et al. (*Nature Genet.* 8: 269-274, 1994) indicates that mutations in the gene for FGFR1 can cause familial Pfeiffer syndrome. The disorder can also be caused by mutation in the gene for FGFR2. The original family reported by Pfeiffer (supra) was of this type. In an individual with severe Pfeiffer phenotype, Tartaglia et al. (*Hum. Genet.* 99: 602-606, 1997) reported a de novo G-to-C transversion in exon IIIa of the FGFR2 gene, resulting in a Trp-to-Cys missense mutation at codon 290. Schaefer et al. (*Am. J. Med. Genet.* 75: 252-255, 1998) likewise found a Trp290-to-Cys mutation in a case of Pfeiffer syndrome type 2. A Trp290-to-Arg substitution was found by Meyers et al. (*Am. J. Hum. Genet.* 58: 491-498, 1996) in classic cases of Crouzon syndrome, whereas the Trp290-to-Gly mutation resulted in an atypically mild form of Crouzon syndrome (Park et al., *Hum. Molec. Genet.* 4: 1229-1233, 1995). Plomp et al. (*Am. J. Med. Genet.* 75: 245-251, 1998) reported 5 unrelated individuals with Pfeiffer syndrome type 2, two of the individuals showed the Cys342-to-Arg mutation.

Apert (*Bull. Mein. Soc. Med. Hop. Paris* 23: 1310-1330, 1906) defined a syndrome characterized by skull malformation (acrocephaly of brachysphenocephalic type) and syndactyly of the hands and feet of a special type (complete distal fusion with a tendency to fusion also of the bony structures). The hand, when all the fingers are webbed, has been compared to a spoon and, when the thumb is free, to an obstetric hand. A frequency of Apert syndrome of 1 in 160,000 births was estimated. There is strong evidence (Wilkie et al., Apert syndrome results from localized mutations of FGFR2 and is allelic with Crouzon syndrome *Nature Genet.* 9: 165-172, 1995) that Apert syndrome results from mutations in the gene encoding FGFR2. Oldridge et al. (*Am. J. Hum. Genet.* 64: 446-461, 1999) analyzed 260 unrelated individuals with Apert syndrome and found that 258 had missense mutations in exon 7 of FGFR2, which affected a dipeptide in the linker region between the second and third immunoglobulin-like domains. Hence, the molecular mechanism of Apert syndrome is exquisitely specific. Studies of fibroblasts showed ectopic expression of the keratinocyte growth factor receptor (KGFR) domain of FGFR2, which correlated with the severity of limb abnormalities. This correlation provided genetic evidence that signaling through KGFR causes syndactyly in Apert syndrome. The missense mutations in exon 7 of the 258 patients were ser252 to trp in 172 patients, ser252 to phe in 1 patient, and pro253 to arg in 85 patients.

There is a need to develop new treatment methods for treating these related syndromes.

SUMMARY OF THE INVENTION

The invention relates to methods of altering, such as interfering with, the signaling (e.g., interaction and/or phosphorylation, etc.) between FGF receptor (FGFR) and one of its downstream signaling molecules, FRS2. In one embodiment, the present invention is a method of interfering with or reducing FRS2-mediated cell signal transduction, in which cells are contacted with an agent (also referred to as a drug) which interferes with FGFR-FRS2 function, under conditions under which the agent enters the cells. This can be carried out, for example, by contacting cells with an agent that interferes with interactions between the PTB domain of FRS2 and the juxtamembrane domain of FGFR2 and/or reduces phosphorylation of FRS2. The invention further relates to methods of reducing in an individual the severity of a skeletal deformity caused by a gain of function mutation in FGFR. Such methods are useful in preventing, treating, and/or alleviating (e.g., reducing the severity of) conditions, such as a number of closely related skeletal defects, especially in craniofacial regions and limbs extremities, resulting from abnormal (e.g. excessive) FRS2-mediated FGFR signaling, in a mammal, such as a human.

Excessive FGFR signaling through FRS2 is responsible for a number of dominantly transmitted genetic disorders, such as Crouzon syndrome, Apert syndrome, Jackson-Weiss syndrome, Pfeiffer syndrome, Crouzon+acanthosis nigricans, Beare-Stevenson cutis gyrata, non-syndromic craniosynostosis (NS), Muenke syndrome, Saethre-Chotzen-like syndrome, Achondroplasia (ACH), SADDEN (severe achondroplasia with developmental delay and acanthosis nigricans), Thanatophoric dysplasia type I (TDI), Thanatophoric dysplasia type II (TDII), or Hypochondroplasia (HCH), as well as some malignancies. Surprisingly, abolishing FRS2-mediated FGFR signaling, even without substantially affecting FGFR signaling through its other downstream targets (such as Shp2 and PLCγ), corrects the phenotypic defects resulting from excessive FGFR activity in an in vivo genetic mouse model. In vitro experiments using a compound that attenuates excessive FGFR signaling also confirm the result, and provide a screening method for identifying additional compounds that abolish FGFR-FRS2 signaling.

The invention also provides a screening method for identifying such compounds, and their use as pharmaceutical compositions to treat individuals who have or are at risk of developing conditions characterized by abnormal (e.g. excessive) FRS2-mediated FGFR signaling.

More particularly, one aspect of the invention provides a method for specifically or selectively disrupting FRS2-mediated FGFR signaling, comprising contacting cells with an agent that specifically or selectively abolishes FGFR-FRS2 interaction. In another aspect, the invention provides a method for disrupting FRS2-mediated FGFR signaling, comprising contacting cells with an agent that abolishes FGFR-FRS2 signaling (e.g. interaction and/or phosphorylation, etc.).

In another embodiment, the invention is a method of preventing, treating, or alleviating (e.g., reducing the severity of) certain symptoms in an individual having abnormal FGFR activity that leads to a craniosynostosis syndrome and/or skeletal dysplasia condition, comprising administering to the individual a therapeutically effective amount of at least one therapeutic agent that antagonizes FGFR signaling through FRS2. In one embodiment, the therapeutic agent is administered shortly before or after the birth of the individual. In one embodiment, the therapeutic agent is administered postnatally for sufficient time (e.g., during skeletal development) and in appropriate doses to reduce the severity of a condition caused by gain of function mutation(s) in FGFR, such as FGFR2.

The methods and reagents of the invention may be applicable to a variety of abnormal FGFR activities. For example, in certain embodiments, the abnormal FGFR activity is excessive FGFR activity.

As used herein, the term "excessive FGFR activity" includes FGFR activity resulting from a constitutively activated mutation in the FGFR. In certain cases, such constitutively activating mutation may promote ligand-independent FGFR dimerization. For example, the ligand-independent FGFR dimerization may be effectuated by destabilizing the D3 immunoglobulin (Ig) like domain of the FGFR, and disrupting the normal intramolecular disulfide bond of the D3 Ig-like domain. Such disruption of D3 intramolecular disulfide bond may result from the mutation of at least one of the two conserved Cys residues (e.g., the conserved Cys corresponding to FGFR2 Cys-342) normally involved in intramolecular disulfide bond formation in the D3 Ig-like domain. The disruption of D3 intramolecular disulfide bond may also result from destabilizing mutations in residues other than the two conserved Cys residues normally involved in intramolecular disulfide bond formation in the D3 Ig-like domain.

As used herein, the term "excessive FGFR activity" also includes ligand-independent FGFR dimerization effectuated by intermolecular disulfide bond formation within the transmembrane region of FGFR.

"Excessive FGFR activity" may also result from a mutant FGFR with relaxed ligand-receptor specificity, such that the mutant FGFR can be activated by ligands which, in the absence of the mutation, do not activate the FGFR. For example, certain mutant FGFR comprises a mutation in one or both of the two highly conserved residues in the linker connecting the D2 and D3 Ig-like domains in FGFR; the two highly conserved residues correspond to Ser-252 and Pro-253 of FGFR2.

Excessive FGFR activity may also result from gain-of-function mutations in the catalytic RTK (Receptor Tyrosine Kinase) domain of FGFR, and the RTK domain exhibits enhanced activity in a ligand-independent manner.

Excessive FGFR activity may further result from overexpression of FGFR.

The term "FGFR" includes FGFR1, FGFR2, FGFR3, FGFR4, and their splicing isoforms. In one embodiment, the FGFR is FGFR2c.

The term "FRS2" includes both FRS2α and FRS2β. In one embodiment, the FRS2 is FRS2α.

The agent of the subject invention may exert its effect through a variety of means. The agent may, for example: (1) inhibit the interaction between FGFR and FRS2; (2) inhibit the expression of FGFR and/or FRS2; (3) inhibit the phosphorylation of FRS2 by FGFR, or increase the de-phosphorylation of FRS2 at residues phosphorylated by FGFR; (4) decrease the half-life or stability, or increase the degradation of FGFR and/or FRS2; (5) alter the proper subcellular localization of FGFR and/or FRS2; (6) decrease the abundance of the FGFR-FRS2 complex; and/or (7) decrease the expression level and/or activity of a gene downstream of FGFR-FRS2 signaling.

For instant, to alter the proper subcellular localization of FRS2, the N-terminal myristylation of FRS2 may be abolished or attenuated by using, for example, a myristylation inhibitor.

"A gene downstream of FGFR-FRS2 signaling" may include any gene that becomes activated upon FGFR-FRS2 signaling (e.g., FRS2 phosphorylation by FGFR). For example, the downstream gene may belong to the Sos-Ras-MAPK pathway, the Shp2 pathway, and/or the Gab1-PI3K pathway.

The agent of the invention may be used for preventing, treating, or alleviating the symptoms of a number of disease/conditions. For example, the agents may be effective against certain craniosynostosis syndromes and/or skeletal dysplasia conditions such as: Crouzon syndrome, Apert syndrome, Jackson-Weiss syndrome, Pfeiffer syndrome, Crouzon+acanthosis nigricans, Beare-Stevenson cutis gyrata, non-syndromic craniosynostosis (NS), Muenke syndrome, Saethre-Chotzen-like syndrome, Achondroplasia (ACH), SADDEN (severe achondroplasia with developmental delay and acanthosis nigricans), Thanatophoric dysplasia type I (TDI), Thanatophoric dysplasia type II (TDII), and/or Hypochondroplasia (HCH).

The agent of the invention may be different types of molecules in nature. For example, it may be an antibody or functional fragment thereof (e.g., polyclonal or monoclonal; intact or truncated, F(ab')$_2$, Fab, Fv; scFv, xenogeneic, allogeneic, syngeneic, or modified forms thereof, such as humanized or chimeric antibodies, etc.).

Alternatively, the agent may be a polypeptide or mimetic thereof. For instance, the polypeptide or mimetic may be a competing peptide comprising the binding domain of FRS2 for FGFR (e.g., the PTB domain), or the binding domain of FGFR for FRS2. The polypeptide or antibody may be in the form of a fusion protein.

In other embodiments, the agent of therapeutic agent may be a polynucleotide, such as an antisense polynucleotide of FGFR or FRS2, or an RNAi construct of FGFR or FRS2.

In yet other embodiments, the agent may be a small molecule compound, such as one with a molecular weight of no more than about 5000 Da, 4000 Da, 3000 Da, 2000 Da, 1000 Da, 500 Da, 300 Da, or about 100 Da.

In certain embodiments, the subject agents are 3-benzoyl-7-azaindole compounds, such as PLX052 (see FIG. 14C and below).

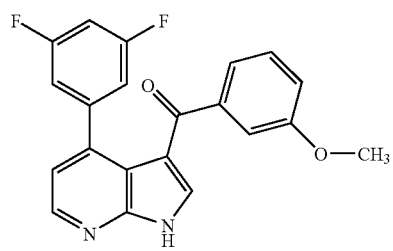

Such compounds may be substituted with one or more groups selected from nitro, cyano, hydroxyl, thiol, carboxyl, sulfate, or substituted or unsubstituted amino, alkoxy, alkylamino, alkylthio, hydroxyalkyl, alkoxyalkyl, aminoalkyl, thioalkyl, ether, thioether, ester, amide, thioester, carbonate, carbamate, urea, sulfonate, sulfone, sulfoxide, sulfonamide, alkyl, alkenyl, alkynyl, acyl, acyloxy, acylamino, aryl, heteroaryl, carbocyclyl, heterocyclyl, aralkyl, hetaralkyl, carbocyclylalkyl, and heterocyclylalkyl. In particular, the present 3-benzoyl-7-azaindole compounds may be substituted with one or more polar or ionic groups, which may increase aqueous solubility. For example, the 3-benzoyl-7-azaindole compounds may be substituted with one or more groups selected from nitro, cyano, hydroxyl, thiol, carboxyl, sulfate, or substituted or unsubstituted amino, alkoxy, alkylamino, hydroxyalkyl, alkoxyalkyl, aminoalkyl, ether, ester, amide, carbonate, carbamate, urea, sulfonate, sulfone, sulfoxide, sulfonamide, acyl, acyloxy, and acylamino.

In yet other embodiments, the agent may be a peptidomimetic.

The therapeutic agent of the invention may be formulated with pharmaceutically acceptable carriers.

The agent of the invention may be administered or used individually, may be administered with another agent or drug, or in conjunction with surgical treatment of the condition resulting from abnormal FGFR-FRS2 signaling.

Another aspect of the invention provides a method for screening for or identifying agents that antagonize FGFR signaling through FRS2, comprising: (1) forming a reaction mixture including FGFR and FRS2, under conditions under which the FGFR activates FRS2, (2) contacting the reaction mixture with a test agent, and (3) determining the effect of the test agent for one or more activities selected from the group consisting of: (a) a decrease in the interaction between FGFR and FRS2; (b) a decrease in the expression of FGFR and/or FRS2; (c) a decrease in the phosphorylation of FRS2 by FGFR, or increase in the de-phosphorylation of FRS2 at residues phosphorylated by FGFR; (d) a decrease in the half-life or stability, or increase in the degradation of FGFR and/or FRS2; (e) where the reaction mixture is a whole cell, a changed subcellular localization of FGFR and/or FRS2; (f) a decrease in the abundance of the FGFR-FRS2 complex; (g) a decrease in the expression level and/or activity of a gene downstream of FGFR-FRS2 signaling; wherein a positive observation in any of (a)-(g) is indicative that the test agent is an antagonist of FGFR signaling through FRS2.

The method can also include confirming that there is no substantial effect of the test agent on FGFR signaling independent of FRS2, such as PLCγ signaling and/or Shp2 signaling. Agents that specifically or selectively inhibits FRS2-mediated FGFR signaling are not expected to substantially affect other FRS2-independent FGFR signaling.

Another aspect of the invention relates to the use of an agent that blocks FGFR signaling through FRS2 in the manufacture of a medicament for the prevention, treatment, or alleviating symptoms in an individual having or at high risk of having skeletal deformity caused by a gain-of-function FGFR mutation. The skeletal deformity may be a craniosynostosis syndrome and/or a skeletal dysplasia condition.

Another aspect of the invention provides a pharmaceutical composition for the prevention, treatment, and/or alleviating symptoms in an individual having or at high risk of having skeletal deformity caused by a gain-of-function FGFR mutation. The pharmaceutical composition comprises, for example, (a) an agent that blocks FGFR signaling through FRS2; and, (b) one or more pharmaceutically acceptable excipients or salts. The skeletal deformity may be a craniosynostosis syndrome and/or a skeletal dysplasia condition.

Another aspect of the invention provides a method for treating an individual having a cancer characterized by abnormal FGFR activity, comprising administering to the individual a therapeutically effective amount of at least one therapeutic agent that antagonizes FGFR signaling through FRS2.

The (therapeutic) agent of the invention can be used to treat cancers, such as: bladder cancer, cervical carcinoma, breast cancer, pancreatic adenocarcinoma, prostate cancer, malignant astrocytoma, transitional cell carcinoma of the bladder, thyroid carcinoma, or multiple myeloma.

BRIEF DESCRIPTION OF THE DRAWINGS

FIGS. 7A and 7B show targeted activation of the Fgfr2c transcriptional alternative. (7A) Genomic structure and targeting events; exons are shaded, with the exon number above and the protein domain name underneath. X and Y, 3' and internal probe, respectively. (7B) DNA sequence of the region used for site-directed mutagenesis, showing the C342Y mutation and the newly formed RsaI site. B, BamHI; H, HindIII; RI, EcoRI; S, SacI; TM, transmembrane exon; #, site of point mutation.

FIG. 8 (top panel) shows the skeletal structure of wt and heterozygote harboring the Cys342Tyr knock-in transgene. The arrow points to the characteristic shortened face, and slightly rounded and domed cranium skull seen in Crouzon disease individuals. The lower left panel compares the head phenotypes of the wt (left) and Cys342Tyr heterozygotes (right). The lower right panel shows the skull phenotype of $Fgfr2^{C342Y/+}$ heterozygote littermates at postnatal day 29 (P29). Arrows point to the obliterated coronal and fused lambdoid sutures, with multiple bone inserts.

DETAILED DESCRIPTION OF THE INVENTION

I. Overview

Figure 1:
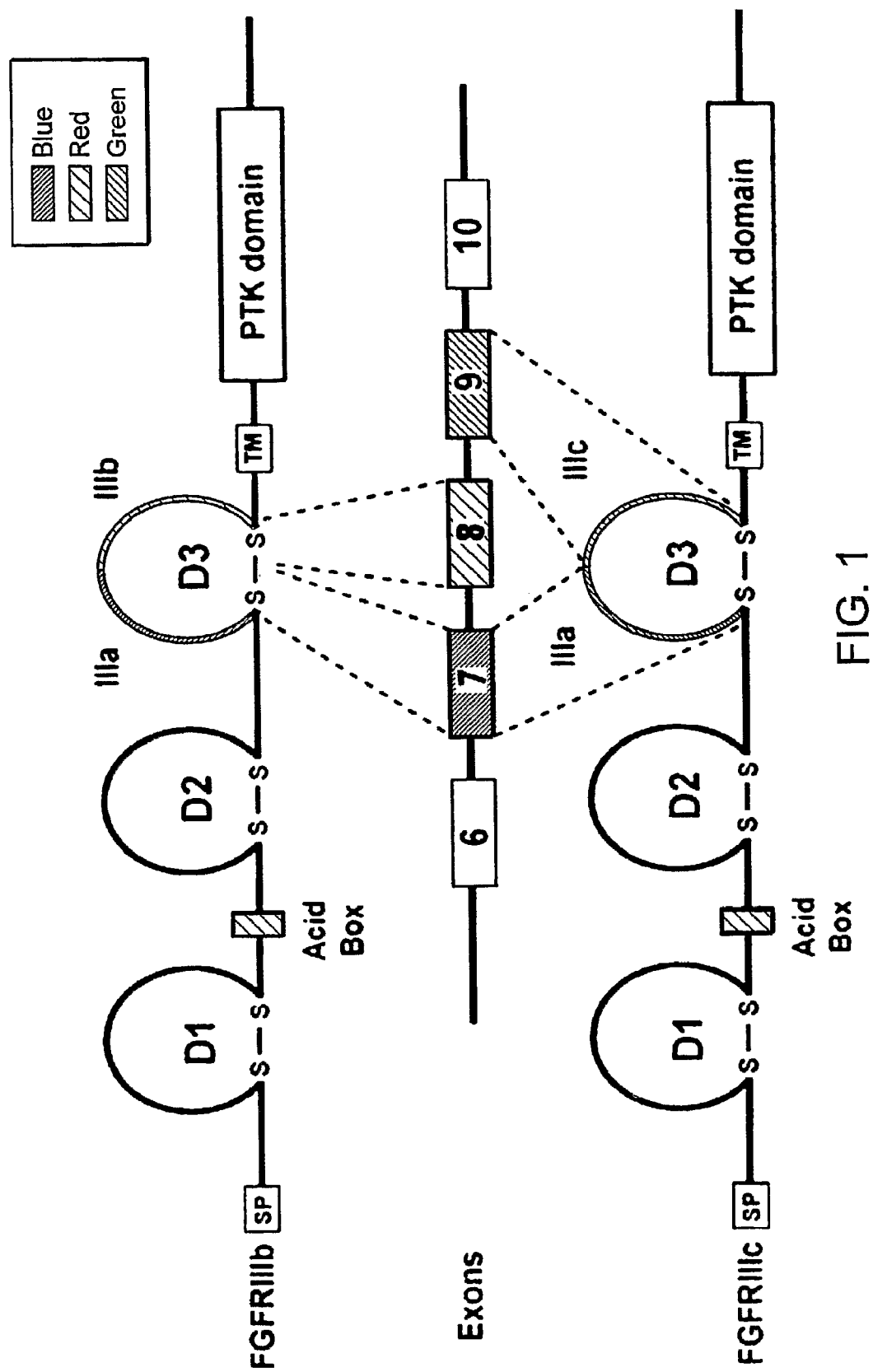
FIG. 1 shows various FGFR isoforms generated by alternative splicing of FGFR transcripts. The two forms of FGFR are generated by alternative splicing of exons 8 and 9. The C-terminal half of D3 is encoded by exon 8 to generate the FGFR-IIIb isoform while the C-terminal half of D3 is encoded by exon 9 to generate the FGFR-IIIc isoform.

The present invention is partially based on the discovery that FRS2-mediated FGFR signaling can be selectively/specifically abolished by abolishing productive interaction between FRS2 and FGFR, even without substantially affecting other FGFR downstream signaling, such as Shp2 and/or PLCγ signalings.

The invention relates to methods of altering, such as interfering with, the signaling (e.g., interaction and/or phosphorylation, etc.) between FGF receptor (FGFR) and one of its downstream signaling molecules, FRS2. In one embodiment, the present invention is a method of interfering with or reducing FRS2-mediated cell signal transduction, in which cells are contacted with an agent (also referred to as a drug) which interferes with FGFR-FRS2 function, under conditions under which the agent enters the cells. This can be carried out, for example, by contacting cells with an agent that interferes with interactions between the PTB domain of FRS2 and the juxtamembrane domain of FGFR2 and/or reduces phosphorylation of FRS2. The invention further relates to methods of reducing in an individual the severity of a skeletal deformity caused by a gain of function mutation in FGFR. Such methods are useful in preventing, treating, and/or alleviating (e.g., reducing the severity of) conditions, such as a number of closely related skeletal defects, especially in craniofacial regions and limbs extremities, resulting from abnormal (e.g. excessive) FRS2-mediated FGFR signaling, in a mammal, such as a human.

The invention also provides a method for screening for or identifying agents that antagonize FGFR signaling through FRS2, comprising: (1) forming a reaction mixture including FGFR and FRS2, under conditions under which the FGFR activates FRS2, (2) contacting the reaction mixture with a test agent, and (3) determining the effect of the test agent for one or more activities selected from the group consisting of: (a) a decrease in the interaction between FGFR and FRS2; (b) a decrease in the expression of FGFR and/or FRS2; (c) a decrease in the phosphorylation of FRS2 by FGFR, or increase in the de-phosphorylation of FRS2 at residues phosphorylated by FGFR; (d) a decrease in the half-life or stability, or increase in the degradation of FGFR and/or FRS2; (e) where the reaction mixture is a whole cell, a changed subcellular localization of FGFR and/or FRS2; (f) a decrease in the abundance of the FGFR-FRS2 complex; (g) a decrease in the expression level and/or activity of a gene downstream of FGFR-FRS2 signaling; wherein a positive observation in any of (a)-(g) is indicative that the test agent is an antagonist of FGFR signaling through FRS2.

The invention also provides the use of such identified agents/compounds as pharmaceutical compositions to treat individuals who have or are at risk of developing conditions characterized by abnormal (e.g. excessive) FRS2-mediated FGFR signaling.

Various agents may be used to either generically, or specifically or selectively disrupt this branch of the FGFR signaling without globally affecting the other branches of FGFR signaling. Such agents may be polypeptides (e.g. competitive binding domain peptides, etc.) or antibodies that disrupt FRS2-FGFR interaction, polynucleotides (e.g. anti-sense polynucleotides, or RNAi constructs, such as siRNA constructs targeting FRS2 and/or FGF2), ribozymes, DNA enzymes, or small molecule antagonists or peptidomimetics, etc. Details of each category of agents are described below in a separate section.

Another aspect of the current invention is partially based on the discovery that attenuating or abolishing FRS2-mediated FGFR signaling (e.g. FRS2α-mediated FGFR2IIIc signaling) can reduce the severity, or even completely suppress the mutant phenotype associated with certain abnormally active FGFRs. These abnormally active FGFRs have been implicated in a variety of mammalian craniosynostosis syndromes and/or skeletal dysplasia conditions, such as Crouzon syndrome, Apert syndrome, Jackson-Weiss syndrome, Pfeiffer syndrome, Crouzon+acanthosis nigricans, Beare-Stevenson cutis gyrata, non-syndromic craniosynostosis (NS), Muenke syndrome, Saethre-Chotzen-like syndrome, Achondroplasia (ACH), SADDEN (severe achondroplasia with developmental delay and acanthosis nigricans), Thanatophoric dysplasia type I (TDI), Thanatophoric dysplasia type II (TDII), or Hypochondroplasia (HCH).

For example, as described herein, Applicants have shown that a constitutively active C342Y mutation in FGFR2c, which is frequently seen in the human Crouzon syndrome, causes Crouzon-like phenotypes in a mouse model. However, such mutant phenotypes are almost completely suppressed if the mutant FGFR2c receptor additionally contains a second mutation in the intracellular domain important for FRS2 binding and activation (but not Shc or PLCγ activation).

Thus, the instant invention provides a method for treating an individual, such as a human, having a craniosynostosis syndrome and/or skeletal dysplasia condition resulting from abnormal (e.g. excessive) FGFR activity, comprising administering to the individual a therapeutically effective amount of at least one therapeutic agent that antagonizes FGFR signaling through FRS2.

The agent of the invention may exert its inhibitory effect by, for example, inhibiting the interaction between FGFR and FRS2; inhibiting the expression of FGFR and/or FRS2; inhibiting the phosphorylation of FRS2 by FGFR, or increasing the de-phosphorylation of FRS2 at residues phosphorylated by FGFR; decreasing the half-life or stability, or increasing the degradation of FGFR and/or FRS2; altering the proper subcellular localization of FGFR and/or FRS2; decreasing the abundance of the FGFR-FRS2 complex; and/or decreasing the expression level and/or activity of a gene downstream of FGFR-FRS2 signaling. Various exemplary categories of agents of the invention are described in Section II in detail.

The methods of the invention may be used to treat a number of craniosynostosis syndromes and/or skeletal dysplasia conditions resulting from abnormal FGFR activity. In certain embodiments, the abnormal FGFR activity is excessive FGFR activity. In certain embodiments, the excessive FGFR activity results from a constitutively activating mutation in the FGFR. In certain embodiments, the constitutively activating mutation promotes ligand-independent FGFR dimerization. In certain embodiments, the ligand-independent FGFR dimerization is effectuated by destabilizing the D3 immunoglobulin (Ig) like domain of the FGFR, and disrupting the normal intramolecular disulfide bond of the D3 Ig-like domain. In certain embodiments, the disruption of D3 intramolecular disulfide bond results from the mutation of at least one of the two conserved Cys residues normally involved in intramolecular disulfide bond formation in the D3 Ig-like domain. In certain embodiments, the conserved Cys corresponding to FGFR2 Cys-342 is mutated. In certain embodiments, the disruption of D3 intramolecular disulfide bond results from destabilizing mutations in residues other than the two conserved Cys residues normally involved in intramolecular disulfide bond formation in the D3 Ig-like domain. In certain embodiments, the ligand-independent FGFR dimerization is effectuated by intermolecular disulfide bond formation within the transmembrane region of FGFR. In certain embodiments, the excessive FGFR activity results from a mutant FGFR with relaxed ligand-receptor specificity. In certain embodiments, the mutant FGFR comprises one or both mutations in the two highly conserved residues in the linker connecting the D2 and D3 Ig-like domains in FGFR, wherein the two highly conserved residues correspond to Ser-252 and Pro-253 of FGFR2. In certain embodiments, the excessive FGFR activity results from gain-of-function mutations in the catalytic RTK (Receptor Tyrosine Kinase) domain of FGFR, said RTK domain exhibiting enhanced activity in a ligand-independent manner.

An agent of the invention can affect FGFR, FRS2, their downstream signaling molecules, or combination thereof. In the instances in which an agent has both anti-FGFR and anti-FRS2 activity, only a single agent needs to be administered to the individual. Two or more agents (e.g., one or more for FGFR, plus one or more for FRS2, etc.) can be administered according to the method of present invention.

As used herein, the term "agent" or "therapeutic agent" is a generic term which include any compound or molecule (agent) which blocks FGFR signaling through the FRS2 pathway. For example, such (therapeutic) agents can inhibit functions (activity or expression) of the target genes/proteins, the interaction of the target protein with each other and/or with their binding partners, the posttranslational modification (e.g. phosphorylation, myristylation, etc.) of the target proteins, or any of the downstream signaling events. For example, such (therapeutic) agents can inhibit functions (activity or expression) of FGFR and/or FRS2, inhibit the interaction of FGFR and FRS2 with each other and/or with their other binding partners (e.g. FGF, other adaptor proteins binding FRS2, etc.), inhibit the phosphorylation of FRS2 by FGFR, or inhibit any of the downstream signaling events upon activation of the FGFR-FRS2 pathway (e.g. after binding of FGF ligands to FGFR, or phosphorylation of FRS2 by constitutively active FGFR, etc.). Generally, substances that act as antagonists of FGFR and/or FRS2 may be used as the subject agents, which may include, but are not limited to, a protein, a peptide, a small organic molecule (e.g. with a molecular weight of no more than about 5000 Da, or 4000 Da, or 3000 Da, 2000 a, 1000 Da, 500 Da, 300 Da, or 100 Da), a peptidomimetic, an antibody, and a nucleic acid.

"Inhibition of gene expression" refers to the absence (or observable decrease) in the level of protein and/or mRNA product from a target gene. "Specificity" refers to the ability to inhibit the target gene without manifest effects on other genes of the cell. The consequences of inhibition can be confirmed by examination of the outward properties of the cell or organism (as presented below in the examples) or by biochemical techniques, such as RNA solution hybridization, nuclease protection, Northern hybridization, reverse transcription, gene expression monitoring with a microarray, antibody binding, enzyme linked immunosorbent assay (ELISA), Western blotting, radioimmunoassay (RIA), other immunoassays, and fluorescence activated cell analysis (FACS).

In certain embodiments, the agent of the invention is formulated with a pharmaceutically acceptable carrier.

As used herein the term "patient," "individual," or "subject" to be treated by the method of the invention can mean either a human or a non-human animal. A patient/an individual may have already manifested certain disease symptoms (such as Crouzon syndrome), or may be asymptomatic at present, but pre-disposed or of high risk of developing such disease symptoms in the future. The predisposition/high risk may be assessed based on genetic counseling, genotyping (of the patient/individual or individual's relatives), etc., either before or after the individual is born.

As described above, the agent blocks signaling through the target gene pathways (e.g. FGFR-FRS2 pathway), for example, by inhibiting the interaction between the target proteins with each other and/or their binding partners, inhibiting gene expression of the target genes, inhibiting activity of the target proteins, inhibiting clustering of the target proteins, inhibiting posttranslational modification of the target proteins, or inhibiting any downstream signaling event of the target proteins.

The term "blocking/inhibiting/antagonizing . . . pathway" includes both specific and general blocking/inhibiting/antagonizing. For example, FGFR-FRS2 signaling may be specifically blocked by disrupting the interaction between FGFR and FRS2. It may also be generally blocked by inhibiting/attenuating the kinase activity of FGFR, thereby attenuating/inhibiting all FGFR downstream signaling.

"Overexpression" generally means having a higher expression level than the "normal" level in "normal" cells. The quantitation of expression level of mRNA and/or protein can be done using routine methods well-known in the art, such as Northern and Western blots, or commercial kits. It also includes expression of FGFR at a place (tissue, organ, etc.) that normally does not express FGFR, or a specific type of FGFR.

Yet another aspect of the present invention provides use of the subject therapeutic agents in the manufacture of medicament for the treatment of a craniosynostosis syndrome and/or skeletal dysplasia condition resulting from abnormal FGFR activity. As described above, the subject (therapeutic) agent(s) block signaling through the target genes, for example, by inhibiting the interaction between the target protein with their binding partners or with each other, by inhibiting gene expression, activity, clustering, or posttranslational modification (e.g. phosphorylation), inhibiting any downstream signaling events, etc.

Yet another aspect of the invention provides a method to treat certain cancer characterized by abnormal (e.g. excessive) FGFR activity, comprising administering to the individual a therapeutically effective amount of at least one therapeutic agent that antagonizes FGFR signaling (e.g., FGFR signaling through FRS2).

Constitutive activation of tyrosine kinases as fusion proteins with other genes due to chromosomal translocations, or overexpression of certain otherwise normal kinases plays important role in the development of many malignancies. For example, germ line mutations that are associated with achondroplasia and thantophoric dysplasia are associated with 35% of cases of bladder cancer and 25% of cases of cervical carcinoma (Cappellen et al, *Nat Genet.* 23: 18-20, 1999). Yoshimura et al. reported the overexpression and localization of fibroblast growth factor-1 (FGF-1) and FGF receptor-1 (FGFR-1) in human breast cancer (*Clin Immunol Immunopathol* 89: 28-34, 1998). Abnormal expression of FGFR1 and FGFR4 are associated with pancreatic adenocarcinoma (Kobrin et al., *Cancer Res* 53: 4741-4744, 1993; Shah et al., *Oncogene* 21: 8251-8261, 2002). Class switching of FGFR from IIIb isoform to IIIc isoform, and abnormal expression of FGFR1c in prostate epithelial cells are linked to prostate cancer (Kwabi-Addo et al., *Prostate* 46: 163-172, 2001). Elevated expression of FGFR1 in white matter is seen in malignant astrocytoma (Yamaguchi et al., *Proc Natl Acad Sci USA* 91: 484-488, 1994). Transitional cell carcinoma of the bladder frequently contains certain FGFR3 mutations (Arg248Cys; Ser249Cys; Gly372Cys; Lys652Glu) (Kimura et al., *Cancer* 92: 2555-2561, 2001; Sibley et al., *Oncogene* 20: 4416-4418, 2001; and van Rhijn et al., *Cancer Res* 61: 1265-1268, 2001). Thyroid carcinoma has been found to overexpress FGFR3 (Onose et al., *Eur J Endocrinol* 140: 169-173, 1999). In addition, activating mutations of FGFR3 (Lys650Glu; Lys650Met) associated with chromosomal translocation t(4:14) (p16.3; q32.3) have been reported in multiple myeloma (Chesi et al., *Nat Genet.* 16: 260-264, 1997). Numerous other FGFR3 mutations have also been associated with a large number of other human cancers.

Thus the instant invention may be used to disrupt FGFR downstream signaling, such as those through FRS2, thereby preventing, alleviating, eliminating some or all symptoms associated with such cancers.

II. FGFR and/or FRS2 Agents

As used herein, the FGFR/FRS2 agents of the present invention include any compound (agent) which (generally or specifically) blocks the FGFR-FRS2 signaling. For example, such agents can inhibit functions (activity or expression), interactions between FGFR/FRS2 and their other binding partners, or phosphorylation of FRS2 by the FGFR, or inhibit any of the downstream signaling events (such as Ras-MAPK, Shp2, PI-3K pathways, etc.) upon binding/phosphorylation of FRS2 by FGFR. Generally, any substances that act as antagonists of FGFR and/or FRS2 (and their relevant downstream targets) may be used as the subject agents. Such agents include, but are not limited to, a protein, a peptide, a small organic molecule, a peptidomimetic, an antibody, and a nucleic acid (e.g., antisense, nucleic acid, RNAi (including siRNA or vectors expressing siRNA), etc.). The following subsections describe the various categories of the subject agents.

A. Polypeptides and Antibodies

In certain aspects, the subject agents include a polypeptide which is a mutated form, a mimic or a fragment of FGFR or FRS2 protein. Such agents can bind to FRS2 or FGFR, respectively, and prevent the productive interaction between FGFR and FRS2, or to their other binding partners (such as Grb2, Shc, etc.).

For example, the subject agents may include a soluble polypeptide having the amino acid sequence of the intracellular domain/juxtamembrane domain of FGFR that normally binds FRS2 (such as including the region comprising residues L424, R426, and/or V428 of FGFR2, etc.), or a soluble polypeptide having the amino acid sequence of the PTB domain of FRS2. Such soluble polypeptides may be further derived, using art-recognized means, as peptidomimetics with better (e.g. longer) serum half-life, better stability, and/or better membrane permeability, etc. Since the ligand binding region of FGFR and FRS2 are known or can be readily determined using art-recognized techniques (such as in vitro binding assay using fragments of the receptors and the natural ligands), such dominant negative mutated form, mimic or fragments can be readily made without undue experimentation.

In another example, antagonists which comprise the extracellular domain of FGFR but do not possess clustering activity, can be produced as FGFR (therapeutic) agents. Optionally, such FGFR (therapeutic) agents may be a fusion (hybrid) protein. For example, the extracellular domain of FGFR may be fused to the Fc domain of human IgG. Non-clustered forms of these hybrid proteins act as antagonists and thus can be used to reduce the possibility of autodimerization between mutant FGFRs.

In certain aspects, the subject agents can be antibodies, such as antibodies that are specifically reactive with FGFR, FRS2, or both. Antibodies may be polyclonal or monoclonal; intact or truncated, e.g., F(ab')2, Fab, Fv; xenogeneic, allogeneic, syngeneic, or modified forms thereof, such as humanized or chimeric antibodies. Alternatively, these antibodies may be encoded by polynucleotides, and expressed upon transfection of such polynucleotides into the target cell. These antibodies or fragments thereof may bind the surface receptors, and antagonize receptor function by receptor internalization, thereby attenuating the signaling of even constitutively active receptors. Alternatively, immune system of the host may recognize and eliminate such Ab-engaged cells, through, for example, natural killer cells (NK cells).

By using immunogens derived from an FGFR, a FRS2 polypeptide, or from both, anti-protein/anti-peptide antisera or monoclonal antibodies can be made by standard protocols (see, for example, Antibodies: A Laboratory Manual ed. by Harlow and Lane (Cold Spring Harbor Press: 1988)). A mammal, such as a mouse, a hamster or rabbit can be immunized with an immunogenic form of the peptide (e.g., a polypeptide or an antigenic fragment which is capable of eliciting an antibody response, or a fusion protein). Techniques for conferring immunogenicity on a protein or peptide include conjugation to carriers or other techniques well known in the art. A full-length or an immunogenic portion of an FGFR polypeptide a FRS2 polypeptide can be administered in the presence of adjuvant. The progress of immunization can be monitored by detection of antibody titers in plasma or serum. Standard ELISA or other immunoassays can be used with the immunogen as antigen to assess the levels of antibodies. In one embodiment, antibodies of the invention are specific for the extracellular portion of the FGFR or FRS2 protein. In another embodiment, antibodies of the invention are specific for the intracellular portion or the transmembrane portion of the FGFR and/or FRS2 protein.

Following immunization of an animal with an antigenic preparation of an FGFR polypeptide or a FRS2 polypeptide or both, antisera can be obtained and, if desired, polyclonal antibodies can be isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, Nature 256: 495-497, 1975), the human B cell hybridoma technique (Kozbar et al., Immunology Today 4: 72, 1983), and the EBV-hybridoma technique to produce human monoclonal antibodies (Cole et al., Monoclonal Antibodies and Cancer Therapy, Alan R. Liss, Inc. pp. 77-96, 1985). Hybridoma cells can be screened immunochemically for production of antibodies specifically reactive with an FGFR and/or FRS2 polypeptide and monoclonal antibodies isolated from a culture comprising such hybridoma cells.

The term antibody as used herein is intended to include fragments thereof which are also specifically reactive with an FGFR polypeptide, or a FRS2 polypeptide. Antibodies can be fragmented using conventional techniques and the fragments screened for utility in the same manner as described above for whole antibodies. For example, F(ab)$_2$ fragments can be generated by treating antibody with pepsin. The resulting F(ab)$_2$ fragment can be treated to reduce disulfide bridges to produce Fab fragments. An antibody of the present invention is further intended to include bispecific, single-chain, and chimeric and humanized molecules having affinity for an FGFR polypeptide or FRS2 polypeptide conferred by at least one CDR region of the antibody. Techniques for the production of single chain antibodies (U.S. Pat. No. 4,946,778) can also be adapted to produce single chain antibodies. Also, transgenic mice or other organisms including other mammalian species, may be used to express humanized antibodies. In certain embodiments, the antibodies further comprises a label attached thereto and able to be detected (e.g., the label can be a radioisotope, fluorescent compound, enzyme or enzyme co-factor).

In certain specific embodiments, an antibody of the invention is a monoclonal antibody, and in certain embodiments the invention makes available methods for generating novel antibodies. For example, a method for generating a monoclonal antibody that binds specifically to an FGFR polypeptide or FRS2 polypeptide may comprise administering to a mouse an amount of an immunogenic composition comprising the FGFR polypeptide or FRS2 polypeptide effective to stimulate a detectable immune response, obtaining antibody-producing cells (e.g., cells from the spleen) from the mouse and fusing the antibody-producing cells with myeloma cells to obtain antibody-producing hybridomas, and testing the antibody-producing hybridomas to identify a hybridoma that produces a monocolonal antibody that binds specifically to the FGFR or FRS2 polypeptide. Once obtained, a hybridoma can be propagated in a cell culture, optionally in culture conditions where the hybridoma-derived cells produce the monoclonal antibody that binds specifically to the FGFR or FRS2 polypeptide. The monoclonal antibody may be purified from the cell culture.

In addition, the techniques used to screen antibodies in order to identify a desirable antibody may influence the properties of the antibody obtained. For example, an antibody to be used for certain therapeutic purposes may be able to target an antigen on a particular cell type, as opposed to antigen in solution. Accordingly, to obtain antibodies of this type, it may be desirable to screen for antibodies that bind to cells that express the antigen of interest (e.g., by fluorescence activated cell sorting), or at least confirm that the antibody can bind to FGFR or FRS2. A variety of different techniques are available for testing antibody:antigen interactions to identify particularly desirable antibodies. Such techniques include ELISAs, surface plasmon resonance binding assays (e.g. the Biacore binding assay, Bia-core AB, Uppsala, Sweden), sandwich assays (e.g. the paramagnetic bead system of IGEN International, Inc., Gaithersburg, Md.), Western blots, immunoprecipitation assays and immunohistochemistry.

B. Polynucleotides/Nucleic Acids

In certain aspects, the agents of the present invention comprise a nucleic acid. As used herein, the term "nucleic acid" refers to polynucleotides such as deoxyribonucleic acid (DNA), and, where appropriate, ribonucleic acid (RNA). The term should also be understood to include, as applicable to the embodiment being described, single-stranded (such as sense or antisense) and double-stranded polynucleotides.

In one embodiment, the invention relates to the use of antisense nucleic acid complementary to polynucleotides encoding FGFR, FRS2, or their downstream signaling polypeptides or variants thereof, to decrease expression of FGFR, FRS2, and/or the signaling protein (e.g. Ras-MAPK, Shp2, PI-3K, etc.). Such an antisense nucleic acid can be delivered, for example, as an expression plasmid which, when transcribed in the cell, produces RNA which is complementary to at least a unique portion of the cellular mRNA which encodes an FGFR, FRS2, or downstream signaling polypeptide. Alternatively, the construct is an oligonucleotide (DNA or RNA) which is generated ex vivo and which, when introduced into the cell causes inhibition of expression by hybridizing with the mRNA and/or genomic sequences encoding an FGFR, FRS2, or downstream signaling polypeptide. Such oligonucleotides are optionally modified oligonucleotide which are resistant to endogenous nucleases, e.g., exonucleases and/or endonucleases, and is therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in nucleic acid therapy have been reviewed, for example, by van der Krol et al. (*Biotechniques* 6: 958-976, 1988); and Stein et al. (*Cancer Res* 48: 2659-2668, 1988).

In another embodiment, the invention relates to the use of RNA interference (RNAi) to affect knockdown of FGFR encoding nucleic acid (gene), FRS2 encoding nucleic acid (gene), or downstream signaling polypeptide encoding nucleic acid (gene). RNAi constructs comprise double stranded RNA that can specifically block expression of a target gene. RNAi provides a useful method of inhibiting gene expression in vitro or in vivo. RNAi constructs can comprise either long stretches of dsRNA identical or substantially identical to the target nucleic acid sequence or short stretches of dsRNA identical or substantially identical to only a region of the target nucleic acid sequence.

As used herein, the term "RNAi construct" is a generic term including small interfering RNAs (siRNAs), hairpin RNAs, and other RNA species which can be cleaved in vivo to form siRNAs. RNAi constructs herein also include expression vectors (also referred to as RNAi expression vectors) capable of giving rise to transcripts which form dsRNAs or hairpin RNAs in cells, and/or transcripts which can produce siRNAs in vivo.

Optionally, the RNAi constructs contain a nucleotide sequence that hybridizes under physiologic conditions of the cell to the nucleotide sequence of at least a portion of the mRNA transcript for the gene to be inhibited (i.e., the "target" gene). The double-stranded RNA need only be sufficiently similar to natural RNA that it mediate RNAi under the conditions used (such as physiological condition). Thus, the RNAi construct can include sequence variations that might be expected due to genetic mutation, strain polymorphism or evolutionary divergence. The number of tolerated nucleotide mismatches between the target sequence and the RNAi construct sequence is no more than 1 in 5 basepairs, or 1 in 10 basepairs, or 1 in 20 basepairs, or 1 in 50 basepairs. Mismatches in the center of the siRNA duplex are most critical and may essentially abolish cleavage of the target RNA. In contrast, nucleotides at the 3' end of the siRNA strand that is complementary to the target RNA do not significantly contribute to specificity of the target recognition. Sequence identity may be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the target gene is desirable. Alternatively, the duplex region of the RNA may be defined functionally as a nucleotide sequence that is capable of hybridizing with a portion of the target gene transcript (e.g., 400 mM NaCl, 40 mM PIPES pH 6.4, 1 mM EDTA, 50° C. or 70° C. hybridization for 12-16 hours; followed by washing).

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., *Molecular Cloning: A Laboratory Manual*, Second Edition (1989) Cold Spring Harbor Laboratory Press, Cold Spring Harbor, N.Y.). The conditions of temperature and ionic strength determine the "stringency" of the hybridization. For preliminary screening for homologous nucleic acids, low stringency hybridization conditions, corresponding to a $T_m$ (melting temperature) of 55° C., can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SSC. High stringency hybridization conditions correspond to the highest $T_m$, e.g., 50% formamide, 5× or 6×SSC. SSC is a 0.15M NaCl, 0.015M Na-citrate. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50-9.51). For hybridization with shorter nucleic acids, i.e., oligonucleotides, the position of mismatches becomes more important, and the length of the oligonucleotide determines its specificity (see Sambrook et al., supra, 11.7-11.8). A minimum length for a hybridizable nucleic acid is at least about 10 nucleotides; in certain embodiments, it is at least about 15 nucleotides; and in other embodiments, the length is at least about 20 nucleotides.

Unless specified, the term "standard hybridization conditions" refers to a $T_m$ of about 55° C., and utilizes conditions as set forth above. In a specific embodiment, the $T_m$ is 60° C.; in an alternative embodiment, the $T_m$ is 65° C. In a specific embodiment, "high stringency" refers to hybridization and/or washing conditions at 68° C. in 0.2×SSC, at 42° C. in 50% formamide, 4×SSC, or under conditions that afford levels of hybridization equivalent to those observed under either of these two conditions.

Suitable hybridization conditions for oligonucleotides (e.g., for oligonucleotide probes or primers) are typically somewhat different than for full-length nucleic acids (e.g., full-length cDNA), because of the oligonucleotides' lower melting temperature. Because the melting temperature of oligonucleotides will depend on the length of the oligonucleotide sequences involved, suitable hybridization temperatures will vary depending upon the oligonucleotide molecules used. Exemplary temperatures may be 37° C. (for 14-base oligonucleotides), 48° C. (for 17-base oligonucleotides), 55° C. (for 20-base oligonucleotides) and 60° C. (for 23-base oligonucleotides). Exemplary suitable hybridization conditions for oligonucleotides include washing in 6×SSC/0.05% sodium pyrophosphate, or other conditions that afford equivalent levels of hybridization.

The double-stranded structure may be formed by a single self-complementary RNA strand or two complementary RNA strands. RNA duplex formation may be initiated either inside or outside the cell. The RNA may be introduced in an amount which allows delivery of at least one copy per cell. Higher doses (e.g., at least 5, 10, 100, 500 or 1000 copies per cell) of double-stranded material may yield more effective inhibition, while lower doses may also be useful for specific applications. Inhibition is sequence-specific in that nucleotide sequences corresponding to the duplex region of the RNA are targeted for genetic inhibition.

The subject RNAi constructs can be "small interfering RNAs" or "siRNAs." These nucleic acids are from about 19 to about 30 nucleotides in length, and in specific embodiments 19-23 or 21-23 nucleotides in length. The siRNAs are understood to recruit nuclease complexes and guide the complexes to the target mRNA by pairing to the specific sequences. As a result, the target mRNA is degraded by the nucleases in the protein complex. In a particular embodiment, the 21-23 nucleotides siRNA molecules comprise a 3' hydroxyl group. In certain embodiments, the siRNA constructs can be generated by processing of longer double-stranded RNAs, for example, in the presence of the enzyme dicer. In one embodiment, the *Drosophila* in vitro system is used. In this embodiment, dsRNA is combined with a soluble extract derived from *Drosophila* embryo, thereby producing a combination. The combination is maintained under conditions in which the dsRNA is processed to RNA molecules of from about 19 to about 23 nucleotides or from about 19 to about 23 nucleotides or from about 21 to about 23 nucleotides. The siRNA molecules can be purified using a number of techniques known to those of skill in the art. For example, gel electrophoresis can be used to purify siRNAs. Alternatively, non-denaturing methods, such as non-denaturing column chromatography, can be used to purify the siRNA. In addition, chromatography (e.g., size exclusion chromatography), glycerol gradient centrifugation, affinity purification with antibody can be used to purify siRNAs.

Production of RNAi constructs can be carried out by chemical synthetic methods or by recombinant nucleic acid techniques. Endogenous RNA polymerase of the treated cell may mediate transcription in vivo, or cloned RNA polymerase can be used for transcription in vitro. The RNAi constructs may include modifications to either the phosphate-sugar backbone or the nucleoside, e.g., to reduce susceptibility to cellular nucleases, improve bioavailability, improve formulation characteristics, and/or change other pharmacokinetic properties. For example, the phosphodiester linkages of natural RNA may be modified to include at least one of an nitrogen or sulfur heteroatom. Modifications in RNA structure may be tailored to allow specific genetic inhibition while avoiding a general response to dsRNA. Likewise, bases may be modified to block the activity of adenosine deaminase. The RNAi construct may be produced enzymatically or by partial/ total organic synthesis, any modified ribonucleotide can be introduced by in vitro enzymatic or organic synthesis. Methods of chemically modifying RNA molecules can be adapted for modifying RNAi constructs (see, e.g., Heidenreich et al. *Nucleic Acids Res* 25: 776-780, 1997; Wilson et al., *J Mol Recog* 7: 89-98, 1994; Chen et al., *Nucleic Acids Res* 23: 2661-2668, 1995; Hirschbein et al., *Antisense Nucleic Acid Drug Dev* 7: 55-61, 1997). Merely to illustrate, the backbone of an RNAi construct can be modified with phosphorothioates, phosphoramidate, phosphodithioates, chimeric methylphosphonate-phosphodiesters, peptide nucleic acids, 5-propynyl-pyrimidine containing oligomers or sugar modifications (e.g., 2'-substituted ribonucleosides, a-configuration).

In some cases, at least one strand of the siRNA molecules has a 3' overhang of from about 1 to about 6 nucleotides in length, although may be from 2 to 4 nucleotides in length. In certain embodiments, the 3' overhangs are 1-3 nucleotides in length. In certain embodiments, one strand has a 3' overhang and the other strand is blunt-ended or also has an overhang. The length of the overhangs may be the same or different for each strand. In order to further enhance the stability of the siRNA, the 3' overhangs can be stabilized against degradation. In one embodiment, the RNA is stabilized by including purine nucleotides, such as adenosine or guanosine nucleotides. Alternatively, substitution of pyrimidine nucleotides by modified analogues, e.g., substitution of uridine nucleotide 3' overhangs by 2'-deoxythyinidine is tolerated and does not affect the efficiency of RNAi. The absence of a 2' hydroxyl significantly enhances the nuclease resistance of the overhang in tissue culture medium and may be beneficial in vivo.

The RNAi construct can also be in the form of a long double-stranded RNA. In certain embodiments, the RNAi construct is at least 25, 50, 100, 200, 300 or 400 bases. In certain embodiments, the RNAi construct is 400-800 bases in length. The double-stranded RNAs are digested intracellularly, e.g., to produce siRNA sequences in the cell. However, use of long double-stranded RNAs in vivo is not always practical, presumably because of deleterious effects which may be caused by the sequence-independent dsRNA response. In such embodiments, the use of local delivery systems and/or agents which reduce the effects of interferon or PKR may be desirable.

Alternatively, the RNAi construct is in the form of a hairpin structure (named as hairpin RNA). The hairpin RNAs can be synthesized exogenously or can be formed by transcribing from RNA polymerase III promoters in vivo. Examples of making and using such hairpin RNAs for gene silencing in mammalian cells are described in, for example, Paddison et al., *Genes Dev* 16: 948-58, 2002; McCaffrey et al., *Nature* 418: 38-39, 2002; McManus et al., *RNA* 8: 842-850, 2002; Yu et al., *Proc Natl Acad Sci USA* 99: 6047-6052, 2002). In certain embodiments, such hairpin RNAs are engineered in cells or in an animal to ensure continuous and stable suppression of a desired gene. It is known in the art that siRNAs can be produced by processing a hairpin RNA in the cell.

PCT application WO 01/77350 describes an exemplary vector for bi-directional transcription of a transgene to yield both sense and antisense RNA transcripts of the same transgene in a eukaryotic cell. Accordingly, in certain embodiments, the present invention provides a recombinant vector having the following unique characteristics: it comprises a viral replicon having two overlapping transcription units arranged in an opposing orientation and flanking a transgene for an RNAi construct of interest, wherein the two overlapping transcription units yield both sense and antisense RNA transcripts from the same transgene fragment in a host cell.

The siRNAs or expression constructs can be constructed by PCR, and the PCR products can then be directly transfected into mammalian cells, resulting in functional expression of siRNAs. This approach should prove useful for identification of other optimal siRNA-target combinations and for multiplexing siRNA expression in mammalian cells.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein. Alternatively, "Host cell" means any cell of any organism that is selected, modified, transformed, grown or used or manipulated in any way for the production of a substance by the cell. For example, a host cell may be one that is manipulated to express a particular gene, a DNA or RNA sequence, a protein or an enzyme. Host cells may be cultured in vitro or one or more cells in a non-human animal (e.g., a transgenic animal or a transiently transfected animal).

C. Ribozymes

In another embodiment, the invention relates to the use of ribozyme molecules designed to catalytically cleave an mRNA transcript to prevent translation of mRNA (see, e.g., PCT International Publication WO90/11364, published Oct. 4, 1990; Sarver et al., 1990, Science 247:1222-1225; and U.S. Pat. No. 5,093,246). While ribozymes that cleave mRNA at site-specific recognition sequences can be used to destroy particular mRNAs, the use of hammerhead ribozymes may be useful or desirable. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, 1988, Nature, 334:585-591. The ribozymes of the present invention also include RNA endoribonucleases (hereinafter "Cech-type ribozymes") such as the one which occurs naturally in *Tetrahymena thermophila* (known as the IVS or L-19 IVS RNA) and which has been extensively described (see, e.g., Zaug, et al., 1984, Science, 224:574-578; Zaug and Cech, 1986, Science, 231:470-475; Zaug, et al., 1986, Nature, 324:429-433; published International patent application No. WO88/04300 by University Patents Inc.; Been and Cech, *Cell* 47: 207-216, 1986).

D. DNA Enzymes

In a further embodiment, the invention relates to the use of DNA enzymes to inhibit expression of the target genes (e.g. FGFR, FRS2, and/or downstream genes). DNA enzymes incorporate some of the mechanistic features of both antisense and ribozyme technologies. DNA enzymes are designed so that they recognize a particular target nucleic acid sequence, much like an antisense oligonucleotide. However much like ribozymes, they are catalytic and specifically cleave the target nucleic acid. Briefly, to design DNA enzyme that specifically recognizes and cleaves a target nucleic acid, one of skill in the art must first identify the unique target sequence. In certain embodiments, the unique or substantially unique target sequence is a G/C rich sequence of approximately 18 to 22 nucleotides. High G/C content helps insure a stronger interaction between the DNA enzyme and the target sequence. When synthesizing the DNA enzyme, the specific antisense recognition sequence that will target the enzyme to the message is divided so that it comprises the two arms of the DNA enzyme, and the DNA enzyme loop is placed between the two specific arms. Methods of making and administering DNA enzymes can be found, for example, in U.S. Pat. No. 6,110,462.

E. Small Molecule Antagonists/Peptidomimetics

In certain aspects, the agents of the present invention include a small molecule (e.g., a peptidomimetic). Examples of small molecules include, but are not limited to, small peptides or peptide-like molecules (e.g., a peptidomimetic). As used herein, the term "peptidomimetic" includes chemically modified peptides and peptide-like molecules that contain non-naturally occurring amino acids, peptoids, and the like. Peptidomimetics provide various advantages over a peptide, including enhanced stability when administered to a subject. Methods for identifying a peptidomimetic are well known in the art and include the screening of databases that contain libraries of potential peptidomimetics. For example, the Cambridge Structural Database contains a collection of greater than 300,000 compounds that have known crystal structures (Allen et al., *Acta Crystallogr. Section B* 35: 2331, 1979). Where no crystal structure of a target molecule is available, a structure can be generated using, for example, the program CONCORD (Rusinko et al., *J. Chem. Inf Comput. Sci.* 29: 251, 1989). Another database, the Available Chemicals Directory (Molecular Design Limited, Informations Systems; San Leandro Calif.), contains about 100,000 compounds that are commercially available and also can be searched to identify potential peptidomimetics of CCL21 or a chemokine receptor.

As described herein, small molecule compounds may encompass numerous chemical classes, although typically they are organic molecules. In some embodiments, the small organic compounds have molecular weights of more than 50 and less than about 2,500 daltons. Candidate agents comprise functional groups necessary for structural interaction with proteins, particularly hydrogen bonding, and typically include at least an amine, carbonyl, hydroxyl, sulfhydryl or carboxyl group. Candidate small molecule compounds can be obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant, and animal extracts are available or readily produced. Additionally, natural or synthetically produced libraries and compounds can be modified through conventional chemical, physical, and biochemical means. Known pharmacological agents may be subjected to directed or random chemical modifications, such as acylation, alkylation, esterification, and amidification, to produce structural analogs.

In certain aspects, the subject agents can be drugs that disrupt the normal subcellular localization of FGFR and/or FRS2. The two members of the FRS2 family, FRS2α and FRS2β, are structurally very similar. Each is composed of an N-terminal myristylation signal, and FRS2 has been localized in caveolae-like membrane domains at the cell surface, which is at least partly due to its N-terminal myristylation. Thus any inhibitor that prevents myristylation (such as RNAi agent of the myristylation enzyme) can prevent the correct subcellular localization of FRS2, thereby attenuating/eliminating the FGFR-FRS2 signaling.

Figure 14B:
FIGS. 14A-D show pharmacological intervention in FGFR activation. (C) Structure of [4-(3,5-difluorophenyl)-1H-pyrrolo[2,3-b]pyridin-3-yl](3-methoxyphenyl)methanone (PLX052). (D) 3T3-cells treated for 5 minutes with PLX052 were ligand stimulated for 5 minutes at 37° C. Cell lysates were subjected to immunoprecipitation with anti-FLAG tag antibodies (the expression vector contains a tag in the c-terminus of FGFR2) followed by immunoblotting with either anti-phosphotyrosine (pTyr) or anti-FLAG antibodies. (A & B) Crystals of the apo-FGFR1 minimal kinase domain were grown at 4° C. by vapor diffusion in hanging drops containing 2 uL of 12 mg/mL protein solution and 2 uL of reservoir solution: 16% PEG8K, 0.25 M (NH$_4$)$_2$SO$_4$, 5% ethylene glycol, 10 mM DTT, and 0.1 M Bis Tris, pH 5.8. Native crystals were soaked overnight at 4° C. in mother liquor containing 2 mM PLX052 and 5% DMSO. Complexed crystal belongs to monoclinic space group C2 and has unit cell dimensions a=211.9 Å, b=49.7 Å, c=66.2 Å, and β=107.4°. One cryo-cooled crystal was used for data collection, and data was collected at beamline X26 at Brookhaven National Laboratory. Co-crystallization of the kinase with PLX052 was also performed and found the same structural result. (B) Molecular surface representation of FGFR1K, reveals inhibitor, PLX052, bound in a cleft between the two lobes of the kinase. The nucleotide binding loop is shown in blue, the hinge region in magenta, and the catalytic core in yellow. (A) The side chains that interact with PLX052. Carbon atoms of the kinase and inhibitor are gray and green, respectively, oxygen atoms are red, and nitrogen atoms are blue. Solid lines depict hydrogen bonds. Coloring of the backbone is as in (B).
Figure 14D:
Figure 14A:
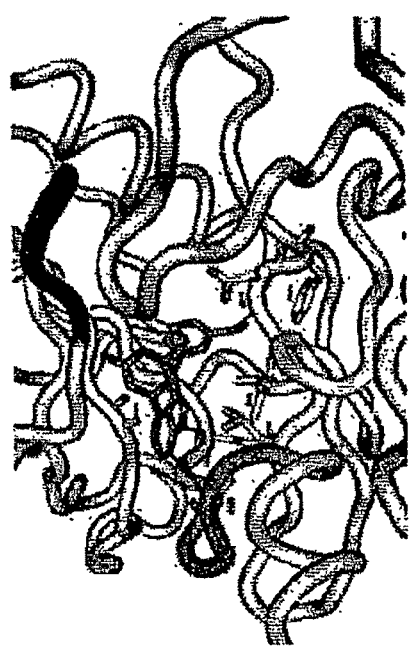
Figure 14C:
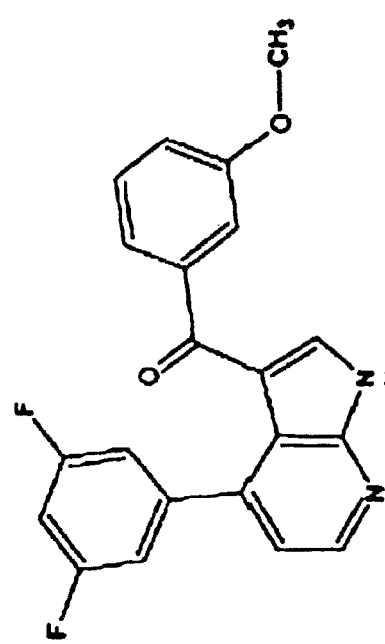

In certain aspects, the subject agents are 3-benzoyl-7-azaindole compounds, such as PLX052 (see FIG. 14C and below).

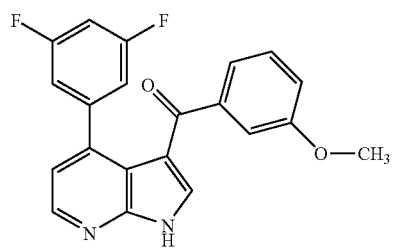

Such compounds may be substituted with one or more groups selected from nitro, cyano, hydroxyl, thiol, carboxyl, sulfate, or substituted or unsubstituted amino, alkoxy, alkylamino, alkylthio, hydroxyalkyl, alkoxyalkyl, aminoalkyl, thioalkyl, ether, thioether, ester, amide, thioester, carbonate, carbamate, urea, sulfonate, sulfone, sulfoxide, sulfonamide, alkyl, alkenyl, alkynyl, acyl, acyloxy, acylamino, aryl, heteroaryl, carbocyclyl, heterocyclyl, aralkyl, hetaralkyl, carbocyclylalkyl, and heterocyclylalkyl. In particular, the present 3-benzoyl-7-azaindole compounds may be substituted with one or more polar or ionic groups, which may increase aqueous solubility. For example, the 3-benzoyl-7-azaindole compounds may be substituted with one or more groups selected from nitro, cyano, hydroxyl, thiol, carboxyl, sulfate, or substituted or unsubstituted amino, alkoxy, alkylamino, hydroxyalkyl, alkoxyalkyl, aminoalkyl, ether, ester, amide, carbonate, carbamate, urea, sulfonate, sulfone, sulfoxide, sulfonamide, acyl, acyloxy, and acylamino.

The present invention also contemplates agents obtainable from the screening methods described below.

III. Drug Screening Assays

There are numerous approaches to screening for the subject agents in treating a craniosynostosis syndrome and/or skeletal dysplasia condition resulting from abnormal FGFR activity. In a typical experiment, the method comprises: (1) forming a reaction mixture including FGFR and FRS2, under a condition where the FGFR activates FRS2, (2) contacting the reaction mixture with a test agent, and (3) determining the effect of the test agent for one or more activities selected from the group consisting of: (a) a decrease in the interaction between FGFR and FRS2; (b) a decrease in the expression of FGFR and/or FRS2; (c) a decrease in the phosphorylation of FRS2 by FGFR, or increase in the de-phosphorylation of FRS2 at residues phosphorylated by FGFR; (d) a decrease in the half-life or stability, or increase in the degradation of FGFR and/or FRS2; (e) where the reaction mixture is a whole cell, a changed subcellular localization of FGFR and/or FRS2; (f) a decrease in the abundance of the FGFR-FRS2 complex; (g) a decrease in the expression level and/or activity of a gene downstream of FGFR-FRS2 signaling, wherein a positive observation in any of (a)-(g) is indicative that the test agent is an antagonist of FGFR signaling through FRS2.

In one embodiment, the method further comprises verifying for the absence of substantial effect of the test agent on FGFR signaling independent of FRS2. This would ensure that the effect of the test agent on FGFR-FRS2 signaling is specific for FRS2. However, as indicated above, even a general inhibitor of FGFR signaling may be beneficial for the treatment of the craniofacial diseases and cancers.

For example, high-throughput screening of compounds or molecules can be carried out in the subject in vitro calvario culture to identify agents or drugs that exhibit inhibitory effect. Test agents to be assessed for their anti-growth effects can be any chemical (element, molecule, compound, drug), made synthetically, made by recombinant techniques or isolated from a natural source. For example, test agents can be peptides, polypeptides, peptoids, sugars, hormones, or nucleic acid molecules (such as antisense or RNAi nucleic acid molecules). In addition, test agents can be small molecules or molecules of greater complexity made by combinatorial chemistry, for example, and compiled into libraries. These libraries can comprise, for example, alcohols, alkyl halides, amines, amides, esters, aldehydes, ethers and other classes of organic compounds. Test agents can also be natural or genetically engineered products isolated from lysates or growth media of cells—bacterial, animal or plant—or can be the cell lysates or growth media themselves. Presentation of test compounds to the test system can be in either an isolated form or as mixtures of compounds, especially in initial screening steps.

Alternatively, an assay can be carried out to screen for compounds that specifically inhibit binding of the target protein pairs (e.g. FGFR and FRS2), or their binding to other downstream signaling molecules. Compounds identified through this screening can then be tested in animal models of the subject invention to assess their therapeutic activity in vivo.

In one embodiment of an assay to identify a substance that interferes with interaction of target proteins (e.g. FGFR and/or FRS2) or with their other binding partners, samples of cells expressing target protein 1, or samples of immobilized target protein 1, are contacted with labeled target protein 2 (e.g., full-length, or a soluble portion thereof, or a fusion protein such as a fusion of the extracellular domain and the Fc domain of IgG), at the presence or absence of a test compound (or group of test compounds). The amount of labeled target protein 2 which has bound to the cells/immobilized target protein 1 is determined. A lesser amount of label (where the label can be, for example, a radioactive isotope, a fluorescent or colormetric label) in the sample contacted with the test compound(s) is an indication that the test compound(s) interferes with binding.

An assay to identify a substance which interferes with interaction between a target protein with its binding partner can be performed with the component (e.g., cells, purified protein, including fusion proteins and portions having binding activity) which is not to be in competition with a test compound, linked to a solid support. The solid support can be any suitable solid phase or matrix, such as a bead, the wall of a plate or other suitable surface (e.g., a well of a microtiter plate), column pore glass (CPG) or a pin that can be submerged into a solution, such as in a well. Linkage of cells or purified protein to the solid support can be either direct or through one or more linker molecules.

In one embodiment, an isolated or purified protein (e.g., an FGFR and/or FRS2) can be immobilized on a suitable affinity matrix by standard techniques, such as chemical cross-linking, or via an antibody raised against the isolated or purified protein, and bound to a solid support. The matrix can be packed in a column or other suitable container and is contacted with one or more compounds (e.g., a mixture) to be tested under conditions suitable for binding of the compound to the protein. For example, a solution containing compounds can be made to flow through the matrix. The matrix can be washed with a suitable wash buffer to remove unbound compounds and non-specifically bound compounds. Compounds which remain bound can be released by a suitable elution buffer. For example, a change in the ionic strength or pH of the elution buffer can lead to a release of compounds. Alternatively, the elution buffer can comprise a release component or components designed to disrupt binding of compounds (e.g., one or more ligands or receptors, as appropriate, or analogs thereof which can disrupt binding or competitively inhibit binding of test compound to the protein).

Fusion proteins comprising all of, or a portion of, a protein (e.g., an FGFR and/or FRS2) linked to a second moiety not occurring in that protein as found in nature can be prepared for use in another embodiment of the method. Suitable fusion proteins for this purpose include those in which the second moiety comprises an affinity ligand (e.g., an enzyme, antigen, epitope). The fusion proteins can be produced by inserting the protein (e.g., an FGFR and/or FRS2) or a portion thereof into a suitable expression vector which encodes an affinity ligand. The expression vector can be introduced into a suitable host cell for expression. Host cells are disrupted and the cell material, containing fusion protein, can be bound to a suitable affinity matrix by contacting the cell material with an affinity matrix under conditions sufficient for binding of the affinity ligand portion of the fusion protein to the affinity matrix.

In one aspect of this embodiment, a fusion protein can be immobilized on a suitable affinity matrix under conditions sufficient to bind the affinity ligand portion of the fusion protein to the matrix, and is contacted with one or more compounds (e.g., a mixture) to be tested, under conditions suitable for binding of compounds to the receptor or ligand protein portion of the bound fusion protein. Next, the affinity matrix with bound fusion protein can be washed with a suitable wash buffer to remove unbound compounds and non-specifically bound compounds without significantly disrupting binding of specifically bound compounds. Compounds which remain bound can be released by contacting the affinity matrix having fusion protein bound thereto with a suitable elution buffer (a compound elution buffer). In this aspect, compound elution buffer can be formulated to permit retention of the fusion protein by the affinity matrix, but can be formulated to interfere with binding of the compound(s) tested to the receptor or ligand protein portion of the fusion protein. For example, a change in the ionic strength or pH of the elution buffer can lead to release of compounds, or the elution buffer can comprise a release component or components designed to disrupt binding of compounds to the receptor or ligand protein portion of the fusion protein (e.g., one or more ligands or receptors or analogs thereof which can disrupt binding of compounds to the receptor or ligand protein portion of the fusion protein). Immobilization can be performed prior to, simultaneous with, or after contacting the fusion protein with compound, as appropriate. Various permutations of the method are possible, depending upon factors such as the compounds tested, the affinity matrix selected, and elution buffer formulation. For example, after the wash step, fusion protein with compound bound thereto can be eluted from the affinity matrix with a suitable elution buffer (a matrix elution buffer). Where the fusion protein comprises a cleavable linker, such as a thrombin cleavage site, cleavage from the affinity ligand can release a portion of the fusion with compound bound thereto. Bound compound can then be released from the fusion protein or its cleavage product by an appropriate method, such as extraction.

In other embodiments, other assays can be used for screening for compounds that decrease the expression level (protein or nucleic acid) of the target gene pairs. Methods of detecting and optionally quantitating proteins can be achieved by techniques such as antibody-based detection assays. In these cases, antibodies may be used in a variety of detection techniques, including enzyme-linked immunosorbant assays (ELISAs), immunoprecipitations, and Western blots. On the other hand, methods of detecting and optionally quantitating nucleic acids generally involve preparing purified nucleic acids and subjecting the nucleic acids to a direct detection assay or an amplification process followed by a detection assay. Amplification may be achieved, for example, by polymerase chain reaction (PCR), reverse transcriptase (RT), and coupled RT-PCR. Detection of nucleic acids is generally accomplished by probing the purified nucleic acids with a probe that hybridizes to the nucleic acids of interest, and in many instances, detection involves amplification as well. Northern blots, dot blots, microarrays, quantitative PCR, and quantitative RT-PCR are all well known methods for detecting nucleic acids.

In some cases, one or more compounds can be tested simultaneously. Where a mixture of compounds is tested, the compounds selected by the foregoing processes can be separated (as appropriate) and identified by suitable methods (e.g., PCR, sequencing, and chromatography). Large combinatorial libraries of compounds (e.g., organic compounds, peptides, nucleic acids) produced by combinatorial chemical synthesis or other methods can be tested (see e.g., Ohlmeyer, M. H. J. et al., *Proc. Natl. Acad. Sci. USA* 90: 10922-10926, 1993, and DeWitt, S. H. et al., *Proc. Natl. Acad. Sci. USA* 90: 6909-6913, 1993, relating to tagged compounds; see also, Rutter, W. J. et al., U.S. Pat. No. 5,010,175; Huebner, V. D. et al., U.S. Pat. No. 5,182,366; and Geysen, H. M., U.S. Pat. No. 4,833,092). Where compounds selected from a combinatorial library by the present method carry unique tags, identification of individual compounds by chromatographic methods is possible. Where compounds do not carry tags, chromatographic separation, followed by mass spectrophotometry to ascertain structure, can be used to identify individual compounds selected by the method, for example.

IV. Methods of Inhibition or Treatment

The invention relates to methods of altering, such as interfering with, the signaling (e.g., interaction and/or phosphorylation, etc.) between FGF receptor (FGFR) and one of its downstream signaling molecules, FRS2. In one embodiment, the present invention is a method of interfering with or reducing FRS2-mediated cell signal transduction, in which cells are contacted with an agent (also referred to as a drug) which interferes with FGFR-FRS2 function, under conditions under which the agent enters the cells. This can be carried out, for example, by contacting cells with an agent that interferes with interactions between the PTB domain of FRS2 and the juxtamembrane domain of FGFR2 and/or reduces phosphorylation of FRS2. The invention further relates to methods of reducing in an individual the severity of a skeletal deformity caused by a gain of function mutation in FGFR. Such methods are useful in preventing, treating, and/or alleviating (e.g., reducing the severity of) conditions, such as a number of closely related skeletal defects, especially in craniofacial regions and limbs extremities, resulting from abnormal (e.g. excessive) FRS2-mediated FGFR signaling, in a mammal, such as a human.

In certain embodiments, the present invention provides methods of inhibiting FRS2 interaction with and/or phosphorylation by FGFR in a cell, comprising contacting the cell with an agent that blocks FRS2 interaction with and/or phosphorylation by FGFR, under conditions under which the agent enters the cell. The agent may block the FRS2-mediated FGFR signaling specifically or selectively (e.g., without substantially affecting other FRS2-independent FGFR signaling, such as through Shp2 and/or PLCγ). Alternatively, the agent may block the FRS2-mediated FGFR signaling non-specifically by, for example, globally down-regulating FGFR expression or kinase activity.

In certain embodiments, the agent is provided to the cell as a solution in contact with the cell. The agent may enter the cell through passive diffusion, and/or active transport. Certain agents, such as small peptides, antisense or RNAi polynucleotides may be expressed inside the cell from a vector introduced into the cell.

In certain embodiments, the present invention provides methods of preventing, treating, or alleviating (e.g., reduce the severity of) certain symptoms in an individual suffering from a craniosynostosis syndrome and/or skeletal dysplasia condition resulting from abnormal FGFR activity, through administering to the individual a therapeutically effective amount of the subject agent as described above. In other embodiments, the invention provides methods of preventing or reducing the onset of such conditions in an individual through administering to the individual a therapeutically effective amount of a subject agent. These methods are particularly aimed at therapeutic and prophylactic treatments of animals, and more particularly, humans.

In certain embodiments of such methods, one or more agents can be administered, together (simultaneously) or at different times (sequentially). In addition, the agents can be administered with another type of compounds for treating such conditions. The two types of compounds may be administered simultaneously or sequentially.

In certain embodiments, gene therapy may be applicable with the use of nucleic acids encoding the subject therapeutic polypeptides (for example, fragments of FGFR and/or FRS2, see below). Alternatively, an antisense nucleic acid or an RNAi construct can be used for reducing or inhibiting expression of the subject gene pairs.

Craniosynostosis syndrome is generally treated during the first year of birth. In most cases, between 3 to six months and then few procedures are carried out up to the age of 12 or so (by then the growth of the brain is almost complete). There are numerous centers in the US that currently carry out the surgical procedures for craniosynostosis. Thus in one embodiment, treatment for the various craniosynostosis syndromes and/or skeletal dysplasia conditions are commenced no later than the period when surgical prevention can still be beneficial (e.g. no later than 3-6 months after birth). In other embodiments, treatments may commence even before the fetus is born. And treatments may continue throughout the life of the individual if necessary, but can stop when the skull development is largely complete (e.g. about 10-15 years).

The following describes certain skeletal deformity conditions, e.g., craniosynostosis syndrome and/or skeletal dysplasia condition, that may be treated by the agents of the invention, including Crouzon syndrome, Apert syndrome, Jackson-Weiss syndrome, Pfeiffer syndrome, Crouzon+ acanthosis nigricans, Beare-Stevenson cutis gyrata, non-syndromic craniosynostosis (NS), Muenke syndrome, Saethre-Chotzen-like syndrome, Achondroplasia (ACH), SADDEN (severe achondroplasia with developmental delay and acanthosis nigricans), Thanatophoric dysplasia type I (TDI), Thanatophoric dysplasia type II (TDII), or Hypochondroplasia (HCH).

The first fibroblast growth factor (FGF) was discovered as a mitogen for cultured fibroblasts (Gospodarowicz, *Nature* 249: 123-127, 1974). Since then, at least 22 distinct FGFs have been identified in a variety of organisms from nematode and *Drosophila* to mouse and human (reviewed in Ornitz and Itoh, *Genome Biol* 2: 3005, 2001). Although, FGFs vary in size from 17 to 34 kDa, all members of the family share a conserved sequence of 120 amino acids that show 16-65% sequence identity (Ornitz and Itoh, supra). FGFs mediate a variety of cellular responses during embryonic development and in the adult organism. During embryonic development, FGFs play a critical role in morphogenesis by regulating cell proliferation, differentiation and cell migration. In the adult organism, FGFs play an important role in the control of the nervous system, in tissue repair, wound healing and in tumor angiogenesis (reviewed in Givol et al., Molecular and cellular biology of FGF signaling. In: C. J. Epstein, R. P. Erickson and A. Wynshaw-Boris, Editors, *Inborn errors of development—the molecular basis of clinical disorders of morphogenesis*, Oxford University Press, Oxford (2003), pp. 367-379).

FGFs mediate their cellular responses by binding to and activating a family of four receptor tyrosine kinases (RTKs) (Lee et al., *Science* 245: 57-60, 1989; Givol and Yayon, *FASEB J* 6: 3362-3369, 1992; Jaye et al., *Biochim Biophys Acta* 1135: 185-199, 1992) designated the high-affinity FGF-receptors FGFR1-FGFR4. FGFs also bind to heparin or heparan sulfate proteoglycans (HSPG), low-affinity receptor that do not transmit a biological signal but rather function as an accessory molecule that regulate FGF-binding and the activation of the occupied signaling receptors (Yayon et al., *Cell* 64: 841-848, 1991; Rapraeger et al., *Science* 252: 1705-1708, 1991; Ornitz et al., *Mol Cell Biol* 12: 240-247, 1992; Spivak-Kroizman et al., *Cell* 79: 1015-1024, 1994; and Lin et al., *Development* 126: 3715-3723, 1999). Like all receptor tyrosine kinases, the four signaling FGFR1-FGFR4 are composed of an extracellular ligand-binding domain, a single transmembrane domain and a cytoplasmic domain containing the catalytic protein tyrosine kinase core as well as additional regulatory sequences (Hunter, *Cell* 100: 113-127, 2000; and Schlessinger, *Cell* 103: 211-225, 2000). The extracellular ligand-binding domain of FGFR is composed of three immunoglobulin (Ig) like domains, designated D1-D3; a stretch of seven to eight acidic residues in the linker connecting D1 and D2, designated the "acid box" and a conserved positively charged region in D2 that serves as a binding site for heparin (Schlessinger et al., *Mol Cell* 6: 743-750, 2000).

An important hallmark of the FGFR family of RTKs is that a variety of FGFR isoforms are generated by alternative splicing of FGFR transcripts. The different FGFR isoforms include FGFR with an extracellular domain composed of either two or three Ig-like domains, soluble secreted FGFR forms as well as alternative splicing in the third Ig-like domain (D3) that profoundly alters ligand-binding specificity (Miki et al., *Proc Natl Acad Sci USA* 89: 246-250, 1992; and Yayon et al., *EMBO J* 11: 1885-1890, 1992). The alternative splicing in D3 exists in FGFR1, 2 and 3, but not in FGFR4. It has been shown that exon 7 of FGFR2 gene encodes for the N-terminal half of D3 (designated 'a'), while exons 8 and 9 alternatively encode for the C-terminal half of D3 and are thus designated as 'b' and 'c' forms of FGFR, respectively (FIG. 1). The two alternative forms display different ligand-binding characteristics. Furthermore, it has been shown that the FGFR2b isoform is exclusively expressed in epithelial cells (also designated as KGFR), and that the FGFR2c is expressed exclusively in mesenchymal cells (Orr-Urtreger et al., *Dev Biol* 158: 475-486, 1993). The lineage-specific expression of the IIIb and IIIc isoforms of FGFRs enables interaction between the epithelial and mesenchymal layers during development in response to different FGFs.

The biological roles of more than half of the 22 known mammalian FGFs have been investigated by targeting the genes of individual FGFs by homologous recombination. The results, as presented in Tables 2 and 3 of Eswarakumar et al. (*Cytokine & Growth Factor Reviews* 16(2): 139-149, 2005, incorporated herein by reference) summarizes the phenotypes caused by targeted disruption of 15 out of the 22 FGFs, and FGFR1-FGFR4, respectively.

Signaling via FGFRs is mediated via direct recruitment of signaling proteins that bind to tyrosine auto-phosphorylation sites on the activated receptor and via closely linked docking proteins that become tyrosine phosphorylated in response to FGF-stimulation and form a complex with additional complement of signaling proteins. The cytoplasmic domain of FGFR contains in addition to the catalytic PTK core, several regulatory sequences. The juxtamembrane domain of FGFRs is considerably longer than that of other receptor tyrosine kinases. This region contains a highly conserved sequence that serves as a binding site for the phosphotyrosine binding (PTB) domains of the two members of the FRS2 family of docking proteins FRS2α and FRS2β (Ong et al., *Mol Cell Biol* 20: 979-989, 2000; and Dhalluin et al., *Mol Cell*

Figure 2:
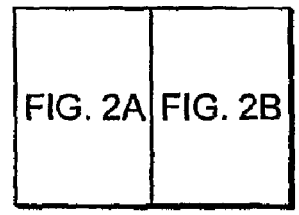
FIG. 2 (left panel) is a wiring diagram depicting signaling pathways downstream of FGFR, including the various signaling pathways that are dependent upon tyrosine phosphorylation of FRS2α following FGF-stimulation (lines with arrow ends, representing activation or agonism). The negative signals that are mediated by or impinge upon FRS2α are marked by lines with "T-shaped" ends (representing inhibition or antagonism). Also shown, heterologous control of FGF-signaling by growth factors (i.e. insulin, EGF) or G-protein coupled agonists (i.e. LPA, carbachol) that stimulate threonine phosphorylation of FRS2α. The right panel shows the domain structure of an FGFR2 monomer, including the autoinhibition Ig-like domain D1, the acid box, the Ig-like domains D2 and D3 responsible for FGF binding (including the heparin binding site on D2), the transmembrane region, and the intracellular PTK domain. The regions of the intracellular domain responsible for downstream signaling through FRS2, Shc, and PLCγ, respectively, are also indicated.
Figure 2A:
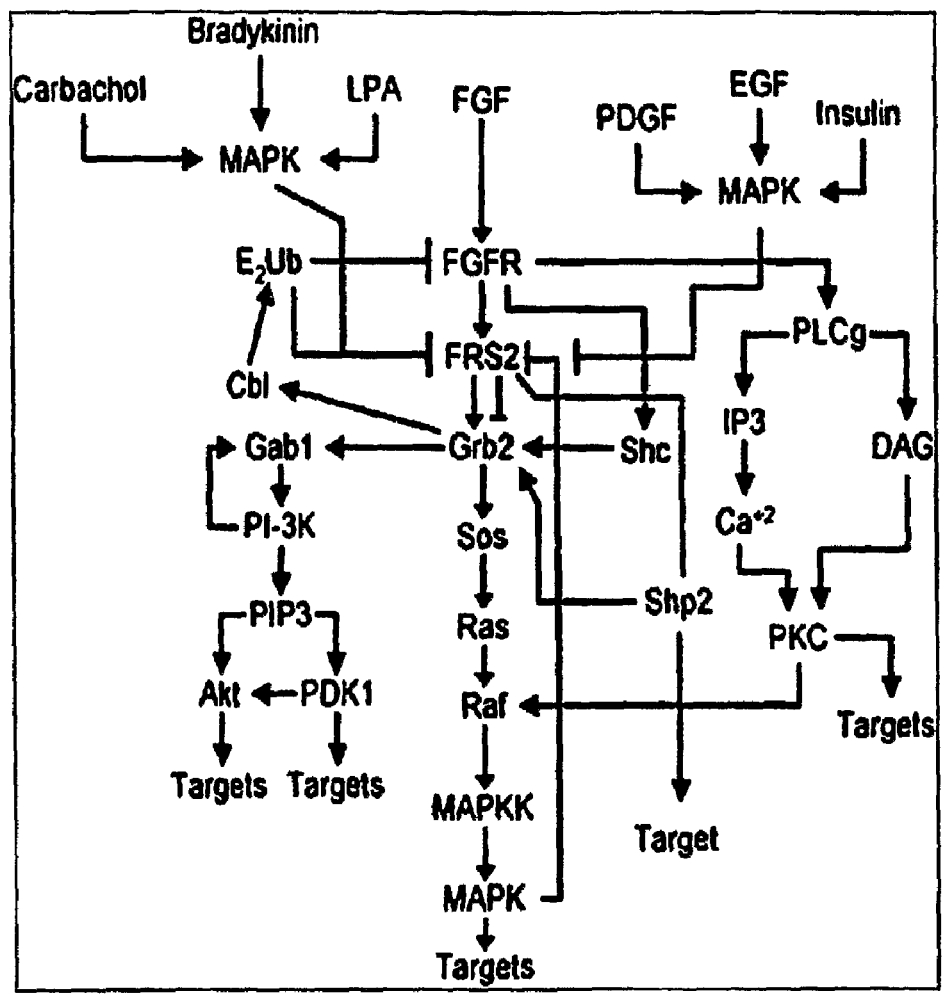
Figure 2B:
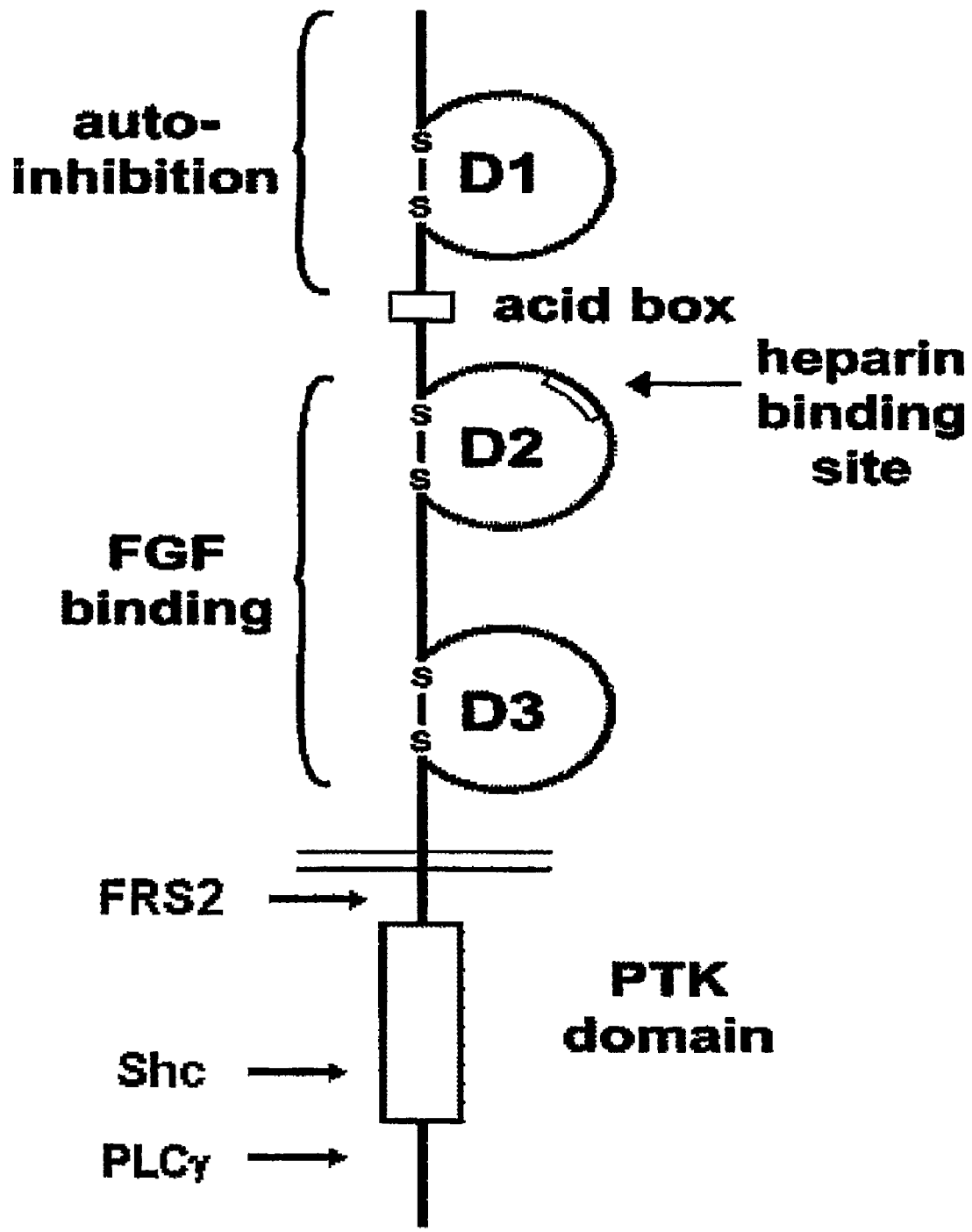
Figure 3:
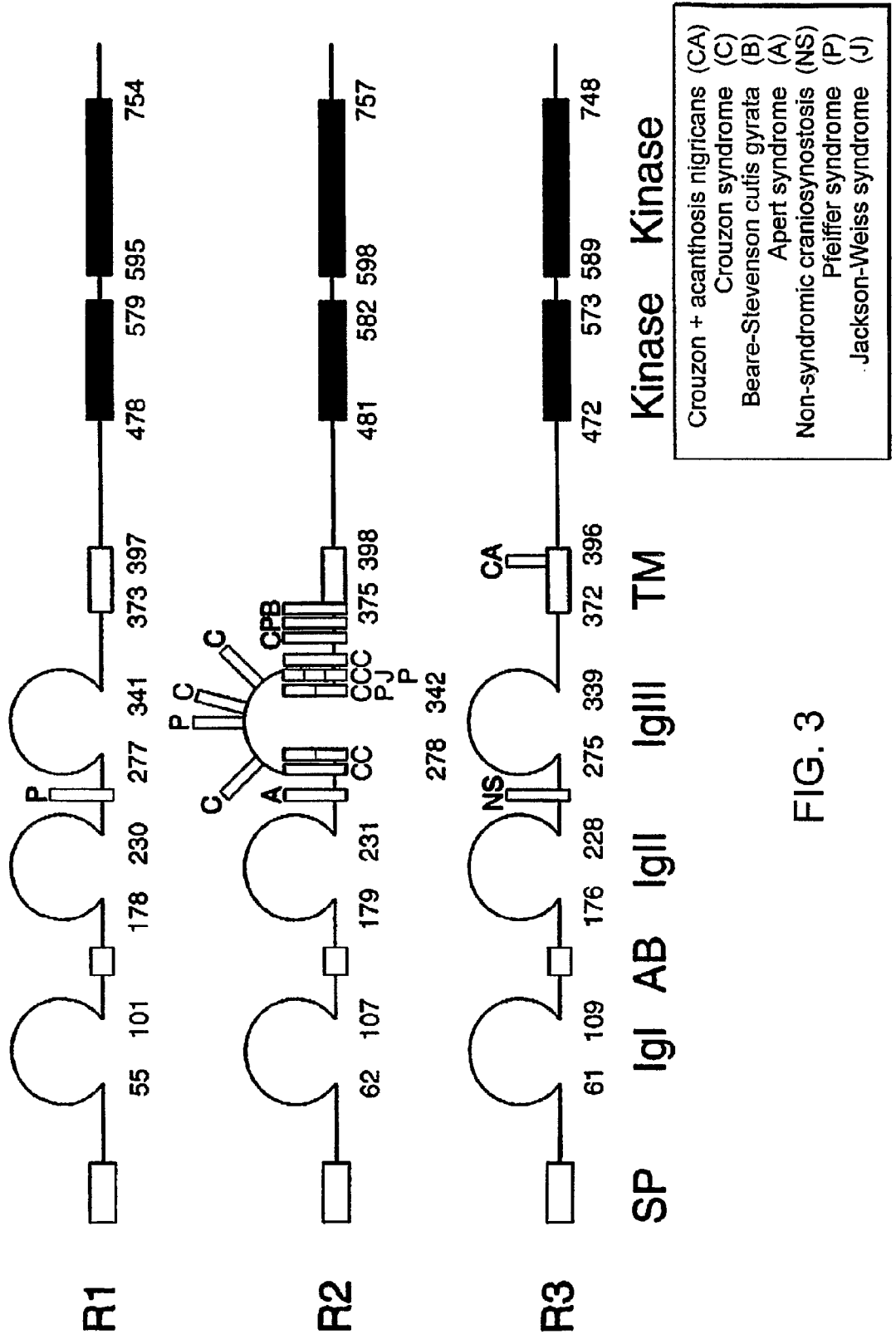
FIG. 3 is a schematic drawing showing the three FGFR isoforms (designated R1, R2, and R3, respectively). The numbers below the depicted domain structures represent the approximate begin/end of each domains. Various diseases associated with FGFR mutations are listed in the boxes below (with abbreviations). The vertical bars represent the approximate positions of the mutations associated with the respective diseases.

6: 921-929, 2000). While the PTB domain of FRS2α or FRS2β binds to FGFR1 constitutively, independent of ligand stimulation and tyrosine phosphorylation, the same PTB domains bind to the juxtamembrane domain of NGF-receptor (TrkA) in a phosphorylation dependent manner to a canonical PTB domain-binding site (NPXpY motif). The tyrosine kinase domain of FGFRs is split like that of platelet-derived growth factor (PDGF) receptor or stem cell growth factor receptor (SCFR designated c-Kit), but the kinase insert region is much shorter in FGFRs than that of PDGFR and c-Kit. Autophosphorylation on Tyr766 in the carboxy terminal tail of FGFR1 creates a specific-binding site for the SH2 domain of phospholipase Cγ (PLCγ) (Mohammadi et al., *Mol Cell Biol* 11: 5068-5078, 1991). Mutational analysis of Y766 has shown that the phosphorylation of this tyrosine residue is essential for complex formation with and tyrosine phosphorylation of PLCγ (Mohammadi et al., *Nature* 358: 681-684, 1992), resulting in PLCγ activation, stimulation of phosphatidylinositol (PI) hydrolysis and the generation of the two second messengers, diacylglycerol and Ins(1,4,5)P$_3$. Membrane recruitment of PLCγ is aided by binding of the Pleckstrin homology (PH) domain of PLCγ to PtdIns (3,4,5) P$_3$ molecules that are generated in response to PI-3 kinase stimulation (Falasca et al., *EMBO J* 17: 414-422, 1998). A mutant FGFR1 in which Y766 is replaced by phenylalanine is unable to activate PI hydrolysis and Ca$^{2+}$ release in response to FGP-stimulation suggesting that PI hydrolysis is dispensible for FGF-induced mitogenic stimulation of cultured cells. However, analysis of "knock-in" mice with mutated Y766 have shown that this tyrosine is required for a negative regulatory signal during anteroposterior patterning of mouse embryos (Partanen et al., *Genes Dev* 12: 2332-2344, 1998). FIG. 2 depicts the various signaling pathways activated by FGFRs.

FGF-stimulation leads to tyrosine phosphorylation of the docking protein FRS2α and FRS2β, followed by recruitment of multiple Grb2/Sos complexes resulting in activation of the Ras/MAP kinase signaling pathway (Kouhara et al., *Cell* 89: 693-702, 1997). Tyrosine phosphorylated FRS2α functions as a site for coordinated assembly of a multiprotein complex that includes the docking protein Gab1 and the effector proteins that are recruited by this docking protein (Hadari et al., *Proc Natl Acad Sci USA* 98: 8578-8583, 2001). FRS2 proteins contain myristyl anchors and PTB domains in their N-termini and a large region with multiple tyrosine phosphorylation sites at their C-termini (Kouhara, supra). FRS2α contains four binding sites for the adaptor protein Grb2 and two binding sites for the protein tyrosine phosphatase Shp2. FGF-stimulation leads to tyrosine phosphorylation of Shp2 resulting in complex formation with additional Grb2 molecules. Grb2/Sos complexes are thus recruited directly and indirectly via Shp2 upon tyrosine phosphorylation of FRS2α in response to FGF-stimulation.

The central role played by FRS2α in signaling via FGFRs was revealed by exploring FGFR signaling in fibroblasts isolated from FRS2α$^{-/-}$ embryos (Hadari, supra). Targeted disruption of the FRS2α gene causes severe impairment in mouse development resulting in embryonal lethality at E7-7.5. This is consistent with earlier studies demonstrating that FGFR signaling plays critical roles at different stages of embryonic development (see Ornitz and N. Itoh, supra; and Givol et al., supra). As FRS2β is expressed exclusively in the nervous system of the embryo past E10-10.5, the second member of the family is unable to compensate for the loss of FRS2α earlier than E10 resulting in embryonic lethality at E7-7.5.

Experiments with embryonic fibroblasts from FRS2α$^{-/-}$ mice demonstrate that FRS2α plays a critical role in FGF-induced MAP kinase stimulation, PI-3 kinase stimulation, chemotactic response and cell proliferation. By using fibroblasts isolated from FRS2α$^{-/-}$ embryos, it was demonstrated that FGF-induced tyrosine phosphorylation of the docking protein Gab1 depends on tyrosine phosphorylation of FRS2α. Gab1 binds constitutively to the C-terminal SH3 domain of Grb2 and its assembly in complex with Grb2/FRS2α enables tyrosine phosphorylation of Gab1, which is followed by recruitment of a complement of SH2 domain containing signaling proteins including PI-3 kinase. FGF-induced recruitment of PI-3 kinase by Gab1 results in activation of the Akt dependent anti-apoptotic pathway.

In addition to enhancement of tyrosine phosphorylation, FGF-stimulation induces MAP kinase-dependent phosphorylation of FRS2α on at least eight threonine residues resulting in a large shift in its electrophoretic mobility (Lax et al., *Mol Cell* 10: 709-719, 2002). Threonine phosphorylation of FRS2α is accompanied by reduced tyrosine phosphorylation of FRS2α, decreased recruitment of Grb2 and attenuation of the MAP kinase response. A similar FRS2α threonine phosphorylation is induced by PDGF, EGF or insulin stimulation, growth factors or hormones that do not induce tyrosine phosphorylation of FRS2α and do not stimulate the biological responses of FGFs. Prevention of FRS2α threonine phosphorylation by site directed mutagenesis or by treatment of the cells with the MEK inhibitor (PD 0980089) leads to constitutive tyrosine phosphorylation of FRS2α$^{-/-}$ in unstimulated cells. Expression of an FRS2α mutant deficient in MAPK phosphorylation sites (the eight threonines have been replaced by valines, FRS2α-8V), induces anchorage independent cell growth and colony formation in soft agar; two hallmarks of cell transformation. In addition, FGF-induced tyrosine phosphorylation of FRS2α, MAP kinase stimulation and cell migration are strongly enhanced in FRS2α$^{-/-}$ cells expressing FRS2α-8V mutant deficient in MAPK phosphorylation sites (Lax et al., supra).

Several human skeletal dysplasias have been linked to specific point mutations in three members of the FGFR family. It has been shown that point mutations in FGFR1, FGFR2 or FGFR3 are responsible for severe impairment in cranial, digital and skeletal development (reviewed in Webster and Donoghue, *Trends Genet.* 13: 178-182, 1997; and Wilkie, *Hum Mol Genet.* 6: 1647-1656, 1997). The most common craniosynostosis syndrome (premature fusion of cranial sutures) and skeletal dysplasia (dwarfism), have been linked to point mutations in FGFR1, 2 and 3. The mutations in FGFR1 that are responsible for Pfeiffer syndrome and mutations in FGFR2 that are responsible for Pfeiffer, Crouzon, Jackson-Weiss and Apert syndromes were summarized in Table 4 of Eswarakumar et al. (*Cytokine & Growth Factor Reviews* 16(2): 139-149, 2005, incorporated herein by reference) along with available animal models. Furthermore, point mutations in FGFR3 were linked to achondroplasia (ACH), hypochondroplasia (HCH), thanatophoric dysplasia type I and type II (TDI and TDII) (see Table 4 of Eswarakumar et al., supra). The mutations responsible for HCH and TDII, are located in the catalytic PTK domain of FGFR. These are gain of function mutations that enhance the PTK activity in a ligand independent manner. The remaining gain-of-function mutations are confined to transmembrane or extracellular domains of FGFR. The most common form of human dwarfism is caused by a gain of function mutation in the transmembrane domain of FGFR3. Biochemical analyses confirmed that the ACH mutations increase both protein kinase activity and stability of the FGFR3 mutant protein. These results are consistent with the phenotype of FGFR3$^{-/-}$ mice. It was demonstrated that FGFR3 deficiency causes increased bone length due to chondrocyte hypertrophy (Deng et al., Cell 84: 911-921, 1996).

Mutations in the extracellular domain of FGFRs cluster in three regions of the extracellular ligand-binding domain, in the linker connecting D2-D3, in D3 and in the region connecting D3 with the transmembrane domain. The large variety of gain of function mutations detected in these severe skeletal disorders activate the mutant FGFRs by either promoting FGFR dimerization or by altering ligand-receptor specificity. Many of the Crouzon, Pfeiffer or Jackson-Weiss syndromes are caused by mutations in one of the two conserved cysteines in D3 of FGFR2, an amino acid residue that is normally linked intramolecularly to a second cysteine in the D3 of FGFR. The first group are mutations that substitute an amino acid with a cysteine residue or substitute a cysteine with another amino acid. Both types of mutations create an unpaired cysteine in the extracellular domain, which will form an intermolecular disulfide bridge, resulting in receptor dimerization and activation. The structure of the FGF/FGFR complexes suggested that many mutations in D3, although not directly involving cysteine residues, could destabilize the structure of D3 in such a way that certain cysteines that normally participate in the formation of intramolecular disulfide bridges will form instead intermolecular disulfide bridges with a cysteine residue in a neighboring receptor, again resulting in FGFR dimerization and activation. The second class of gain of function mutations that occur in the two highly conserved residues in the linker connecting D2 and D3 (Ser-252 and Pro-253), of FGFR2 are responsible for all known cases of Apert syndrome (Webster and Donoghue, supra; and Wilkie, supra). Both the structural information and ligand-binding experiments indicate that these mutations cause the mesenchymal splice form of FGFR2 (FGFR2c) to bind and to be activated by the mesenchymally expressed ligands FGF7 or FGF10 and the epithelial splice form of FGFR2 (FGFR2b) to be activated by FGF2, FGF6 and FGF9 (Yu et al., Proc Natl Acad Sci USA 97: 14536-14541, 2000; and Ibrahimi et al., Proc Natl Acad Sci USA 98: 7182-7187, 2001).

It has been shown previously that the docking proteins play critical role in receptor tyrosine kinases (RTKs) signaling, for example IRS 1-4 in insulin receptor signaling and FRS2α and β in FGF and NGF signaling, Shc in EGF signaling, and Gab1 in EGF and FGF signaling. Activated FGFRs could indirectly recruit Grb2, Shp2 and Gab1 via FRS2α and directly recruit Shc, PLC-γ and many other molecules. However, the in vivo role of these proteins during development is largely obscured due to the early embryonic lethality of mice deficient in them. For example, mice deficient in FRS2α results in embryonic lethality at E 8.0, Shp2 at E 10.5, Grb2 at E 7.5, Shc at E 11.5 and PLC-γ at E 9.5, probably because these molecules serve as transducers of signals from multiple receptor tyrosine kinases (RTKs). It has also been demonstrated recently that mice deficient in FRS2α have severe pregastrulation defects including failure of anterior-posterior axis formation, impaired cell movement through primitive streak and failure to maintain the trophoblast stem cell population that is required for the development of the placenta (Gotoh et al., Mol Cell Biol 25: 4105-4116, 2005). Because of its early embryonic lethality, the physiological role of FRS2α during postnatal life through adult hood was largely unknown prior to the instant invention. Using both genetic and pharmacological approach, the instant invention first demonstrates that FRS2α mediates the pathogenic signaling that leads to premature fusion of cranial sutures. Thus the agents of the invention, and additional agents that can be identified using the methods of the invention, provides a means to prevent, treat, and/or alleviate symptoms in an individual having or at high risk of having such skeletal deformity.

V. Pharmaceutical Compositions

In certain embodiments, the subject therapeutic agents of the present invention are formulated with a pharmaceutically acceptable carrier or salt. The term "pharmaceutically acceptable salts" refers to physiologically and pharmaceutically acceptable salts of the compounds of the invention, e.g., salts that retain the desired biological activity of the parent compound and do not impart undesired toxicological effects thereto.

Such agents can be administered alone or as a component of a pharmaceutical formulation (composition). The compounds may be formulated for administration in any convenient way for use in human or veterinary medicine. In certain embodiments, the compound included in the pharmaceutical preparation may itself be active, or may be a prodrug. The term "prodrug" refers to compounds which, under physiological conditions, are converted into therapeutically active agents.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Pharmaceutical compositions of the subject therapeutic agents include those suitable for oral nasal, topical, parenteral and/or intravaginal administration. The pharmaceutical compositions may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect.

Methods of preparing these pharmaceutical compositions or compositions include combining a subject therapeutic agent and a carrier and, optionally, one or more accessory ingredients. In general, the pharmaceutical compositions can be prepared with a liquid carrier, or a finely divided solid carrier, or both, and then, if necessary, shaping the product.

Pharmaceutical compositions for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of an artemisinin-related compound as an active ingredient. An artemisinin-related compound may also be administered as a bolus, electuary or paste.

In solid dosage forms for oral administration (capsules, tablets, pills, dragees, powders, granules, and the like), one or more of the subject therapeutic agents of the present invention may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof, and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

Suspensions, in addition to the active compounds, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

In particular, therapeutic agents or pharmaceutical compositions can be topically, either to skin or to mucosal membranes, such as those of the cervix and vagina. The topical pharmaceutical compositions may further include one or more of the wide variety of agents known to be effective as skin or stratum corneum penetration enhancers. Examples of these are 2-pyrrolidone, N-methyl-2-pyrrolidone, dimethylacetamide, dimethylformamide, propylene glycol, methyl or isopropyl alcohol, dimethyl sulfoxide, and azone. Additional agents may further be included to make the formulation cosmetically acceptable. Examples of these are fats, waxes, oils, dyes, fragrances, preservatives, stabilizers, and surface active agents. Keratolytic agents such as those known in the art may also be included. Examples are salicylic acid and sulfur.

Dosage forms for the topical or transdermal administration include powders, sprays, ointments, pastes, creams, lotions, gels, solutions, patches, and inhalants. The active compound may be mixed under sterile conditions with a pharmaceutically acceptable carrier, and with any preservatives, buffers, or propellants which may be required. The ointments, pastes, creams and gels may contain, in addition to an artemisinin-related compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a subject therapeutic agent, excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

Pharmaceutical compositions suitable for parenteral administration may comprise one or more therapeutic agents in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

Injectable depot forms are made by forming microencapsule matrices of one or more therapeutic agents in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable pharmaceutical compositions are also prepared by entrapping the drug in liposomes or microemulsions which are compatible with body tissue.

Pharmaceutical compositions for intravaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound. Optionally, such pharmaceutical compositions suitable for vaginal administration also include pessaries, tampons, creams, gels, pastes, foams or spray pharmaceutical compositions containing such carriers as are known in the art to be appropriate.

VI. Methods of Administration

In certain embodiments, the subject methods of the invention can be used alone. Alternatively, the subject methods may be used in combination with other conventional therapeutic approaches directed to treatment or prevention of the craniosynostosis syndrome and/or skeletal dysplasia conditions resulting from abnormal FGFR activity disorders.

When a subject therapeutic agent of the present invention is administered in combination with another conventional agent, either concomitantly or sequentially, such therapeutic agent may enhance the therapeutic effect of the conventional agent. This may allow decrease of dosage of a conventional agent, thereby reducing the undesirable side effects.

Depending on the nature of the cancer and the therapy, administration of the therapeutic agents of the invention may be continued while the other therapy is being administered and/or thereafter. Administration of the subject therapeutic agents may be made in a single dose, or in multiple doses. In some instances, administration of the subject therapeutic agents is commenced at least several days prior to the conventional therapy, while in other instances, administration is begun either immediately before or at the time of the administration of the conventional therapy.

VII. Delivery Means

The instant invention also provides expression vectors comprising a nucleotide sequence encoding a subject agent (nucleotide) operably linked to at least one regulatory sequence. "Operably linked" when describing the relationship between two DNA regions simply means that they are functionally related to each other. For example, a promoter or other transcriptional regulatory sequence is operably linked to a coding sequence if it controls the transcription of the coding sequence. Alternatively, "operably linked" is intended to mean that the nucleotide sequence is linked to a regulatory sequence in a manner which allows expression of the nucleotide sequence. Regulatory sequences are art-recognized and are selected to direct expression of the encoded polypeptide. Accordingly, the term regulatory sequence includes promoters, enhancers and other expression control elements. Exemplary regulatory sequences are described in Goeddel; *Gene Expression Technology: Methods in Enzymology* 185, Academic Press, San Diego, Calif. (1990). For instance, any of a wide variety of expression control sequences-sequences that control the expression of a DNA sequence when operatively linked to it may be used in these vectors to express DNA sequences encoding the chimeric polypeptides of this invention. Such useful expression control sequences, include, for example, the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of inhibitors desired to be expressed. Moreover, the vector's copy number, the ability to control that copy number and the expression of any other proteins encoded by the vector, such as antibiotic markers, should also be considered.

As will be apparent, the subject gene constructs can be used to cause expression of the subject agent in target cells, e.g., to produce inhibitors that inhibit the function of FGFR and FRS2, or other downstream signaling proteins as described above.

In certain therapeutic applications, the ex vivo-derived inhibitors are utilized in a manner appropriate for therapy in general. For such therapy, the inhibitors or vectors encoding inhibitors of the invention can be formulated for a variety of modes of administration, including systemic and topical or localized administration. In such embodiments, a polypeptide inhibitor may be combined with a pharmaceutically acceptable excipient, e.g., a non-pyrogenic excipient. Techniques and formulations generally may be found in *Remington's Pharmaceutical Sciences*, Meade Publishing Co., Easton, Pa. Systemic administration, if injection is chosen, includes intramuscular, intravenous, intraperitoneal, and subcutaneous injection. The inhibitors of the invention can be formulated in liquid solutions, for example, in physiologically compatible buffers such as Hank's solution or Ringer's solution. In addition, the inhibitors may be formulated in solid form and redissolved or suspended immediately prior to use. Lyophilized forms are also included.

Systemic administration can also be by transmucosal or transdermal means, or the compounds can be administered orally. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For oral administration, the peptides are formulated into conventional oral administration forms such as capsules, tablets, and tonics. For topical administration, particularly cosmetic pharmaceutical compositions, the oligomers of the invention are formulated into ointments, salves, gels, or creams as generally known in the art.

Alternative means of administration of peptides have been developed. Sustained-release pharmaceutical compositions (Putney, et al. *Nature Biotechnology* 16: 153-157, 1998) are advantageous, requiring fewer administrations and, often, lower dosages. Techniques for oral delivery of peptides have been reviewed (Fasano, A. *Trends in Biotechnology* 16: 152-157, 1998), as have several site-specific means of peptide delivery (Pettit, D. K. et al. *Trends in Biotechnology* 16: 343-349, 1998). Additional techniques for therapeutic administration of peptides are known to those of skill in the art.

Genetic material inhibitors of the present invention can be delivered, for example, as an expression plasmid which, when transcribed in the cell, produces the desired inhibitor (e.g. RNA).

In one embodiment, the genetic material is provided by use of an "expression" construct, which can be transcribed in a cell to produce the inhibitor. Such expression constructs may be administered in any biologically effective carrier, e.g., any formulation or composition capable of effectively transfecting cells either ex vivo or in vivo with genetic material encoding an inhibitor. Approaches may include insertion of the antisense nucleic acid in viral vectors including recombinant retroviruses, adenoviruses, adeno-associated viruses, human immunodeficiency viruses, and herpes simplex viruses-1, or recombinant bacterial or eukaryotic plasmids. Viral vectors can be used to transfect cells directly; plasmid DNA can be delivered with the help of, for example, cationic liposomes (lipofectin) or derivatized (e.g., antibody conjugated), polylysine conjugates, gramacidin S, artificial viral envelopes or other such intracellular carriers, as well as direct injection of the gene construct or calcium phosphate precipitation carried out in vivo. It will be appreciated that because transduction of appropriate target cells represents the critical first step in gene therapy, choice of the particular gene delivery system will depend on such factors as the phenotype of the intended target and the route of administration, e.g., locally or systemically.

As used herein, the term "vector" refers to a nucleic acid molecule capable of transporting another nucleic acid to that it has been linked. One type of vector is a genomic integrated vector, or "integrated vector," which can become integrated into the chromosomal DNA of the host cell. Another type of vector is an episomal vector, e.g., a nucleic acid capable of extra-chromosomal replication. Vectors capable of directing the expression of genes to that they are operatively linked are referred to herein as "expression vectors." In the present specification, "plasmid" and "vector" are used interchangeably unless otherwise clear from the context. In the expression vectors, regulatory elements controlling transcription can be generally derived from mammalian, microbial, viral or insect genes. The ability to replicate in a host, usually conferred by an origin of replication, and a selection gene to facilitate recognition of transformants may additionally be incorporated. Vectors derived from viruses, such as retroviruses, adenoviruses, and the like, may be employed.

One approach to in vivo introduction of genetic material encoding one of the subject inhibitors into a cell is by use of a viral vector containing said genetic material. Infection of cells with a viral vector has the advantage that a large proportion of the targeted cells can receive the nucleic acid. Additionally, inhibitors encoded by genetic material in the viral vector, e.g., by a nucleic acid contained in the viral vector, are expressed efficiently in cells which have taken up viral vector nucleic acid. Such a strategy may be particularly effective when skeletal muscle cells are the targets of the vector (Fisher, K. J. et al. *Nature Medicine* 3: 306-312, 1997).

Retrovirus vectors and adeno-associated virus vectors are generally understood to be the recombinant gene delivery system of choice for the transfer of exogenous genes in vivo, particularly into humans. These vectors provide efficient delivery of genes into cells, and the transferred nucleic acids are stably integrated into the chromosomal DNA of the host. A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller, *Blood* 76: 271, 1990). Thus, recombinant retrovirus can be constructed in which part of the retroviral coding sequence (gag, pol, env) has been replaced by nucleic acid encoding one of the antisense E6AP constructs, rendering the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10-9.14, and other standard laboratory manuals. Examples of suitable retroviruses include pLJ, pZIP, pWE and pEM which are well known to those skilled in the art. Examples of suitable packaging virus lines for preparing both ecotropic and amphotropic retroviral systems include ψCrip, ψCre, ψ2 and ψAm. Retroviruses have been used to introduce a variety of genes into many different cell types, including neural cells, epithelial cells, endothelial cells, lymphocytes, myoblasts, hepatocytes, bone marrow cells, in vitro and/or in vivo (see for example Eglitis, et al. *Science* 230: 1395-1398, 1985; Danos and Mulligan, *Proc. Natl. Acad. Sci. USA* 85: 6460-6464, 1988; Wilson et al., *Proc. Natl. Acad. Sci. USA* 85: 3014-3018, 1988; Armentano et al., *Proc. Natl. Acad. Sci. USA* 87: 6141-6145, 1990; Huber et al., *Proc. Natl. Acad. Sci. USA* 88: 8039-8043, 1991; Ferry et al., *Proc. Natl. Acad. Sci. USA* 88: 8377-8381, 1991; Chowdhury et al., *Science* 254: 1802-1805, 1991; van Beusechem et al., *Proc. Natl. Acad. Sci. USA* 89: 7640-7644, 1992; Kay et al., *Human Gene Therapy* 3: 641-647, 1992; Dai et al., *Proc. Natl. Acad. Sci. USA* 89: 10892-10895, 1992; Hwu et al., *J. Immunol.* 150: 4104-4115, 1993; U.S. Pat. No. 4,868,116; U.S. Pat. No. 4,980,286; PCT Application WO 89/07136; PCT Application WO 89/02468; PCT Application WO 89/05345; and PCT Application WO 92/07573).

In choosing retroviral vectors as a gene delivery system for genetic material encoding the subject chimeric polypeptides, it is important to note that a prerequisite for the successful infection of target cells by most retroviruses, and therefore of stable introduction of the genetic material, is that the target cells must be dividing. In general, this requirement will not be a hindrance to use of retroviral vectors. In fact, such limitation on infection can be particularly beneficial in the instant circumstances wherein the normal tissue (e.g., nontransformed cells) surrounding the target cells does not undergo extensive cell division and is therefore refractory to infection with retroviral vectors.

Furthermore, it has been shown that it is possible to limit the infection spectrum of retroviruses and consequently of retroviral-based vectors, by modifying the viral packaging proteins on the surface of the viral particle (see, for example, PCT publications WO93/25234, WO94/06920, and WO94/11524). For instance, strategies for the modification of the infection spectrum of retroviral vectors include: coupling antibodies specific for cell surface antigens to the viral env protein (Roux et al., *PNAS* 86: 9079-9083, 1989; Julan et al., *J. Gen Virol* 73: 3251-3255, 1992; and Goud et al., *Virology* 163: 251-254, 1983); or coupling cell surface ligands to the viral env proteins (Neda et al., *J Biol Chem* 266: 14143-14146, 1991). Coupling can be in the form of the chemical cross-linking with a protein or other variety (e.g., lactose to convert the env protein to an asialoglycoprotein), as well as by generating chimeric proteins (e.g., single-chain antibody/env chimeric proteins). This technique, while useful to limit or otherwise direct the infection to certain tissue types, and can also be used to convert an ecotropic vector in to an amphotropic vector.

Moreover, use of retroviral gene delivery can be further enhanced by the use of tissue- or cell-specific transcriptional regulatory sequences (such as breast or ovary-specific regulatory sequences) which control expression of the genetic material of the retroviral vector.

Another viral gene delivery system useful in the present invention utilizes adenovirus-derived vectors. The genome of an adenovirus can be manipulated such that it encodes a gene product of interest, but is inactive in terms of its ability to replicate in a normal lytic viral life cycle (see, for example, Berkner et al., *BioTechniques* 6: 616, 1988; Rosenfeld et al., *Science* 252: 431-434, 1991; and Rosenfeld et al., *Cell* 68: 143-155, 1992). Suitable adenoviral vectors derived from the adenovirus strain Ad type 5 dl324 or other strains of adenovirus (e.g., Ad2, Ad3, Ad7, etc.) are well known to those skilled in the art. Recombinant adenoviruses can be advantageous in certain circumstances in that they are capable of infecting non-dividing cells and can be used to infect a wide variety of cell types, including airway epithelium (Rosenfeld et al., cited supra, 1992), endothelial cells (Lemarchand et al., *Proc. Natl. Acad. Sci. USA* 89: 6482-6486, 1992), hepatocytes (Herz and Gerard, *Proc. Natl. Acad. Sci. USA* 90: 2812-2816, 1993) and muscle cells (Quantin et al., *Proc. Natl. Acad. Sci. USA* 89: 2581-2584, 1992). Furthermore, the virus particle is relatively stable and amenable to purification and concentration, and, as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al., supra; Haj-Ahmand and Graham, J. Virol. 57: 267, 1986). Most replication-defective adenoviral vectors currently in use and therefore favored by the present invention are deleted for all or parts of the viral E1 and E3 genes but retain as much as 80% of the adenoviral genetic material (see, for example, Jones et al., Cell 16: 683, 1979; Berkner et al., supra; and Graham et al. in *Methods in Molecular Biology*, E. J. Murray, Ed. (Humana, Clifton, N.J., 1991) vol. 7. pp. 109-127). Expression of the inserted genetic material can be under control of, for example, the E1A promoter, the major late promoter (MLP) and associated leader sequences, the E3 promoter, or exogenously added promoter sequences.

Yet another viral vector system useful for delivery of genetic material encoding the subject chimeric polypeptides is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. *Curr. Topics in Micro. and Immunol.* (1992) 158:97-129). It is also one of the few viruses that may integrate its DNA into non-dividing cells, and exhibits a high frequency of stable integration (see for example Flotte et al. (1992) *Am. J. Respir. Cell. Mol. Biol.* 7:349-356; Samulski et al. (1989) *J. Virol.* 63:3822-3828; and McLaughlin et al. (1989) *J. Virol.* 62:1963-1973). Vectors containing as little as 300 base pairs of AAV can be packaged and can integrate. Space for exogenous DNA is limited to about 4.5 kb. An AAV vector such as that described in Tratschin et al. (1985) *Mol. Cell. Biol.* 5:3251-3260 can be used to introduce DNA into cells. A variety of nucleic acids have been introduced into different cell types using AAV vectors (see for example Hermonat et al. (1984) *Proc. Natl. Acad. Sci. USA* 81:6466-6470; Tratschin et al. (1985) *Mol. Cell. Biol.* 4:2072-2081; Wondisford et al. (1988) *Mol. Endocrinol.* 2:32-39; Tratschin et al. (1984) *J. Virol.* 51:611-619; and Flotte et al. (1993) *J. Biol. Chem.* 268:3781-3790).

Other viral vector systems that may have application in gene therapy have been derived from herpes virus, vaccinia virus, and several RNA viruses.

In addition to viral transfer methods, such as those illustrated above, non-viral methods can also be employed to cause expression of genetic material encoding the subject inhibitors in the tissue of an animal. Most nonviral methods of gene transfer rely on normal mechanisms used by mammalian cells for the uptake and intracellular transport of macromolecules. In certain embodiments, non-viral gene delivery systems of the present invention rely on endocytic pathways for the uptake of genetic material by the targeted cell. Exemplary gene delivery systems of this type include liposomal derived systems, polylysine conjugates, and artificial viral envelopes.

In a representative embodiment, genetic material can be entrapped in liposomes bearing positive charges on their surface (e.g., lipofectins) and, optionally, which are tagged with antibodies against cell surface antigens of the target tissue (Mizuno et al. (1992) *No Shinkei Geka* 20:547-551; PCT publication WO91/06309; Japanese patent application 1047381; and European patent publication EP-A-43075). For example, lipofection of papilloma-infected cells can be carried out using liposomes tagged with monoclonal antibodies against PV-associated antigen (see Viac et al. (1978) *J Invest Dermatol* 70:263-266; see also Mizuno et al. (1992) *Neurol. Med. Chir.* 32:873-876).

In yet another illustrative embodiment, the gene delivery system comprises an antibody or cell surface ligand which is cross-linked with a gene binding agent such as polylysine (see, for example, PCT publications WO93/04701, WO92/22635, WO92/20316, WO92/19749, and WO92/06180). For example, genetic material encoding the subject chimeric polypeptides can be used to transfect hepatocytic cells in vivo using a soluble polynucleotide carrier comprising an asialoglycoprotein conjugated to a polycation, e.g., polylysine (see U.S. Pat. No. 5,166,320). It will also be appreciated that effective delivery of the subject nucleic acid constructs via mediated endocytosis can be improved using agents which enhance escape of the gene from the endosomal structures. For instance, whole adenovirus or fusogenic peptides of the influenza HA gene product can be used as part of the delivery system to induce efficient disruption of DNA-containing endosomes (Mulligan et al (1993) *Science* 260-926; Wagner et al. (1992) *PNAS* 89:7934; and Christiano et al. (1993) *PNAS* 90:2122).

In clinical settings, the gene delivery systems can be introduced into an individual by any of a number of methods, each of which is familiar in the art. For instance, a pharmaceutical preparation of the gene delivery system can be introduced systemically, e.g., by intravenous injection, and specific transduction of the target cells occurs predominantly from specificity of transfection provided by the gene delivery vehicle, cell-type or tissue-type expression due to the transcriptional regulatory sequences controlling expression of the gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g., Chen et al. (1994) *PNAS* 91: 3054-3057).

Moreover, the pharmaceutical preparation can consist essentially of the gene delivery system in an acceptable diluent, or can comprise a slow release matrix in which the gene delivery vehicle is imbedded. Alternatively, where the complete gene delivery system can be produced intact from recombinant cells, e.g., retroviral packages, the pharmaceutical preparation can comprise one or more cells which produce the gene delivery system. In the latter case, methods of introducing the viral packaging cells may be provided by, for example, rechargeable or biodegradable devices. Various slow release polymeric devices have been developed and tested in vivo in recent years for the controlled delivery of drugs, including proteinaceous biopharmaceuticals, and can be adapted for release of viral particles through the manipulation of the polymer composition and form. A variety of biocompatible polymers (including hydrogels), including both biodegradable and non-degradable polymers, can be used to form an implant for the sustained release of the viral particles by cells implanted at a particular target site. Such embodiments of the present invention can be used for the delivery of an exogenously purified virus, which has been incorporated in the polymeric device, or for the delivery of viral particles produced by a cell encapsulated in the polymeric device.

By choice of monomer composition or polymerization technique, the amount of water, porosity and consequent permeability characteristics can be controlled. The selection of the shape, size, polymer, and method for implantation can be determined on an individual basis according to the disorder to be treated and the individual patient response. The generation of such implants is generally known in the art. See, for example, *Concise Encyclopedia of Medical & Dental Materials*, ed. by David Williams (MIT Press: Cambridge, Mass., 1990); and the Sabel et al. U.S. Pat. No. 4,883,666. In another embodiment of an implant, a source of cells producing a recombinant virus is encapsulated in implantable hollow fibers. By "recombinant virus" is meant a virus that has been genetically altered, e.g., by the addition or insertion of a heterologous nucleic acid construct into the particle.

Such fibers can be pre-spun and subsequently loaded with the viral source (Aebischer et al. U.S. Pat. No. 4,892,538; Aebischer et al. U.S. Pat. No. 5,106,627; Hoffman et al. (1990) *Expt. Neurobiol.* 110:39-44; Jaeger et al. (1990) *Prog. Brain Res.* 82:41-46; and Aebischer et al. (1991) *J. Biomech. Eng.* 113:178-183), or can be co-extruded with a polymer which acts to form a polymeric coat about the viral packaging cells (Lim U.S. Pat. No. 4,391,909; Sefton U.S. Pat. No. 4,353,888; Sugamori et al. (1989) *Trans. Am. Artif Intern. Organs* 35:791-799; Sefton et al. (1987) *Biotechnol. Bioeng.* 29:1135-1143; and Aebischer et al. (1991) *Biomaterials* 12:50-55). Again, manipulation of the polymer can be carried out to provide for optimal release of viral particles.

Inhibitors of the present invention can be designed by using molecular modeling. A computer model of, for example, FGFR or FRS2 may be used to identify any compounds that might bind FGFR or FRS2 in their target binding sites. Alternatively, antagonistic compounds mimicking the natural ligands of these receptors might be designed in silica. Alternatively, the nature of the inhibitory sequence can be determined by calculation, based on knowledge of a receptor or binding pocket. Other calculational strategies will be known to those skilled in the art. Calculations such as these can be useful for directing the synthesis of inhibitors of the present invention in a time- and material-efficient manner, before actual synthesis and screening techniques begin.

Methods for screening inhibitors of the present invention are well known in the art, independent of the use of computer modeling. The use of peptide libraries is one way of screening large numbers of polypeptides at once. In one screening assay, the candidate peptides are displayed on the surface of a cell or viral particle, and the ability of particular cells or viral particles to bind a target molecule, such as a receptor protein via this gene product is detected in a "panning assay". For instance, the gene library can be cloned into the gene for a surface membrane protein of a bacterial cell, and the resulting chimeric polypeptide detected by panning (Ladner et al., WO 88/06630; Fuchs et al., *Bio/Technology* 9: 1370-1371, 1991; and Goward et al., *TIBS* 18: 136-140, 1992).

In an alternate embodiment, the peptide library is expressed as chimeric polypeptides on the surface of a viral particle. For instance, in the filamentous phage system, foreign peptide sequences can be expressed on the surface of infectious phage, thereby conferring two significant benefits. First, since the phage can be applied to affinity matrices at very high concentrations, a large number of phage can be screened at one time. Second, since each infectious phage displays the combinatorial gene product on its surface, if a particular phage is recovered from an affinity matrix in low yield, the phage can be amplified by another round of infection. The group of almost identical *E. coli* filamentous phages M13, fd, and f1 are most often used in phage display libraries, as either of the phage gIII or gVIII coat proteins can be used to generate chimeric polypeptides without disrupting the ultimate packaging of the viral particle (Ladner et al. PCT publication WO 90/02809; Garrard et al., PCT publication WO 92/09690; Marks et al. (1992) *J. Biol. Chem.* 267:16007-16010; Griffiths et al. (1993) *EMBO J.* 12:725-734; Clackson et al. (1991) *Nature* 352:624-628; and Barbas et al. (1992) *PNAS* 89:4457-4461).

The field of combinatorial peptide libraries has been reviewed (Gallop et al. *J. Med. Chem.* 1994, 37, 1233-1251), and additional techniques are known in the art (Gustin, K. *Virology* 1993, 193, 653-660; Goeddel et al. U.S. Pat. No. 5,223,408; Markland et al. PCT publication WO92/15679; Bass et al. *Proteins: Structure, Function and Genetics* 1990, 8, 309-314; Cunningham, B. C. *Science* 1990, 247, 1461-1465; Lowman, H. B. *Biochemistry* 1991, 30, 10832-10838; Fowlkes et al. U.S. Pat. No. 5,789,184; Houghton, *Proc. Natl. Acad. Sci. U.S.A.* 1985, 82, 5131-5135) for generating and screening peptide libraries.

U.S. Pat. No. 6,420,110 (incorporated herein by reference) discloses a method for isolating biologically active peptides. Using the techniques disclosed therein, a polypeptide inhibitor of the present invention may be developed which interacts with a chosen receptor, and inhibits the signaling of said receptor. The inhibition can be readily tested in many suitable in vitro or in vivo models, using such art-recognized techniques as reporter genes and/or selectable markers under the control of promoters responsive to, for example, FGFR and/or FRS2.

In a representative example, this method is utilized to identify polypeptide inhibitors which have antagonistic activity with respect to one or more types of cells expressing at least one member of the subject target genes. One of skill in the art will readily be able to modify the procedures outlined below to find polypeptides with any desired activity. For example, in the display mode, the chimeric polypeptide library can be panned with the target cells or immobilized FGFR or FRS2 in order to enrich for polypeptides which bind to that cell or receptor/protein. At that stage, the polypeptide library can also be panned against one or more control cell lines (that does not express any of the FGFR or FRS2) in order to remove polypeptides which bind the control cells. In this manner, the polypeptide library which is then tested in the secretion mode can be enriched for polypeptides which selectively bind target cells (relative to the control cells). Thus, for example, the display mode can produce a polypeptide library enriched for polypeptides which preferentially bind FGFR or FRS2.

In the secretion mode, the polypeptides are tested for their biological activity against the target cell using any of a number of techniques known in the art. For instance, the subject in vitro calvaria organ culture. As above, the secretion mode can include negative controls in order to select for polypeptides with specific antagonistic biological activity.

The ability of particular polypeptides to modulate a signal transduction activity of the target receptor can be scored for by detecting up or down-regulation of the detection signal. For example, second messenger generation (e.g., GTPase activity, phospholipid hydrolysis, or protein phosphorylation patterns as examples) can be measured directly. Alternatively, the use of an indicator gene can provide a convenient readout. In other embodiments a detection means consists of an indicator gene. In any event, a statistically significant change in the detection signal can be used to facilitate identification of compounds which modulate receptor or ion channel activities.

By this method, polypeptides which induce a signal pathway from a particular receptor (e.g. FGFR2) can be identified. If a test polypeptide does not appear to induce the activity of the receptor protein, the assay may be repeated as described above, and modified by the introduction of a step in which the reagent cell is first contacted with a known activator of the target receptor to induce signal transduction, and the test peptide can be assayed for its ability to inhibit the activated receptor, for example, to identify antagonists. In yet other embodiments, peptides can be screened for those which potentiate the response to a known activator of the receptor.

EXAMPLES

The following examples are for illustrative purpose only, and should in no way be construed to be limiting in any respect of the claimed invention.

Example 1

FGFR2IIIb and FGFR2IIIc Knock-Out Mice

The b and c variants of fibroblast growth factor receptor 2 (FGFR2) differ in sequence, binding specificity, and localization. It has been shown that the FGFR2IIIb isoform is exclusively expressed in epithelial cells (also designated as KGFR), and is required for limb outgrowth and branching morphogenesis. In contrast, FGFR2IIIc is expressed exclusively in mesenchymal cells (Orr-Urtreger et al., *Dev Biol* 158: 475-486, 1993), and is required by the osteocyte lineage for normal skeletogenesis. The lineage-specific expression of the IIIb and IIIc isoforms of FGFRs enables interaction between the epithelial and mesenchymal layers during development in response to different FGFs.

Figure 4A:
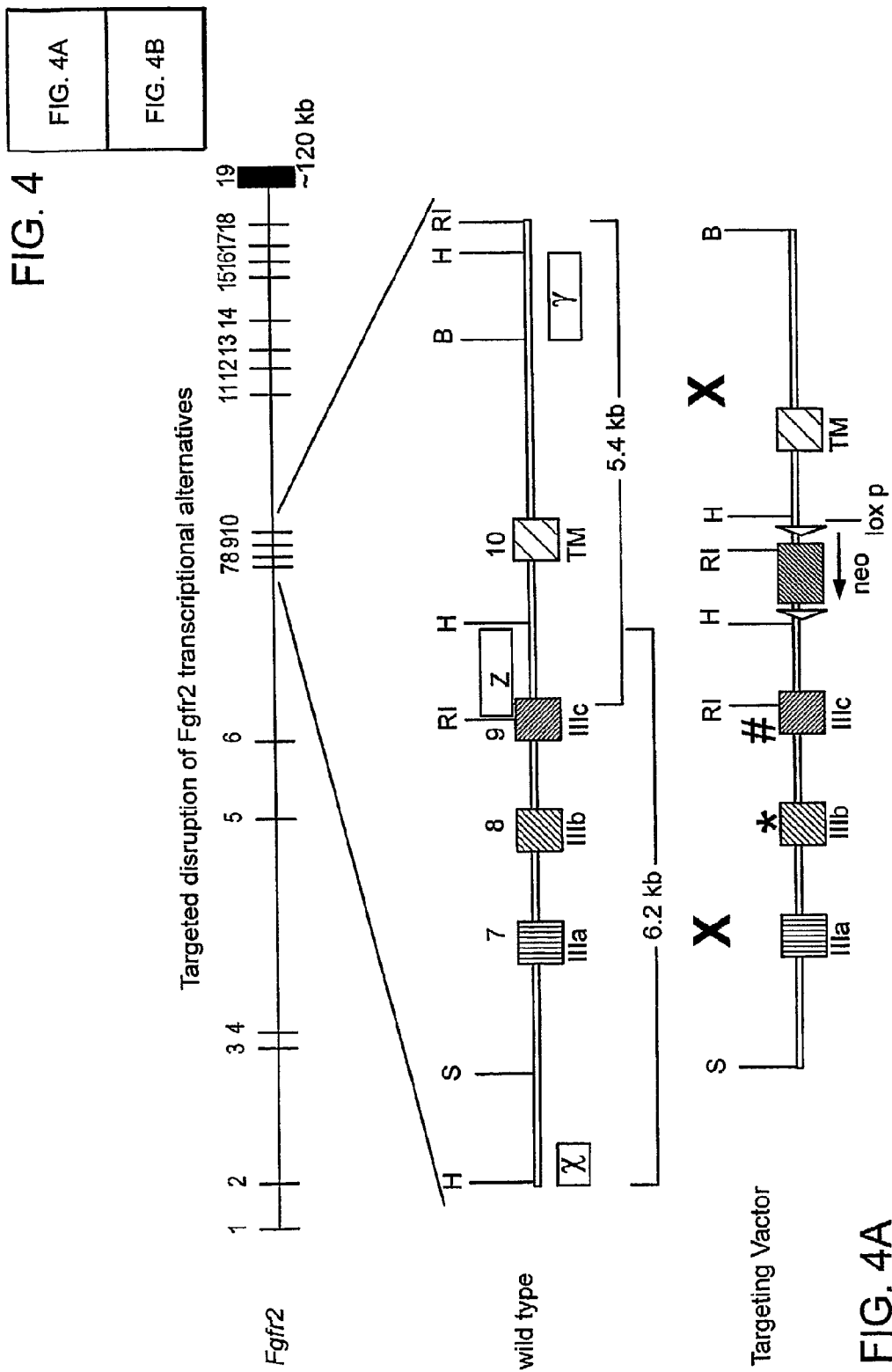
FIG. 4 is a schematic drawing showing targeted disruption of FGFR2 transcriptional alternatives (FGFR2IIIb and IIIc). A portion of the wild-type FGFR2 gene (vertical bars represent exons) is enlarged. Also shown is the targeting vector, and the resulting recombinant. The two panels of blots at the bottoms confirms the successful recombination in heterozygotes.
Figure 4B:
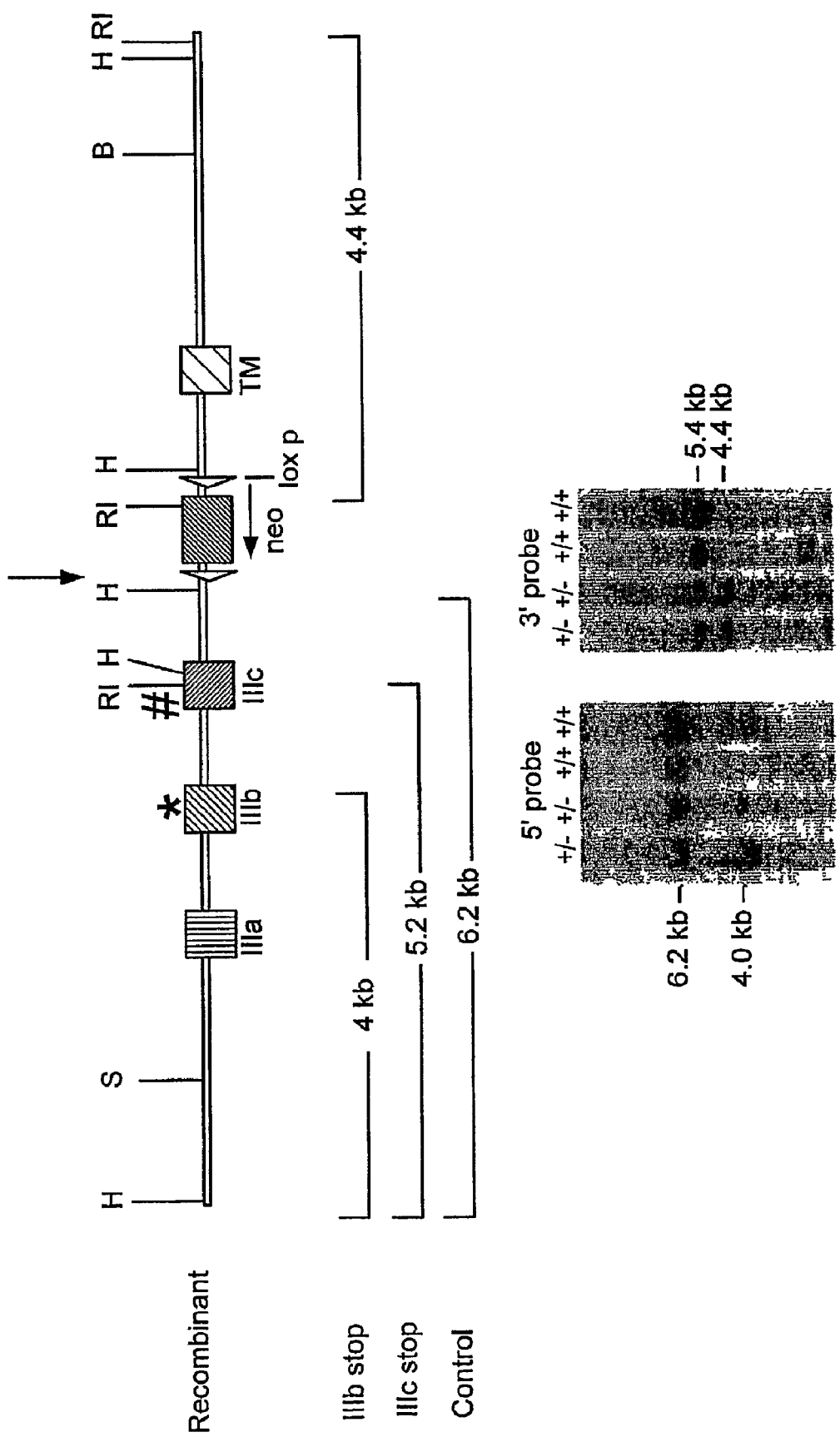
Figure 5:
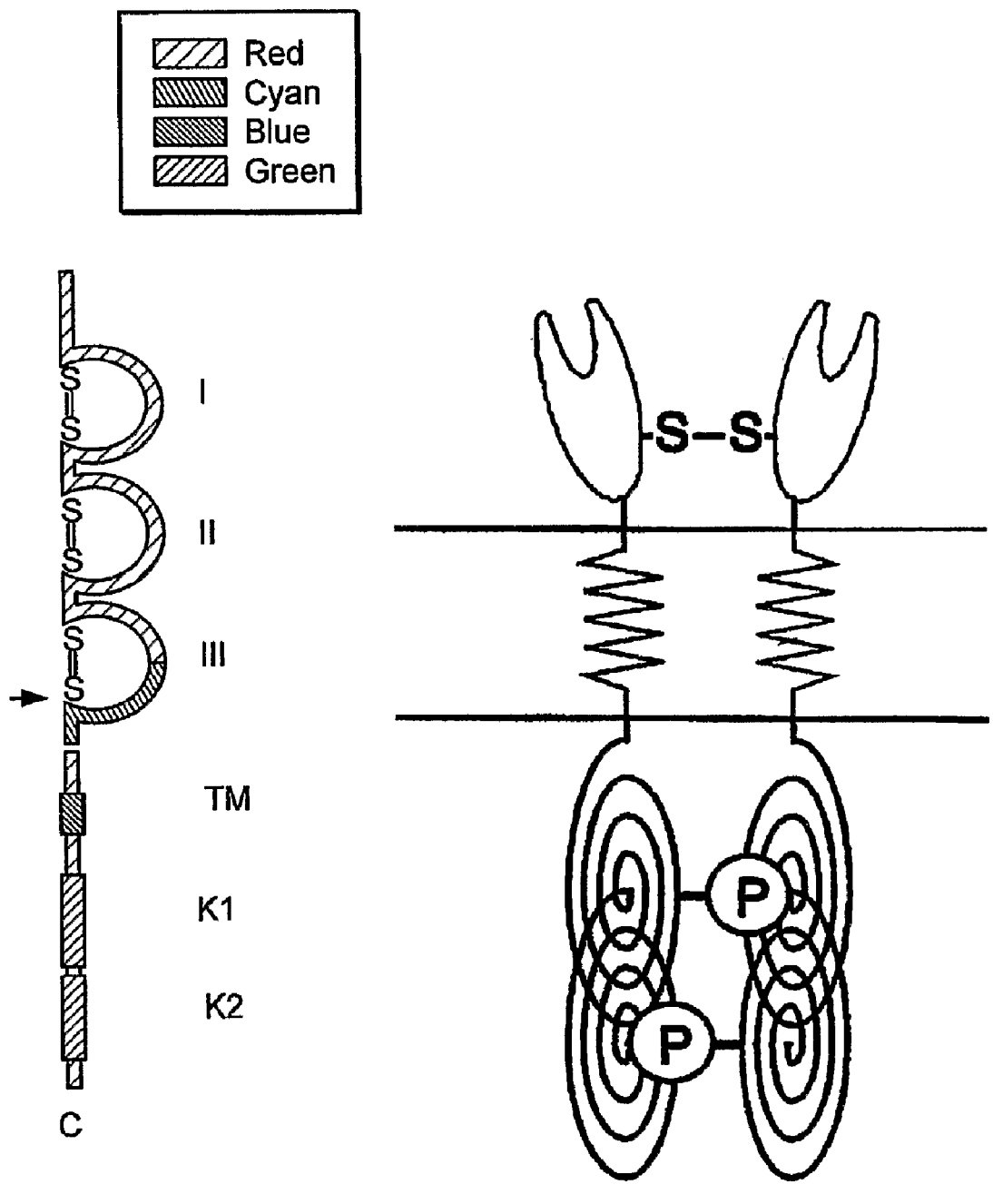
FIG. 5 shows the FGFR2IIIc isoform. The arrow in the left panel points to Cys-342, which normally participates in intramolecular disulfide bond formation in D3 (or DIII). The right panel shows a constitutively active mutant FGFR2IIIc dimer, where an intermolecular disulfide bond is formed, resulting in ligand-independent FGFR2 dimerization. The intermolecular disulfide bond may be formed as a result of disrupting the normal intramolecular disulfide bond (e.g, by mutating the Cys-342 residue).
Figure 6:
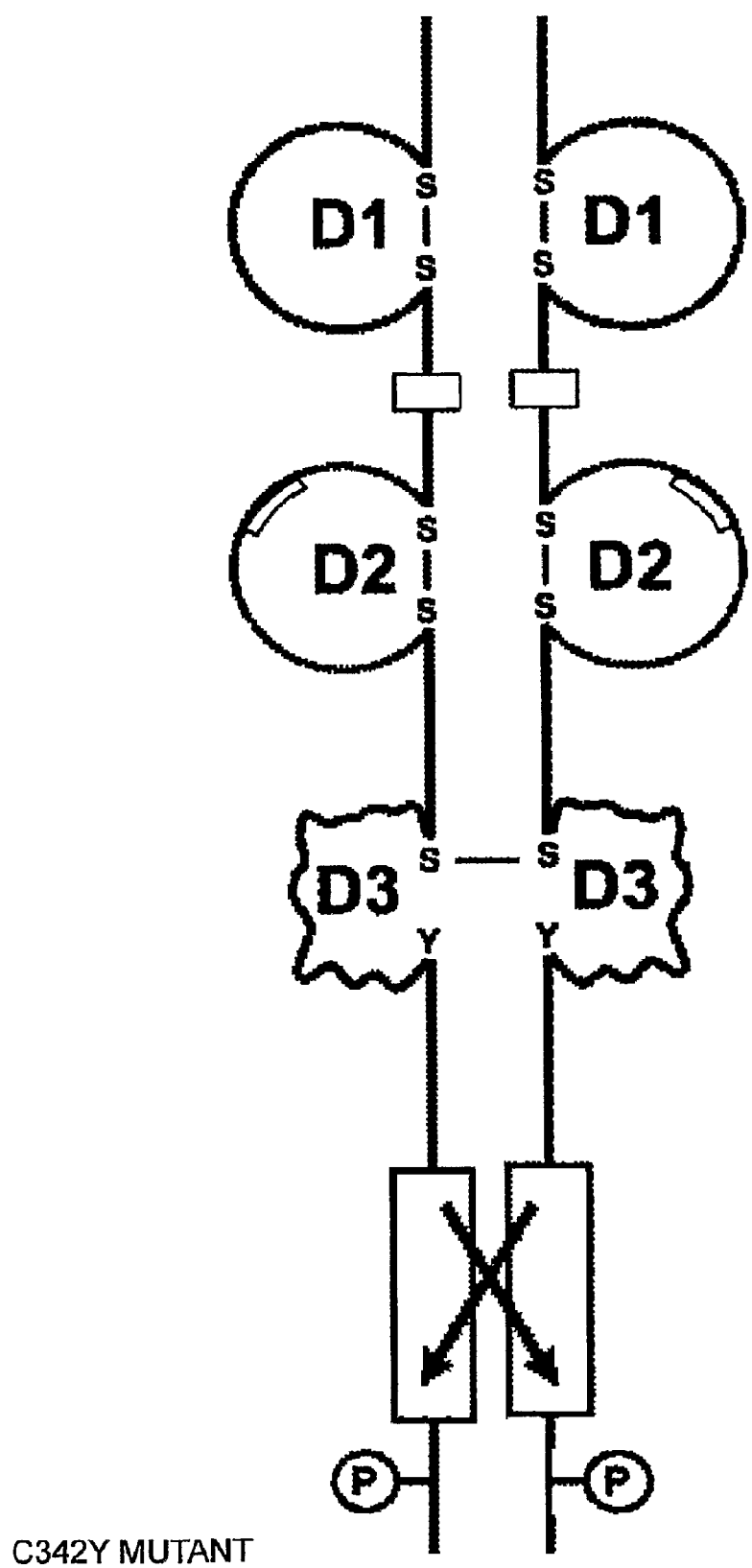
FIG. 6 shows one type of constitutively active FGFR2IIIc dimer, where the Cys-342 residue is mutated to Tyr in both monomers, resulting in intermolecular disulfide bond formation and a gain-of-function FGFR2IIIc mutation.

In order to determine the function of wt FGFR2 functions in vivo, constructs were prepared to selectively inactivate either the FGFR2IIIb or FGFR2IIIc transcriptional isoforms (see FIG. 4).

Selective disruption of the FGFR2IIIb isoform causes severe impairment in the development of the lung, limbs and other tissues, resulting in lethality immediately after birth (P0). Disruption of the FGFR2IIIc isoform, on the other hand, results in impairment in skull and bone development, but the mutant mice are viable. The body weight of the mutants were also about half of their normal litter-mates (results not shown). This indicates that FGFR2IIIc plays an important role in skull and bone development.

Example 2

Knock-In Mouse with the C342Y Crouzon Syndrome Mutation

The following describes a murine model for human craniosynostosis by generating knock-in mice corresponding to the gain of function mutation in Fgfr2c that is responsible for Crouzon syndrome. Further details of the experiments are described in Eswarakumar et al., *Proc Natl Acad Sci U.S.A.* 101: 12555-12560, 2004 (incorporated herein by reference).

Gain-of-function mutations in human FGFR2c are associated with craniosynostosis syndromes. To confirm and extend this evidence, we introduced a Cys342Tyr replacement into Fgfr2c to create a gain-of-function mutation equivalent to a mutation in human Crouzon and Pfeiffer syndromes (see FIG. 7B). The point mutation also creates a new RsaI restriction endonuclease site in the coding sequence.

Figure 9:
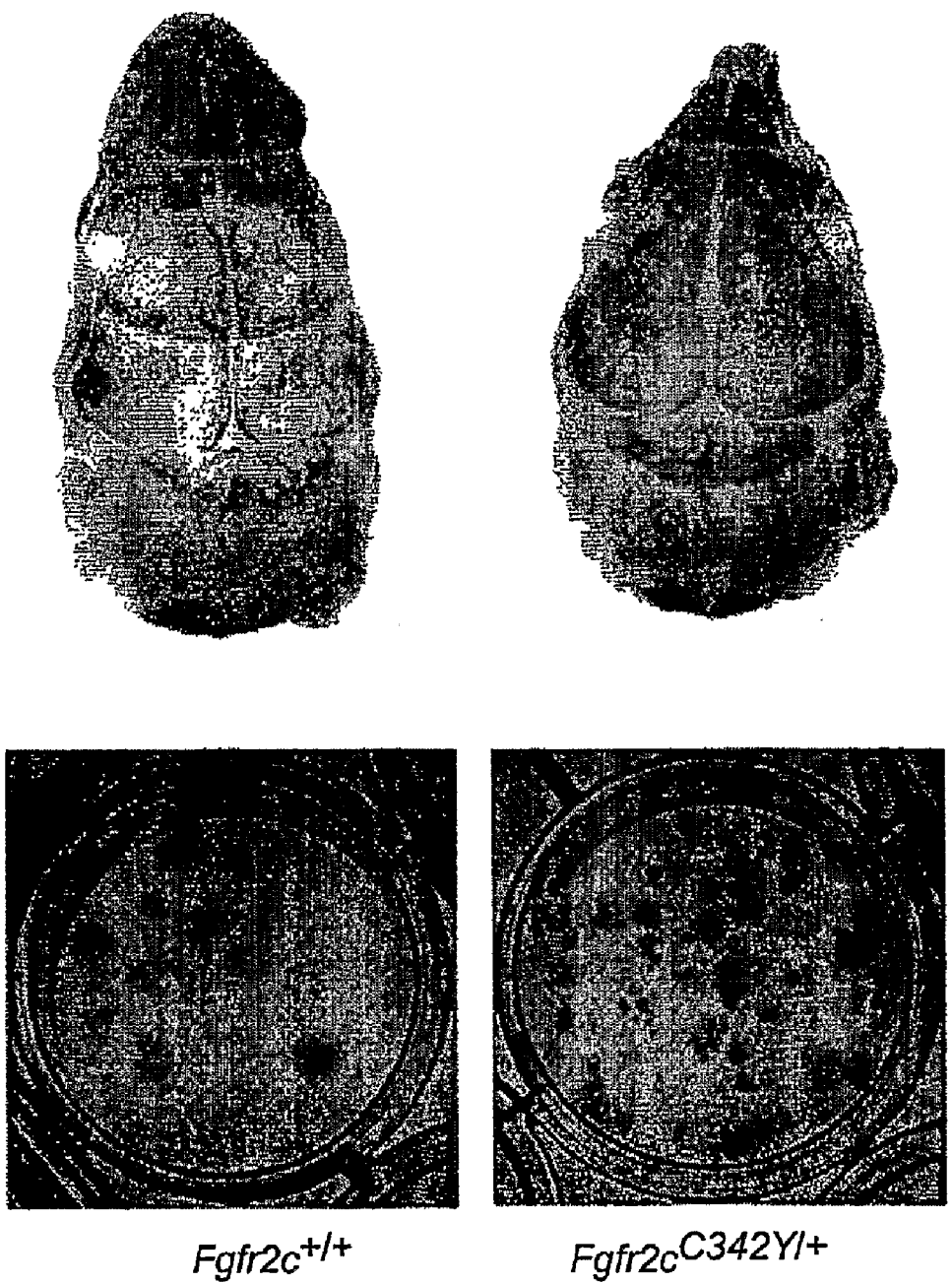
FIG. 9 (top panel) shows the result of a whole mount in situ hybridization with Osteopontin (Spp1) of skulls of wt and Cys342Tyr heterozygote E18.5 embryos. More intense staining of osteopontin hybridization was observed in the heterozygote. The lower panel shows that the Cys342Tyr gain-of-function mutation increases osteoprogenitor cells in the bone marrow, which is consistent with the top panel results.
Figure 10:
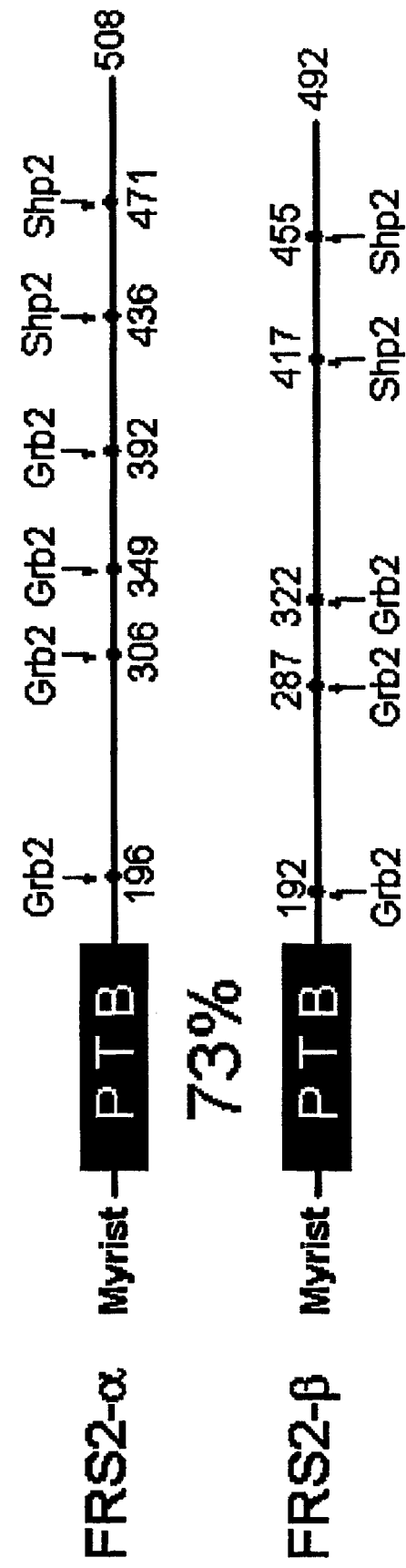
FIG. 10 is a schematic diagram of the two aligned FRS2 isoforms, FRS2α and FRS2β. The N-termini of both isoforms are myristylated to facilitate subcellular localization (e.g. inner plasma membrane). The various Grb2 and Shp2 binding sites are also indicated.

Fgfr2c$^{C342Y/+}$ heterozygote mice are viable and fertile with shortened face, protruding eyes, and slightly rounded and domed cranium (see top panel of FIG. 8), premature fusion of cranial sutures (FIG. 8, lower right panel), and enhanced osteopontin (Spp 1) expression in the calvaria. Mutants can be readily distinguished from their wt litter-mates (see lower left panel of FIG. 8). Osteopontin is one of the major noncollagenous bone matrix proteins expressed by early osteoblasts. Whole-mount in situ hybridization of E18.5 fetal heads revealed a significant increase in Spp1 expression in the nasal, frontal, parietal, and occipital bones in Fgfr2c$^{C342Y/+}$, compared with those of wild type (FIG. 9, top panels). Increased Spp1 expression also was observed in the E18.5 femur (not shown).

Homozygous mutants display multiple joint fusions, cleft palate, and trachea and lung defects, and die shortly after birth. They show enhanced Cbfa1/Runx2 expression without significant change in chondrocyte-specific Ihh, PTHrP, Sox9, Col2a, or Col10a gene expression.

Histomorphometric analysis and bone marrow stromal cell culture showed a significant increase of osteoblast progenitors with no change in osteoclastogenic cells (FIG. 9, bottom panel). Chondrocyte proliferation was decreased in the skull base at embryonic day 14.5 but not later. These results suggest that long-term aspects of the mutant phenotype, including craniosynostosis, are related to the Fgfr2c regulation of the osteoblast lineage. The effect on early chondrocyte proliferation but not gene expression suggests cooperation of Fgfr2c with Fgfr3 in the formation of the cartilage model for endochondral bone.

Thus, like Crouzon syndrome patients who posses one normal and one mutant Fgfr2c allele, the heterozygous Crouzon-like mice showed all the hallmarks of the human disease: premature fusion of coronal sutures, shallow orbits and protruding eyes without limb defects (Eswarakumar et al., *Proc Natl Acad Sci USA* 101: 12555-12560, 2004). These experiments demonstrated that the heterozygote gain-of-function knock-in mutant mouse (Fgfr2c$^{C342Y/+}$) is a proper mouse model for the human Crouzon syndrome and the related syndromes.

Example 3

FGFR2 Mutants Defective in FRS2 Binding

Two FGFR2 mutants potentially defective in FRS2 binding were constructed and tested for FRS2 binding. One of such FRS2 recruitment mutant is the LR mutant, where L424 and R426 of the wt FGFR2 are both replaced by Alanines. Another such FRS2 recruitment mutant is the LRV mutation, where L424, R426, and V428 of the wt FGFR2 are all replaced by Alanines.

In order to test whether such mutants actually fail to bind FRS2, several chimeric constructs were prepared and inserted into a mammalian retroviral vector, pBABE, containing a puromycin resistance gene to express FGFR2, and the various FGFR2 mutants in NIH3T3 and L-6 myoblast cells. In the pBABE-TrkA-wtFR2 chimera, the TrkA extracellular domain was fused N-terminal to the mouse FGFR2 transmembrane domain and the intracellular kinase domain. A FLAG tag was fused to the C-terminus of the construct. In the pBABE-TrkA-LRmtFR2 chimera, the L423A and R425A double mutation were introduced into an otherwise identical construct (the LR mutant). In the pBABE-TrkA-LRVmtFR2 chimera, the L423A, R425A, and V427A triple mutation were introduced into an otherwise identical construct (the LRV mutant).

Cells expressing wild type, chimeric receptors or FGFR mutants were serum starved overnight and stimulated with NGF or FGF1 and at different ligand concentrations and as a function of time. The cells were lysed in a buffer composed of 25 mM Hepes, 150 mM NaCl, 1 mM EDTA, 1% Triton X-100, 20 mM β-glycerophosphate, 10 mM pyrophosphate, 1 mM NaVO$_3$, 1 mM PMSF, 5 μg/ml leupeptin. Cell lysates were subjected to immunoprecipitation with different antibodies; anti-Fgfr2, anti-FLAG (M2, Sigma), anti-FRS2α, anti-Grb2, anti-Shp2 (Santa Cruz), anti-Shc, anti-PLCγ, anti-Gab1, anti-MAPK, anti-p-MAPK (activated), anti-Akt and anti-p-Akt (activated Akt), followed by immunoblotting with different antibodies. Anti-FRS2α, anti-p-Tyr and anti-Grb2 were previously described. Anti-mouse HRP and ProteinA-HRP were purchased from Santa Cruz Biotechnologies. Anti-FLAG antibodies (M2) were obtained from Sigma.

The various mutations (C342Y, LR and CLR) did not affect the kinase activity as detected by the autophosphorylation level (data not shown).

IP-Western were performed in FRS2-expressing cells transfected with these individual constructs, by using an anti-FLAG antibody to immuno-precipitate the chimeric receptors, and either an anti-FLAG antibody or an anti-pTyr (phospho-Tyrosine) antibody for immuno-blotting. These experiments indicated that both the LR mutant and the LRV mutant failed to bind FRS2a and thus failed to stimulate Tyr phosphorylation of FRS2a, while normal level of Tyr phosphorylation was observed if the chimera containing the wt intracellular domain of FGFR2 were used in the same assay (data shown in U.S. Ser. No. 60/574,085, filed on May 25, 2004, incorporated herein by reference).

In another experiment, lysates from cells transfected with wt, the LR mutant, or the LRV mutant of chimeric FGFR2 were immuno-precipitated with an anti-FRS2 antibody, respectively. Similar amounts of FRS2 were immunoprecipitated in all three chimera experiments (data shown in U.S. Ser. No. 60/574,085, filed on May 25, 2004, incorporated herein by reference). However, anti-FLAG immunoblotting only revealed the presence of wt FGFR2 chimera in the immuno-precipitated FRS2. In other words, neither FGFR2 mutants interacted with FRS2.

To show that the LR or LRV mutation did not impair the function of FGFR2 in a non-specific way, lysates from cells transfected with wt, the LR mutant, or the LRV mutant of chimeric FGFR2 were immuno-precipitated with an anti-Shc antibody. The phosphorylation status of the immuno-precipitated Shc was then determined by anti-pTyr antibody. Shc was properly phosphorylated by both the wt chimera and the LR or LRV mutant chimeras, indicating that neither the LR nor the LRV mutation appreciatably affect FGFR2's ability to phosphorylate another substrate, Shc. Thus the LR and LRV mutants specifically abolish FRS2-mediated FGFR2 signaling, but not other (such as Shc, and also PLCγ-data not shown) FGFR2 signaling.

Example 4

Mutant FGFR2 Containing Both the Crouzon Mutation and Defective FRS2 Binding

Figure 11B:
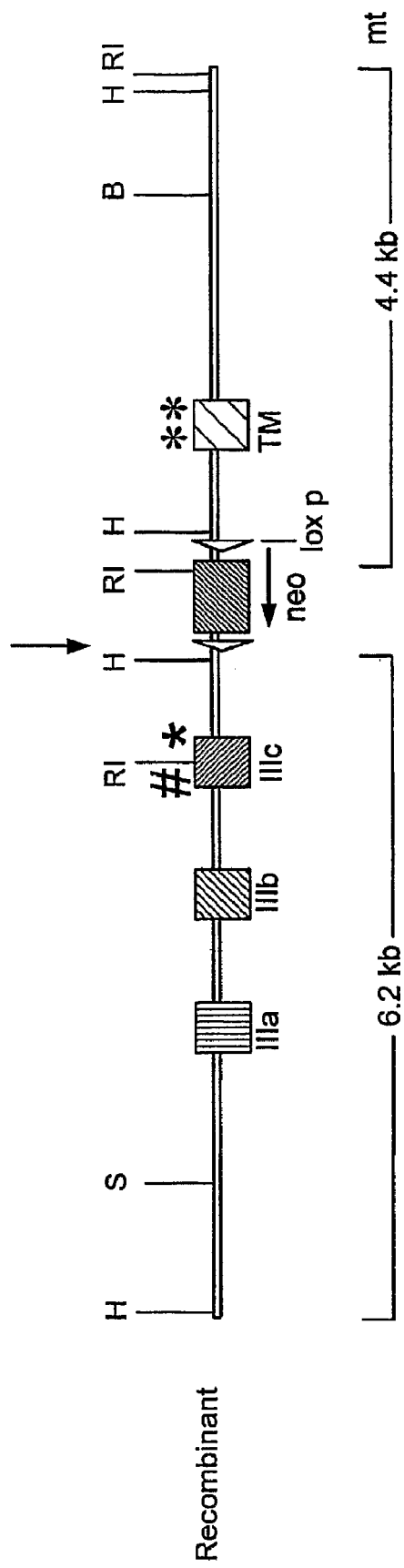
FIG. 11 shows the knock-in targeting strategy for a transgene harboring both the Crouzon mutation Cys342Tyr, and mutation(s) that impairs the recruitment and tyrosine phosphorylation of FRS2. One of such FRS2 recruitment mutations is the LR mutation, where L424 and R426 of the wt FGFR2 are both replaced by Alanines. Another such FRS2 recruitment mutation is the LRV mutation, where L424, R426, and V428 of the wt FGFR2 are all replaced by Alanines.
Figure 12:
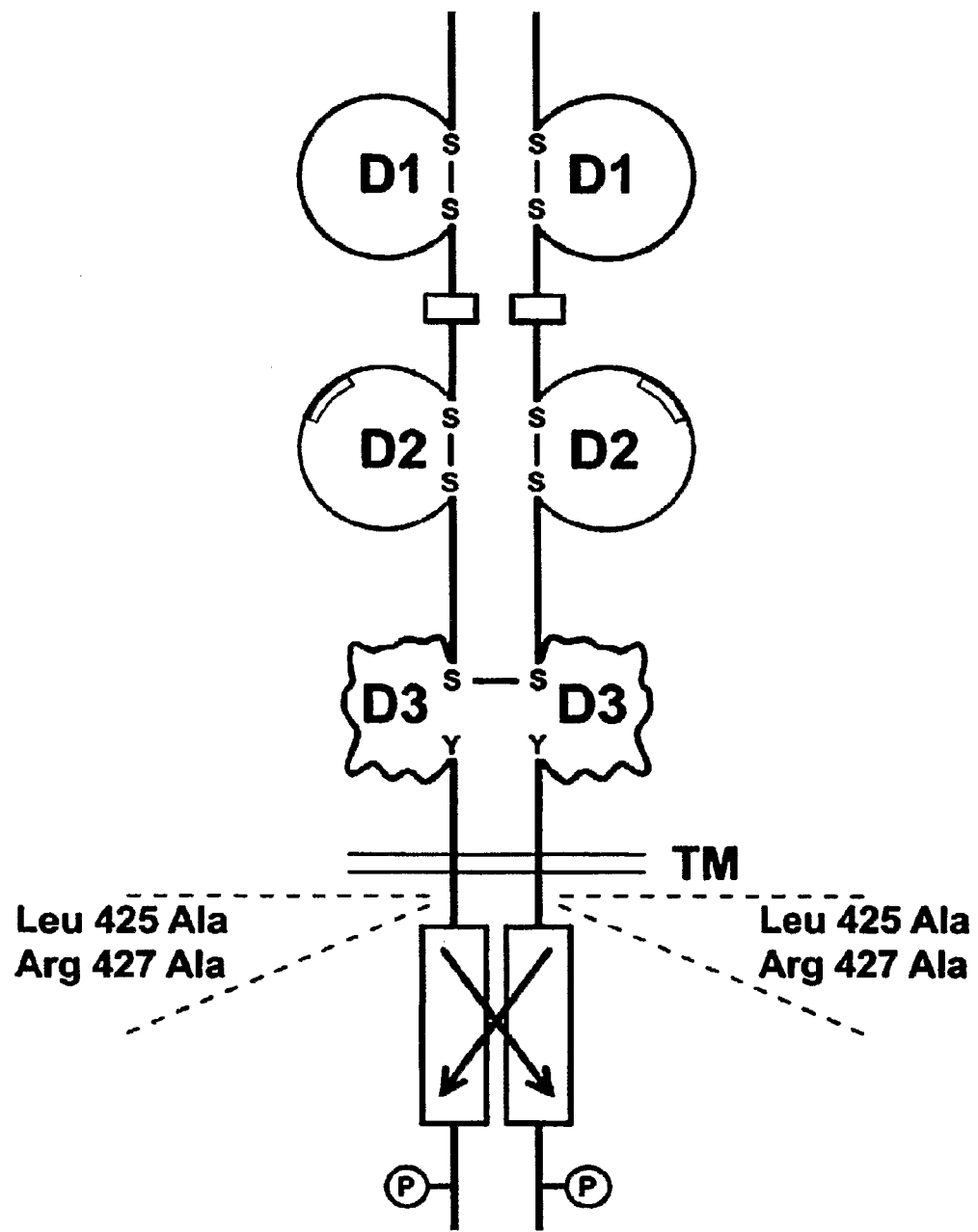
FIG. 12 is a schematic drawing of C342Y & LR double mutant. The C342Y mutation leads to intermolecular disulfide bond formation and ligand-independent FGFR dimerization, and the subsequent autophosphorylation. However, the LR mutation impairs FRS2 recruitment and FRS2 phosphorylation by the constitutively active FGFR2.

Having demonstrated that the LR or the LRV mutation in the intracellular domain of FGFR2 abolishes FRS2 binding, phosphorylation, activation (and thus FRS2-mediated signaling), Applicants established a knock-in mouse harboring both the Crouzon mutation C342Y, and the LR mutation that abolishes FGFR signaling through FRS2 (see FIG. 11 for targeting strategy). This mouse line would be useful for assessing the effect of antagonizing the FRS2-mediated FGFR signaling.

Specifically, Mouse genomic fragment derived from 129SvJ including exons 7, 8, 9 and 10 of Fgfr2 was used for site-directed mutagenesis, using the "Gene Editor" kit (Promega) according to the manufacturer's instructions. The C342Y mutation in exon 9 was created by changing the codon TGC to TAC. This mutation also created a unique diagnostic restriction site (Rsa I) in the exon9. L424A and R426A mutations were created in exon 10 by changing the codons CTG to GCG (185 nucleotides after the beginning of exon 10), and AGA to GCC (191 nucleotides after the beginning of exon 10). These mutations were designed in such a way to create a new diagnostic restriction site Apa I in exon 10. Mutagenized fragment was ligated into the "Osdupdel" vector (Gift from Oliver Smithies, Chapel Hill). Targeting vector was linearized by Not I and electroporated into W9.5 ES cells. G418 and Gancyclovir resistant clones were screened by Southern blot hybridization for targeting events. Correctly recombined ES clones were used to make chimeras by injecting into blastocysts derived from C57B1/6 strain. The floxed neo cassette was removed in vivo from both strains by mating to the PGK-Cre$^m$ transgenic deleter strain (Lallemand et al., 1998).

Genomic DNA was isolated from tail clips and genotype determined using primers designed to amplify 206 bp of neo gene (FP: 5' AGAGGCTATTCGGCTATGACTG-3', SEQ ID NO: 1, and RP: 5'AGTGACAACGTCGAGCACAG-3', SEQ ID NO: 2), or in the case of neo removed alleles, primers flanking the residual loxp site in the intron 9 region (FP: 5'-GAGTACCATGCTGACTGCATGC-3', SEQ ID NO: 3, and the RP: 5' GGAGAGGCATCTCTGTTTCAAGACC-3', SEQ ID NO: 4) were used. The wt allele gives 200 bp and mt allele gives 290 bp PCR products.

Surprisingly, the LR mutation greatly suppressed the C342Y mutant phenotype, in that the C342Y/LR double mutant ("CLR") had a grossly normal phenotype that is virtually indistinguishable from its wt littermate (FIG. 13, top panels). At six weeks of age the Fgfr2c$^{C342Y/+}$ Crouzon-like mice are characterized by ocular proptosis (protruding eyes), rounded cranium and severe reduction in the development of the midfacial area (FIG. 13, top panels). Most of the mutants have malocclusion causing feeding difficulty. The heterozygous Fgfr2c$^{CLR/+}$ mice, on the other hand, are normal without any sign of defect in craniofacial development (FIG. 13, top panels).

Figure 13A:
FIGS. 13A-13D show the result of the analysis of the morphology and anatomy of skulls of 6 week old WT, Fgfr2c$^{C342Y/+}$, and Fgfr2c$^{CLR/+}$ mice. (A) Photographs of the heads of live mice; (B) Alizarin stained skulls; (C) micro-CT scans showing three 5 dimensional images of calvaria, note completely fused coronal suture in Fgfr2c$^{C342Y/+}$ mutant mice (arrow) and open sutures in WT and Fgfr2c$^{CLR/+}$ mice; (D) Two dimensional images of cross section of coronal suture showing open suture of WT mice, fused suture of Fgfr2c$^{C342Y/+}$ mice and open suture of Fgfr2c$^{CLR/+}$ mice. Left, wild type; middle, Crouzon mutant; right, rescued triple mutant. Abbreviations: C, coronal suture; S, sagittal suture; L, lambdoid suture; F, frontal suture.
Figure 13B:
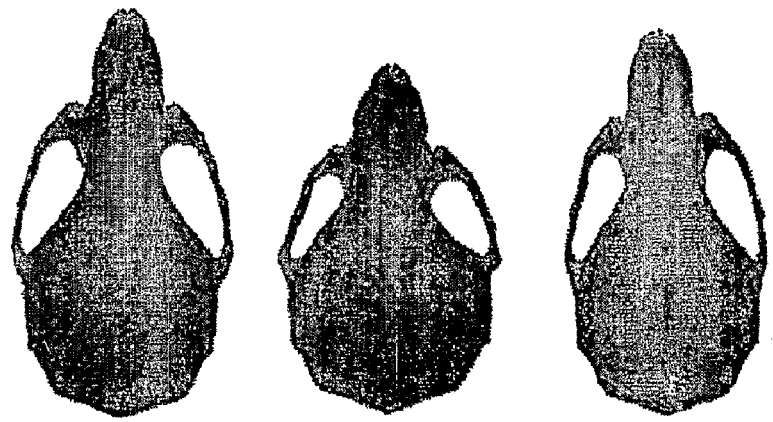

To further characterize these mice, the heads of WT, Fgfr2c$^{C342Y/+}$ and Fgfr2c$^{CLR/+}$ mice were harvested and stained with Alizarin red using a standard protocol (see below). All the sutures are readily visible in wild type and in Fgfr2c$^{CLR/+}$ mutant mice, whereas in Fgfr2c$^{C342Y/+}$ mutant mice, the coronal sutures are completely fused (FIG. 13B).

Figure 13C:
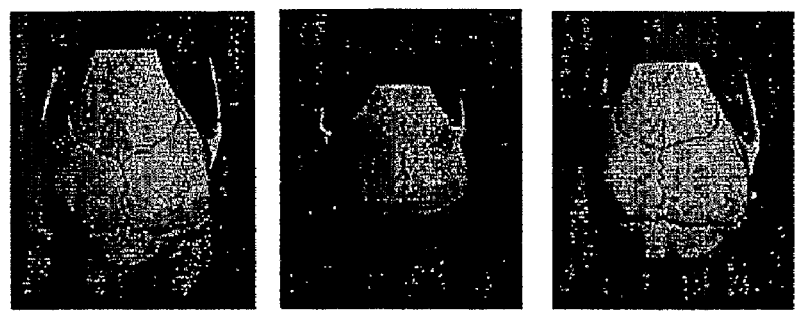

We also used micro computed tomography (microCT) imaging to analyze the fine details of the cranial sutures. MicroCT analysis skull vault sutures were carried using a desktop μCT imaging system (μCT40; Scanco Medical AG). The 3-D images of the calvaria show that wild type mice have fully opened coronal, sagittal and lambdoid sutures (FIG. 13C, left panel). These sutures are normally open throughout the life span of the mouse except the frontal suture. In the Cruzon-like mutant mice, the coronal and frontal sutures are fully fused and the sagittal suture is partially closed at the anterior end (FIG. 13C, middle panel). Like the sutures of wild type mice, the coronal, sagittal and lambdoid sutures of heterozygotes of Fgfr2c$^{CLR/+}$ mice remain fully opened (FIG. 13C, right panel).

Figure 13D:

The sutures were further examined by analyzing 2-D images of the coronal suture cross section (FIG. 13D). Both in the wild type and in the Fgfr2c$^{CLR/+}$ mice (FIG. 13D, left and right respectively) the coronal sutures are open with the overlapping ossified frontal and parietal bones, whereas these two bones are completely fused in the coronal suture of the Crouzon-like Fgfr2c$^{C342Y/+}$ mice (FIG. 13D, middle).

The fact that the heterozygous FRS2-recruitment deficient Crouzon-like mutant mice (Fgfr2c$^{CLR/+}$) did not show any sign of craniosynostosis and are phenotypically indistinguishable from wild type littermates prompted us to explore the possibility of whether mutation in the juxtamembrane domain (L424A; R426A) inactivated the mutant alleles that carry Crouzon mutation in the extracellular domain (C342Y). It has been shown that targeted inactivation of Fgfr2 in toto, that lead to the inactivation of both the b and c isoforms of Fgfr2, causes an embryonic lethal phenotype at E10.5 due to impairment in the development of the placenta (Xu et al., *Development* 125: 753-765, 1998). This has been tested by intercrossing Fgfr2c$^{CLR/+}$ to generate Fgfr2c$^{CLR/CLR}$ mice. Genotyping of the newborn pups has shown that 25% of the offspring were homozygous Fgfr2c$^{CLR/CLR}$ mice. This experiment shows that the LR mutations did not inactivate the Fgfr2c gene as, otherwise, the Fgfr2c$^{CLR/CLR}$ embryos would not have survived beyond E10.5 because of the impairment in placenta development caused by inactivation of the Fgfr2 locus (Xu, supra).

We also compared the histology of the coronal suture of one week old mice. In the Crouzon-like Fgfr2c$^{C342Y/+}$ mice, the coronal suture is distorted and the sutural mesenchyme has completely lost the overlapping frontal and parietal bones and started to show the signs of synostosis at this age. The sutural mesenchyme was filled with mineralized matrix as revealed by the Van Kossa staining (not shown). However, in the wild type and in Fgfr2c$^{CLR/+}$ mice, the coronal suture has a well developed sutural mesenchyme containing overlapping frontal and parietal bones (nor shown).

Although complete rescue of craniosynostosis was achieved in the heterozygotes, the same complete reversal of the phenotype was not seen in the homozygotes. This is not of great clinical significance, since most craniosynostosis individuals are heterozygotes.

If all the signals are transmitted through FRS2 proteins, then one would expect that the Fgfr2-CLR$^{-/-}$ mice may resemble the Fgfr2c$^{-/-}$ knockout mice. The homozygous mice of CLR mutation die within a day after birth. This observation suggests that in the absence of regulated signaling, the constitutively activated kinase of the mutant receptors recruit and transmit signals through other pathways independent of FRS2 signaling. These signaling pathways may be mediated by but not restricted to Shc, PLC-γ etc. Such signaling pathways exist in the Fgfr2-CLR$^{+/-}$ heterozygous mice but they may be too little to cause any phenotype in these animals.

The experiments presented so far demonstrate that selective uncoupling of the activated Crouzon-like FGFR2c mutant from interactions with FRS2 results in attenuation of the signaling pathways downstream of the mutant FGFR2c leading to normal development of the skull mediated by the normal allele of FGFR2c. Pharmacological interventions that would interfere with the interactions between the PTB domain of FRS2 and the juxtamembrane domain of FGFR2 are thus useful approach for the treatment of Crouzon syndrome and other craniofacial disorders that are caused by activated forms of FGFRs.

Such pharmacological interventions may specifically interfere with the FGFR-FRS2 interaction. Alternatively, a protein tyrosine kinase (PTK) inhibitor that inhibits the activity and action of FGFRs may be used. Such PTK inhibitor could be applied at a limited dose that on one hand will attenuate the signaling pathways that arise from the Crouzon like mutant to diminish the adverse affects but on the other hand will still enable the transmission of sufficient signals from wild type FGFR2c to mediate the beneficial response induced by FGF stimulation. An example of such pharmacological intervention is described below.

Example 5

Inhibition of FGFR by Small Molecule Inhibitor

The mechanism of inhibition of FGFR tyrosine kinase activity was determined by the crystal structure of PLX052 (see FIG. 14C for structure) in complex with the catalytic tyrosine kinase domain of FGFR1. The inhibitor, PLX052, binds in the nucleotide binding pocket formed by the cleft between the two lobes of the kinase (FIGS. 14A and 14B). The inhibitor does not make direct contacts with either the nucleotide binding loop or the catalytic region, but rather lies in the vicinity of both and adopts a position similar to an ATP analog. PLX052 forms three hydrogen bonds and numerous hydrophobic interactions with the kinase domain. The 1H-pyrrolo[2,3-b]pyridine-3-yl ring forms 2 hydrogen bonds with the kinase backbone. The pyridine ring nitrogen makes contact with the amide nitrogen of Ala$^{564}$ and the pyrrole ring nitrogen contacts the backbone carbonyl oxygen of Glu$^{562}$. A third hydrogen bond is formed between the oxygen of the 3-methoxyphenyl ring of the inhibitor and the amide nitrogen of Asp$^{641}$.

We first tested the effect of PLX052 in vitro for blocking the activation of FGFR2. Cells were pretreated for 5 minutes with the compound before stimulation. The result presented in FIG. 14D shows that PLX052 efficiently inhibits FGFR activation to basal levels at as low as 10 µM by blocking the tyrosine autophosphorylation of FGFR2 following ligand stimulation. We further tested the ability of PLX052 in blocking the FRS2 phosphorylation in mutant cells expressing constitutively activated Crouzon-like mutant Fgfr2c isoform. We here demonstrate significant reduction in the phosphorylation of FRS2α in cells treated with PLX052 (results not shown) as well as attenuated MAP Kinase signaling (results not shown).

Figure 15A:
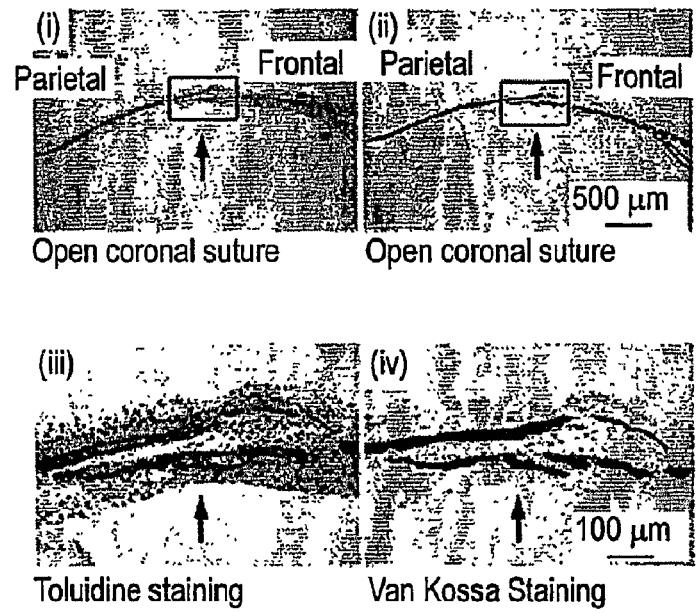
FIGS. 15A-15D show results of in vitro culture of calvaria with FGFR inhibitor PLX052. Calvaria harvested from the Crouzon mutant and wild type E18.5 day old embryos were cultured in DMEM medium containing 10% FCS supplemented with ascorbic acid at 100 µg/ml and 1 µM PLX052 in 24 well plates. Medium was changed on alternate days along with the inhibitor. Controls were cultured with the vehicle only (0.2% DMSO). Calvaria were cultured for 14 days. After the specified time, calvaria were fixed in 10% buffered formalin, dehydrated followed by infiltration and embedding in methylmethacrylate plastic. Blocks were cut perpendicular to the coronal suture, that passes through the frontal bone (anterior side) and the parietal bone (posterior side). The arrow in FIG. 15.1 shows the plane of sectioning. 4 µM thick sections were collected and stained with toludine blue (FIG. 15.2, left panels). Adjacent sections were stained for minerals of the bone matrix using Van Kossa followed by methyl green counter staining. (A) wild type, and (B), mutant calvaria cultured with the vehicle alone (0.2% DMSO). Note the open suture in the wild type (A) and the fused suture in the mutant (B) cultured calvaria. (C), wild type and (D), mutant cultured with 1 µM PLX052 (in 0.2% DMSO). The left panels [(i), (iii)] are toluidine blue staining and the right panels [(ii), (iv)] are Van Kossa with methyl green counter staining. Lower panels [(iii), (iv)] are the higher magnification of the sutures shown in the boxed region of the upper panels [(i), (ii)]. Note the open suture in the mutant cultured with PLX052 (D).
Figure 15B:
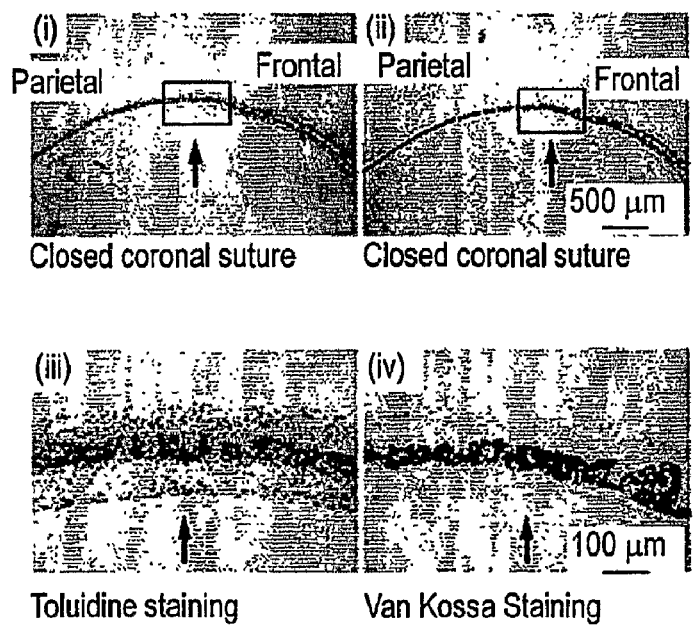
Figure 15C:
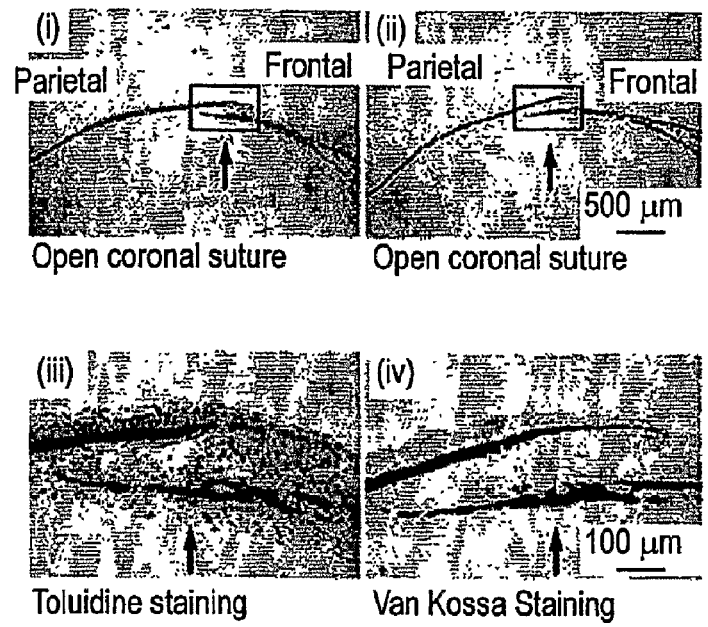
Figure 15D:
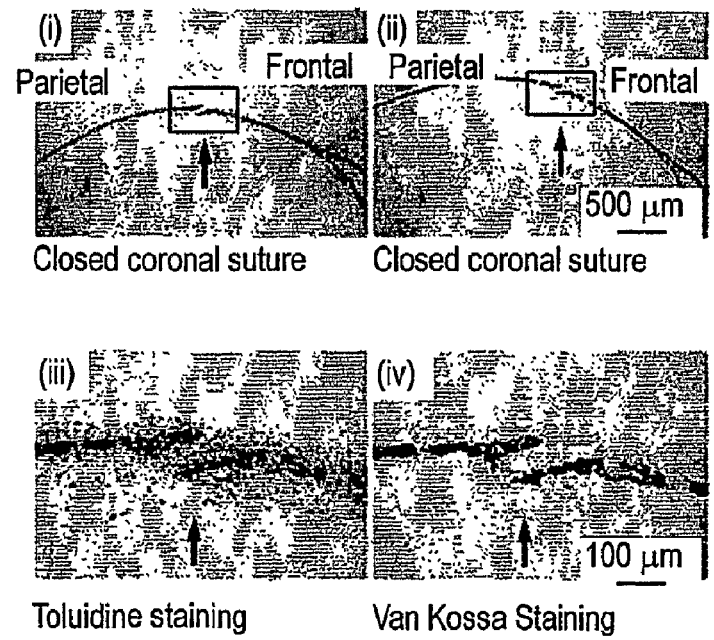

PLX052 prevents cranial suture fusion in vitro. Next, we tested the ability of the PLX052 to prevent craniosynostosis in calvaria organ culture from wt and Crouzon-like mutant mice (FIG. 15). PLX052 was able to rescue the premature fusion of coronal suture in the mutant calvaria in vitro (FIG. 15D). The same concentration (1 µM) did not affect the growth of the wild type suture (FIG. 15C). The calavria organ culture experiments were repeated with two different concentrations of PLX052 (1 µM and 5 µM) and cultured for extended period of time (21 days) to assess the dose response for this inhibitor (see below). The results show that both 1 µM and 5 µM concentration were able to prevent the premature fusion of coronal suture of the mutant mice calvaria without affecting the normal development of the sutures in the wild type. Higher concentrations of PLX052 (50 µM and above) have caused extensive cell death within 24 hours in cultured cells. Therefore, it is feasible to use limited amount of inhibitor to attenuate the abnormal signaling from the mutant receptors without causing adverse effect on the normal signaling pathways.

Thus treatment of calvaria explants from Crouzon-like mutant mice with PLX052 prevents the fusion of sutures without adversely affecting signaling pathways that are activated by the wild type allele of Fgfr2c which is required for normal suture development. The experiments presented herein provide both genetic and pharmacological evidence that modalities that attenuate signaling pathways that are stimulated by pathologically activated FGFRs could be applied for treatment of craniosynostosis and other severe bone disorders that are caused by activated forms of FGFRs.

The following methods were used in some of the Experiments described above.

Histology

Skulls were harvested from wild type and mutant animals. After removing the soft and connective tissue they were fixed in 10% neutral buffered formalin for two days, washed with PBS and transferred to 70% Ethanol for the next 24 hrs. Samples were dehydrated in acetones (90% 1×, 100% 2× for 1 h each). After dehydration, the bones were embedded in methylmethacrylate as described by Ware et al. (*Development* 121: 1283) and 4 μm sections were obtained using a Leica 2165 Microtome and a tungsten carbide knife, D-profile. After deplastification, bones were stained with toluidine blue, pH3.7. Parallel sections were also stained with Van Kossa to evaluate the mineralized bone matrix. Sections were counter stained with methyl green.

Alizarin Red Staining of Skulls

Skulls were harvested and first fixed in 100% ethanol for four days and followed by three days in acetone. The skulls older than one week were fixed directly into acetone. Before staining skulls were treated with 2% KOH for 12 hours. They were then rinsed with water and transferred to staining solution which contained 0.1% Alizarin red S (Sigma 5533) in 1% KOH. After staining for 24 hours, the skeletons were rinsed with water, cleared with 20% glycerol in 1% potassium hydroxide at room temperature until cleared, at which point they were passed through 20%, 50% and 80% glycerol in ethanol and finally 100% glycerol for storage.

Calvaria Organ Culture

Calvaria harvested from the Crouzon mutant and wild type E18.5 day old embryos were cultured in DMEM medium containing 10% FCS supplemented with ascorbic acid at 100 μg/ml in 24 well plates as described (Opperman et al., *J Bone Miner Res* 12: 301-310, 1997). Medium was changed on alternate days along with the FGFR tyrosine kinase inhibitor PLX052. Controls were cultured with the vehicle only (0.2% DMSO). Calvaria were cultured for 14 to 21 days. After the specified time, calvaria were fixed in 10% buffered formalin, dehydrated, followed by infiltration and embedding in methylmethacrylate plastic. Blocks were cut perpendicular to the coronal suture, that passes through the frontal bone (anterior side) and the parietal bone (posterior side). 4 μM thick sections were collected and stained with toludine blue (FIG. 15, left panels). Adjacent sections were stained for minerals using Van Kossa followed by methyl green counter staining (FIG. 15, right panels).

Those skilled in the art will recognize, or be able to ascertain using no more than routine experimentation, numerous equivalents to the specific method and reagents described herein, including alternatives, variants, additions, deletions, modifications and substitutions. Such equivalents are considered to be within the scope of this invention and are covered by the following claims.

The contents of all cited references (including literature references, issued patents, published patent applications as cited throughout this application) are hereby expressly incorporated by reference.

What is claimed is:

1. A method of reducing in an individual the severity of a skeletal deformity caused by a gain of function mutation in fibroblast growth factor receptor (FGFR), comprising administering to the individual a therapeutically effective amount of an agent that inhibits fibroblast growth factor receptor protein kinase substrate 2 (FRS2) interaction with and/or phosphorylation by FGFR, whereby FRS2 interaction with and/or phosphorylation by FGFR is inhibited, wherein the agent is a small molecule compound, and wherein the small molecule is a 3-benzoyl-7-azaindole compound.

2. The method of claim 1, wherein the FGFR exhibits excessive FGFR activity.

3. The method of claim 2, wherein said excessive FGFR activity results from a constitutively activating mutation in the FGFR.

4. The method of claim 2, wherein said excessive FGFR activity results from gain-of-function mutations in the catalytic RTK (Receptor Tyrosine Kinase) domain of FGFR, said RTK domain exhibiting enhanced activity in a ligand-independent manner.

5. The method of claim 2, wherein said excessive FGFR activity results from FGFR overexpression.

6. The method of claim 1, wherein said agent is administered shortly before or after the birth of the individual.

7. The method of claim 1, wherein said agent is administered postnatally for sufficient time and in appropriate doses to reduce the severity of the skeletal deformity.

8. The method of claim 1, wherein the 3-benzoyl-7-azaindole compound is [4-(3,5-difluorophenyl)-1H-pyrrolo[2,3-b]pyridine-3-yl](3-methoxyphenyl)methanone.

* * * * *